(12) United States Patent
Ibrahim et al.

(10) Patent No.: US 8,198,273 B2
(45) Date of Patent: Jun. 12, 2012

(54) COMPOUNDS AND METHODS FOR KINASE MODULATION, AND INDICATIONS THEREFOR

(75) Inventors: Prabha N. Ibrahim, Mountain View, CA (US); Wayne Spevak, Berkeley, CA (US); Hanna Cho, Oakland, CA (US); Songyuan Shi, San Diego, CA (US); Guoxian Wu, Palo Alto, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 12/773,798

(22) Filed: May 4, 2010

(65) Prior Publication Data

US 2010/0286142 A1    Nov. 11, 2010

Related U.S. Application Data

(60) Provisional application No. 61/176,054, filed on May 6, 2009.

(51) Int. Cl.
  *A61K 31/5377* (2006.01)
  *A61K 31/437* (2006.01)
  *A61K 31/506* (2006.01)
  *C07D 471/04* (2006.01)
  *A61P 35/00* (2006.01)

(52) U.S. Cl. .............. 514/234.5; 514/256; 514/274; 514/300; 544/122; 544/127; 544/316; 544/333; 546/113

(58) Field of Classification Search .............. None
See application file for complete search history.

(56) References Cited

U.S. PATENT DOCUMENTS

| 2004/0077595 A1 | 4/2004 | Cheng et al. |
| 2008/0167338 A1 | 7/2008 | Spevak et al. |
| 2008/0188514 A1 | 8/2008 | Wu et al. |

FOREIGN PATENT DOCUMENTS

| WO | WO-2007/002325 | 1/2007 |
| WO | WO-2007/002433 | 1/2007 |
| WO | WO-2007/009799 | 1/2007 |
| WO | WO-2008/064265 | 5/2008 |
| WO | WO-2008/065417 | 6/2008 |
| WO | WO-2008/079903 | 7/2008 |
| WO | WO-2008/079906 | 7/2008 |
| WO | WO-2009/012283 | 1/2009 |

OTHER PUBLICATIONS

Fischer et al., Cancer Treatment Reviews 2007, 33, 391-406.*
Arbiser, The Journal of Clinical Investigation, 117, 10, 2762-2765.*
Madhusudan et al., Clinical Biochemistry, 2004, 37, 618-635.*
Patani et al., Chem. Rev., 1996, 96, 3147-3176.*
Ibrahim et al., caplus an 2007:11300.*
Panitumumab, http://clinicaltrials.govict2/show/NCT0132054, 2012.*
Khazak et al., 2012, http://www.ncbi.nlm.nih.gov/pmc/articles/PMC2720036/.*
Hentschel et al., 2012, http://www.ncbi.nlm.nih.gov/pubmed/2163917.*
Chappell et al., Oncotarget, March, vol. 2, No. 3, 135-164 (2011).*
Sorafenib, 2012, http://www.cancer.gov/cancertopics/druginfo/sorafenibtosylate.*
U.S. Appl. No. 61/054,445, filed May 19, 2008, Ibrahim et al.
U.S. Appl. No. 61/060,418, filed Jun. 10, 2008, Ibrahim et al.
Bagshawe, K., Antibody-Directed Enzyme Prodrug Therapy: A Review, Drug Dev. Res., 34:220-230 (1995).
Balak, et. al., Novel D761Y and common secondary T790M mutations in epidermal growth factor receptor-mutant lung adenocarcinomas with acquired resistance to kinase inhibitors. Clin. Cancer Res. 12:6494-501 (2006).
Bertolini et al., A new Rational Hypothesis for the Pharmacophore of the Active Metabolite of Leflunomide, a Potent Immunosuppressive Drug; 1997, J. Med. Chem., 40:2011-2016.
Chou, T. and Talalay, P., Quantitative analysis of Dose-Effect Relationships: The Combined Effects of Multiple Drugs or Enzyme Inhibitors, Adv. Enzyme Regul. 22:27-55 (1984).
Chou, T. et al., Chemotherapeutic Synergism, Potentiation and Antagonism, Encyclopedia of Human Biology, Academic Press, 2:371-9 (1991).
Chou, T.C. and Rideout, D.C., editors: Synergism and Antagonism in Chemotherapy, San Diego, CA: Academic Press, Chapter 2, 61-102 (1991).
Hood, J.D. et al., Tumor regression by targeted gene delivery to the neovasculature. (2002), Science 296: 2404.
International Search Report dated Jun. 30, 2010 in related application PCT/US2010/033576.
International Search Report dated Sep. 13, 2010 in application PCT/US2010/033571.
Kunnimalaiyaan et al., The Raf-1 pathway: a molecular target for treatment of select neuroendocrine tumors? Anticancer Drugs (2006), 17(2):139-42.
Niihori et al., Germline KRAS and BRAF mutations in cardio-facio-cutaneous syndrome. Nat Genet. (2006), 38(3):294-6.
Remington: The Science and Practice of Pharmacy, Remington's Pharmaceutical Sciences, 19th ed., Mack Publishing Co., Easton, PA, vol. 2, p. 1457, (1995).
Shan et al., Prodrug strategies based on intramolecular cyclization reactions. Journal of Pharmaceutical Sciences, 86:7, 765-767, 1997.

* cited by examiner

*Primary Examiner* — Sun Jae Loewe
(74) *Attorney, Agent, or Firm* — Foley & Lardner LLP; Stephen E. Reiter

(57) ABSTRACT

Compounds and salts thereof, formulations thereof, conjugates thereof, derivatives thereof, forms thereof and uses thereof are described. In certain aspects and embodiments, the described compounds or salts thereof, formulations thereof, conjugates thereof, derivatives thereof, and forms thereof are active on each of BRaf and c-Raf-1 protein kinase, and may also be active on either or both of A-Raf and B-Raf V600E protein kinase. Also described are methods of use thereof to treat diseases and conditions, including melanoma, colorectal cancer, thyroid cancer, ovarian cancer, and biliary tract cancer.

11 Claims, No Drawings

COMPOUNDS AND METHODS FOR KINASE MODULATION, AND INDICATIONS THEREFOR

CROSS-REFERENCE TO RELATED PATENT APPLICATIONS

This application claims the benefit of U.S. Provisional Application No. 61/176,054, filed May 6, 2009, which is incorporated herein by reference in its entirety and for all purposes.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. In certain embodiments, the compounds inhibit one or more Raf protein kinases, including one or more of A-Raf, B-Raf, and c-Raf-1, and any mutations thereof. In certain embodiments, the compounds inhibit each of c-Raf-1, B-Raf, and B-Raf V600E protein kinase.

Also contemplated in accordance with the present invention are methods for the use of the compounds in treating diseases and conditions associated with regulation of the activity of one or more Raf protein kinases, including one or more of A-Raf, B-Raf, and c-Raf-1, and any mutations thereof. Thus, the use of compounds for therapeutic methods involving modulation of protein kinases are provided. In certain embodiments, the compounds inhibit the activity on one or more Raf kinases, including A-Raf, B-Raf and/or c-Raf-1, including any mutations thereof. In certain embodiments, the compounds are used for therapeutic methods involving modulation of one or more Raf protein kinases, including treatment of a variety of indications, including, but not limited to, melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain and polycystic kidney disease. In certain embodiments, the compounds are used for therapeutic methods involving modulation of B-Raf V600E mutant protein kinase, including treatment of a variety of indications, including, but not limited to, melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In certain embodiments, the compounds are used for therapeutic methods involving modulation of c-Raf-1 protein kinase, including treatment of a variety of indications, including, but not limited to, acute pain, chronic pain and polycystic kidney disease.

In a first aspect, compounds having the structure according to the following Formula I are provided:

Formula I

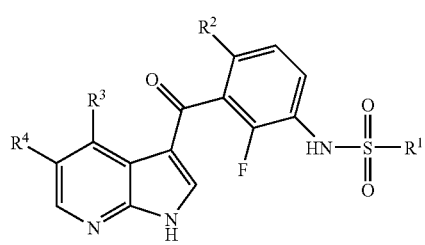

or a salt, a prodrug, or a tautomer thereof, wherein:

$R^1$ is selected from the group consisting of

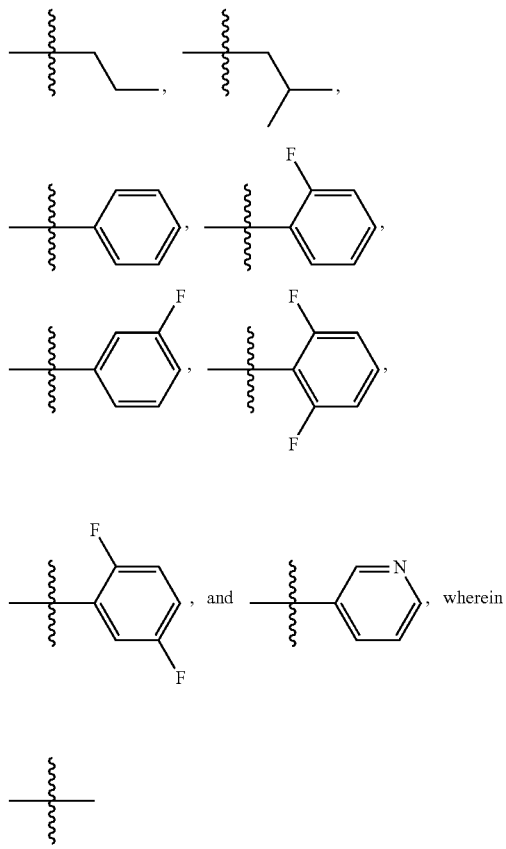

indicates the point of attachment of $R^1$ to the $S(O)_2$ shown in Formula 1;

$R^2$ is hydrogen or fluoro;

$R^3$ is hydrogen, chloro, methoxy or cyano;

$R^4$ is selected from the group consisting of hydrogen, chloro, methyl, methoxy, cyano,

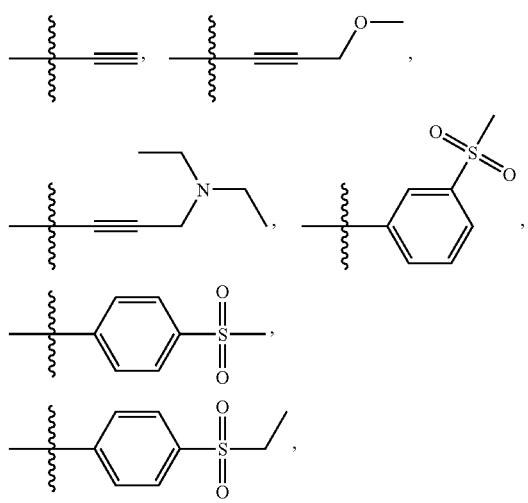

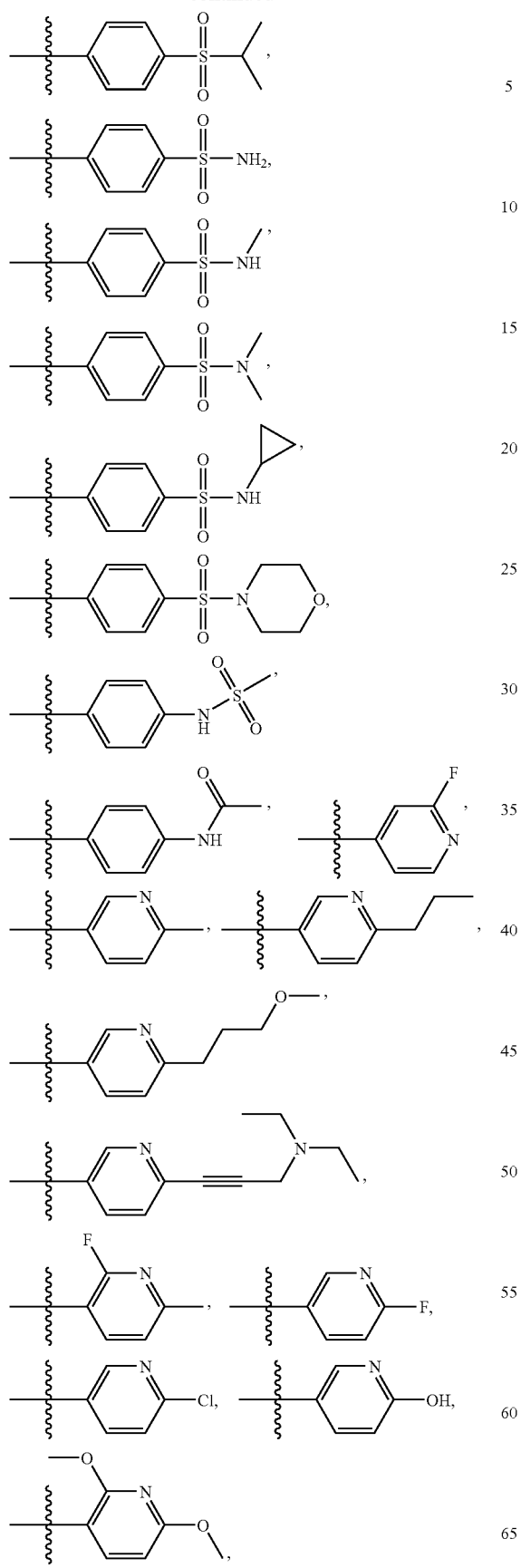
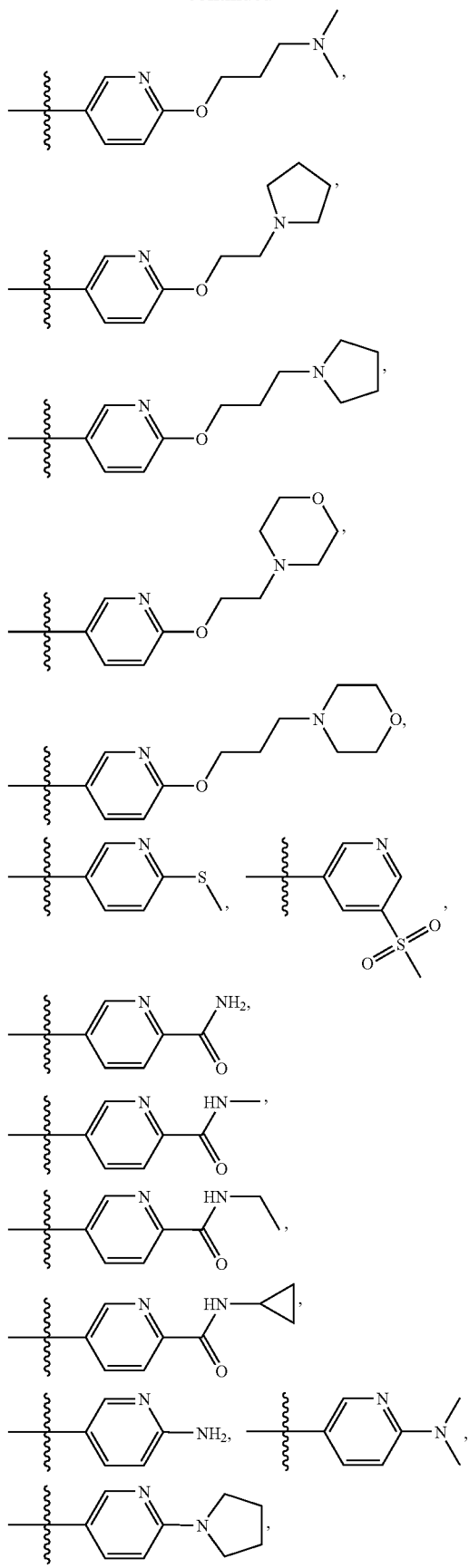

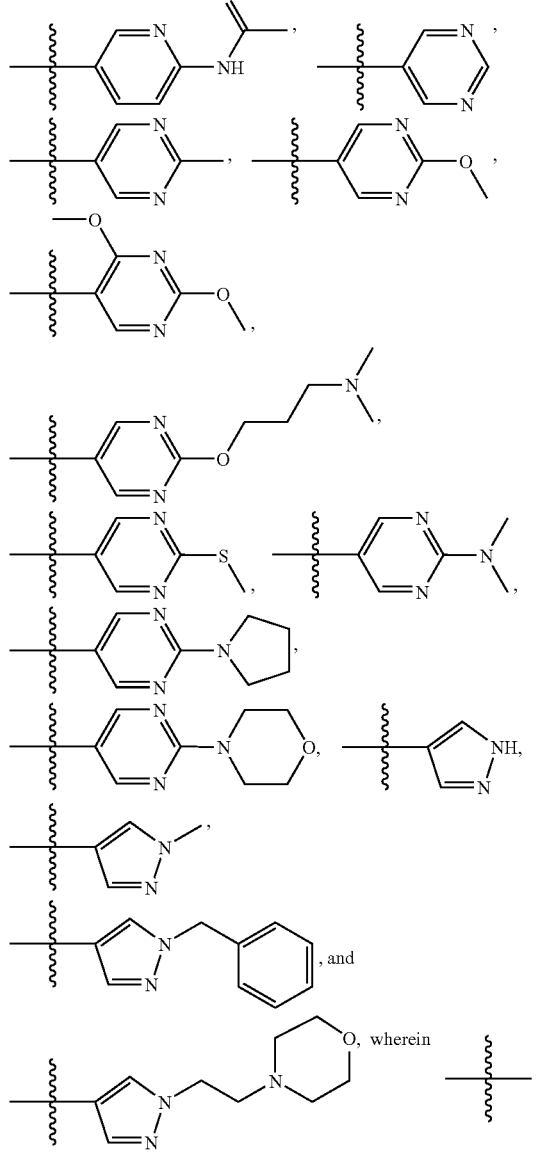
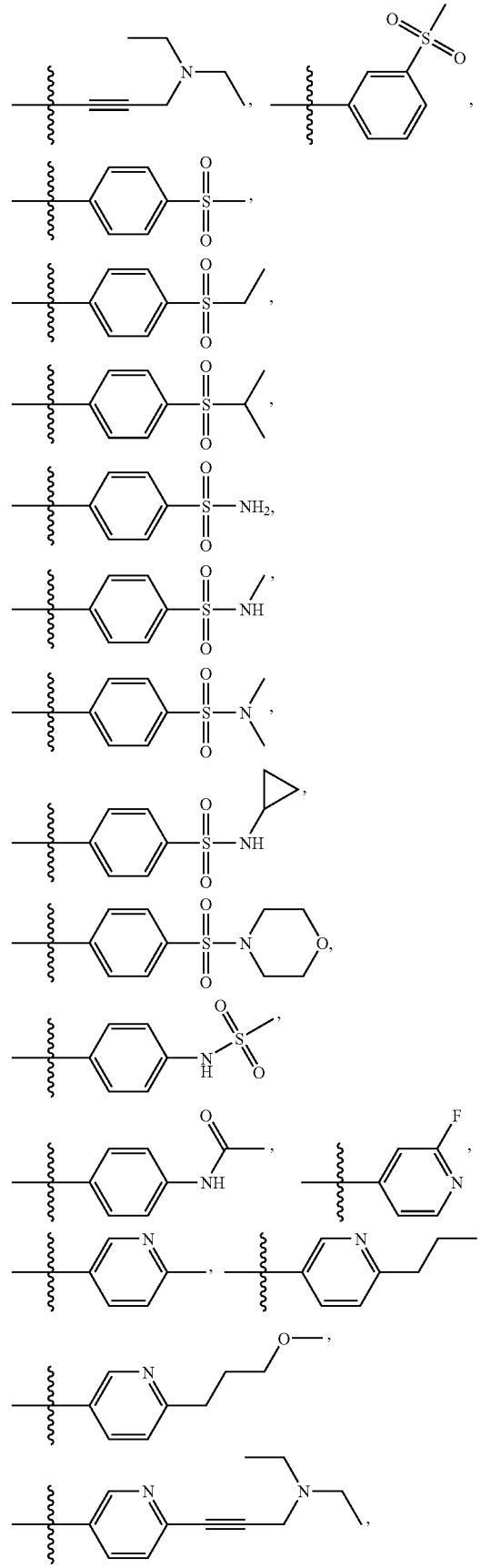
indicates the point of attachment of $R^4$ to the 5-position of the pyrrolo[2,3-b]pyridine ring shown in Formula I;
  wherein:
  when $R^1$ is
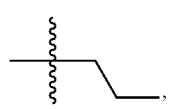
$R^2$ is fluoro, and $R^3$ is hydrogen, $R^4$ is selected from the group consisting of

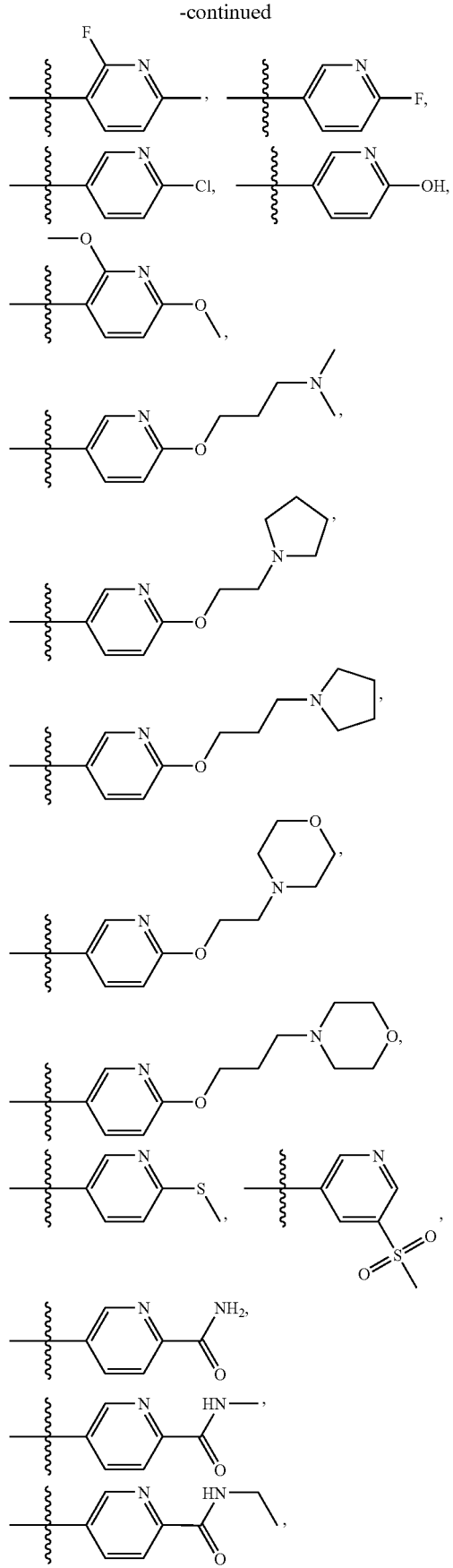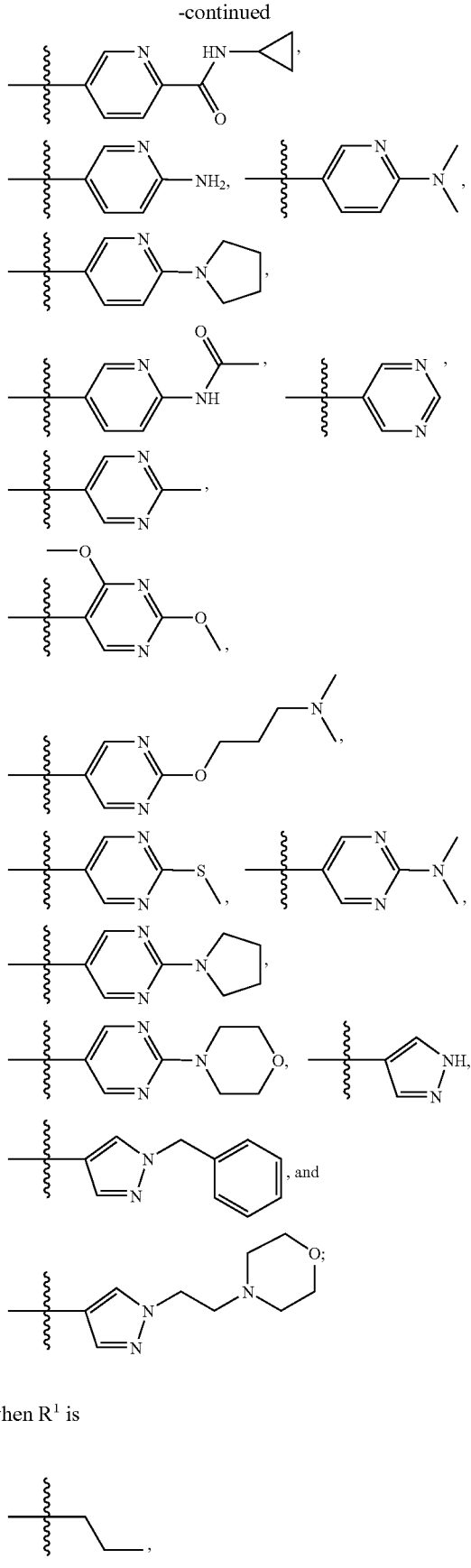
when R[1] is
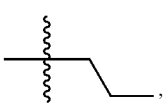, $R^2$ is hydrogen, and $R^3$ is hydrogen, $R^4$ is

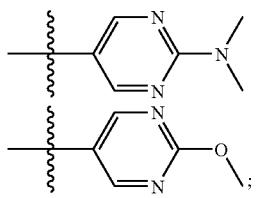 or 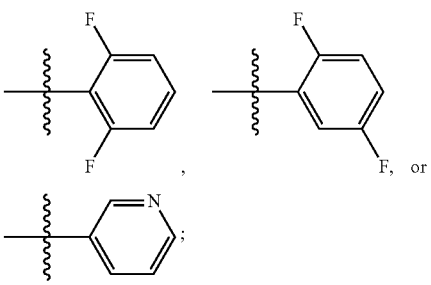

when $R^1$ is

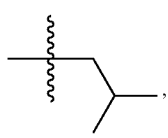, $R^2$ is fluoro, and $R^3$ is hydrogen, $R^4$ is

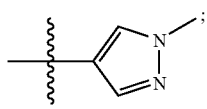;

when $R^1$ is

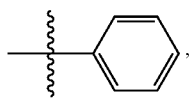, when $R^2$ is hydrogen, $R^3$ is hydrogen, and $R^4$ is cyano, $R^1$ is

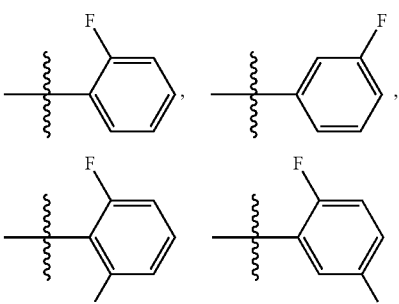

when $R^1$ is

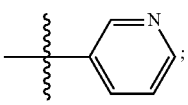

$R^3$ is hydrogen and $R^4$ is cyano, $R^2$ is hydrogen or fluoro; when $R^1$ is

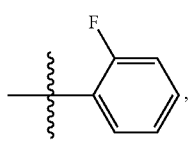, $R^2$ is fluoro, and $R^3$ is hydrogen, $R^4$ is methyl, methoxy, cyano, or

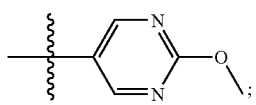;

when $R^2$ is fluoro, $R^4$ is hydrogen, and $R^3$ is chloro, methoxy, or cyano, $R^1$ is

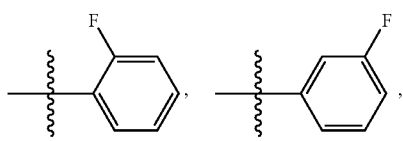, when $R^1$ is

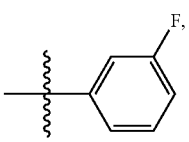

$R^2$ is fluoro, and $R^3$ is hydrogen, $R^4$ is methyl or

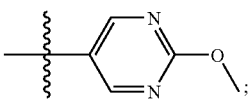;

when $R^1$ is

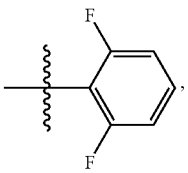

$R^2$ is fluoro, and $R^3$ is hydrogen, $R^4$ is chloro, methyl, cyano, or

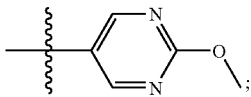

when $R^1$ is

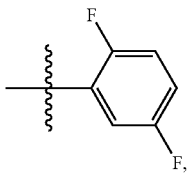

$R^2$ is fluoro, and $R^3$ is hydrogen, $R^4$ is chloro, methyl, methoxy, or

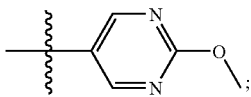

when $R^1$ is

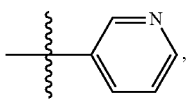

$R^2$ is fluoro, and $R^3$ is hydrogen, $R^4$ is chloro, methyl, or cyano.

In one embodiment of compounds of Formula I, the compound is selected from the group consisting of:

N-[3-(5-Chloro-1H-pyrrolo[2,3-b]pyridine-3-carbonyl)-2,4-difluoro-phenyl]-2,5-difluoro-benzenesulfonamide (P-2002), N-[3-(5-Chloro-1H-pyrrolo[2,3-b]pyridine-3-carbonyl)-2,4-difluoro-phenyl]-2,6-difluoro-benzenesulfonamide (P-2003), N-[2,4-Difluoro-3-(5-methoxy-1H-pyrrolo[2,3-b]pyridine-3-carbonyl)-phenyl]-2-fluoro-benzenesulfonamide (P-2009), N-[2,4-Difluoro-3-(5-methoxy-1H-pyrrolo[2,3-b]pyridine-3-carbonyl)-phenyl]-2,5-difluoro-benzenesulfonamide (P-2010), N-[3-(5-Cyano-1H-pyrrolo[2,3-b]pyridine-3-carbonyl)-2,4-difluoro-phenyl]-2-fluoro-benzenesulfonamide (P-2011), N-[2,4-Difluoro-3-(5-methyl-1H-pyrrolo[2,3-b]pyridine-3-carbonyl)-phenyl]-2-fluoro-benzenesulfonamide (P-2014), N-[2,4-Difluoro-3-(5-methyl-1H-pyrrolo[2,3-b]pyridine-3-carbonyl)-phenyl]-2,5-difluoro-benzenesulfonamide (P-2015), N-[2,4-Difluoro-3-(5-methyl-1H-pyrrolo[2,3-b]pyridine-3-carbonyl)-phenyl]-3-fluoro-benzenesulfonamide (P-2016), N-[3-(4-Chloro-1H-pyrrolo[2,3-b]pyridine-3-carbonyl)-2,4-difluoro-phenyl]-2-fluoro-benzenesulfonamide (P-2017), N-[3-(4-Chloro-1H-pyrrolo[2,3-b]pyridine-3-carbonyl)-2,4-difluoro-phenyl]-2,5-difluoro-benzenesulfonamide (P-2018), N-[3-(4-Chloro-1H-pyrrolo[2,3-b]pyridine-3-carbonyl)-2,4-difluoro-phenyl]-3-fluoro-benzenesulfonamide (P-2019), N-[3-(4-Cyano-1H-pyrrolo[2,3-b]pyridine-3-carbonyl)-2,4-difluoro-phenyl]-2-fluoro-benzenesulfonamide (P-2020), N-[2,4-Difluoro-3-(4-methoxy-1H-pyrrolo[2,3-b]pyridine-3-carbonyl)-phenyl]-2-fluoro-benzenesulfonamide (P-2021), N-[2,4-Difluoro-3-(4-methoxy-1H-pyrrolo[2,3-b]pyridine-3-carbonyl)-phenyl]-2,5-difluoro-benzenesulfonamide (P-2022), N-[2,4-Difluoro-3-(4-methoxy-1H-pyrrolo[2,3-b]pyridine-3-carbonyl)-phenyl]-3-fluoro-benzenesulfonamide (P-2023), N-[2,4-Difluoro-3-(5-methyl-1H-pyrrolo[2,3-b]pyridine-3-carbonyl)-phenyl]-2,6-difluoro-benzenesulfonamide (P-2024), N-[3-(5-Cyano-1H-pyrrolo[2,3-b]pyridine-3-carbonyl)-2,4-difluoro-phenyl]-2,6-difluoro-benzenesulfonamide (P-2029), N-[2,4-Difluoro-3-(4-methoxy-1H-pyrrolo[2,3-b]pyridine-3-carbonyl)-phenyl]-2,6-difluoro-benzenesulfonamide (P-2031), N-[3-(4-Chloro-1H-pyrrolo[2,3-b]pyridine-3-carbonyl)-2,4-difluoro-phenyl]-2,6-difluoro-benzenesulfonamide (P-2033), N-[3-(4-Cyano-1H-pyrrolo[2,3-b]pyridine-3-carbonyl)-2,4-difluoro-phenyl]-2,5-difluoro-benzenesulfonamide (P-2036), N-[3-(4-Cyano-1H-pyrrolo[2,3-b]pyridine-3-carbonyl)-2,4-difluoro-phenyl]-2,6-difluoro-benzenesulfonamide (P-2037), N-[3-(4-Cyano-1H-pyrrolo[2,3-b]pyridine-3-carbonyl)-2,4-difluoro-phenyl]-3-fluoro-benzenesulfonamide (P-2039), N-{2,4-Difluoro-3-[5-(2-methoxy-pyrimidin-5-yl)-1H-pyrrolo[2,3-b]pyridine-3-carbonyl]-phenyl}-2-fluoro-benzenesulfonamide (P-2041), N-{2,4-Difluoro-3-[5-(2-methoxy-pyrimidin-5-yl)-1H-pyrrolo[2,3-b]pyridine-3-carbonyl]-phenyl}-2,5-difluoro-benzenesulfonamide (P-2042), N-{2,4-Difluoro-3-[5-(2-methoxy-pyrimidin-5-yl)-1H-pyrrolo[2,3-b]pyridine-3-carbonyl]-phenyl}-2,6-difluoro-benzenesulfonamide (P-2043), N-{2,4-Difluoro-3-[5-(2-methoxy-pyrimidin-5-yl)-1H-pyrrolo[2,3-b]pyridine-3-carbonyl]-phenyl}-3-fluoro-benzenesulfonamide (P-2045), N-[3-(5-Cyano-1H-pyrrolo[2,3-b]pyridine-3-carbonyl)-2,4-difluoro-phenyl]-benzenesulfonamide (P-2046), N-[3-(5-Cyano-1H-pyrrolo[2,3-b]pyridine-3-carbonyl)-2-fluoro-phenyl]-2-fluoro-benzenesulfonamide (P-2051), N-[3-(5-Cyano-1H-pyrrolo[2,3-b]pyridine-3-carbonyl)-2-fluoro-phenyl]-2,5-difluoro-benzenesulfonamide (P-2052), N-[3-(5-Cyano-1H-pyrrolo[2,3-b]pyridine-3-carbonyl)-2-fluoro-phenyl]-3-fluoro-benzenesulfonamide (P-2053), N-[3-(5-Cyano-1H-pyrrolo[2,3-b]pyridine-3-carbonyl)-2-fluoro-phenyl]-2,6-difluoro-benzenesulfonamide (P-2054), N-[3-(5-Cyano-1H-pyrrolo[2,3-b]pyridine-3-carbonyl)-2-fluoro-phenyl]-benzenesulfonamide (P-2056), Pyridine-3-sulfonic acid [2,4-difluoro-3-(5-methyl-1H-pyrrolo[2,3-b]pyridine-3-carbonyl)-phenyl]-amide (P-2069), Pyridine-3-sulfonic acid [3-(5-chloro-1H-pyrrolo[2,3-b]pyridine-3-carbonyl)-2,4-difluoro-phenyl]-amide (P-2071), Pyridine-3-sulfonic acid [3-(5-cyano-1H-pyrrolo[2,3-b]pyridine-3-carbonyl)-2,4-difluoro-phenyl]-amide (P-2072),
Pyridine-3-sulfonic acid [2,4-difluoro-3-(4-methoxy-1H-pyrrolo[2,3-b]pyridine-3-carbonyl)-phenyl]-amide (P-2073),
Pyridine-3-sulfonic acid [3-(4-chloro-1H-pyrrolo[2,3-b]pyridine-3-carbonyl)-2,4-difluoro-phenyl]-amide (P-2074),
Pyridine-3-sulfonic acid [3-(4-cyano-1H-pyrrolo[2,3-b]pyridine-3-carbonyl)-2,4-difluoro-phenyl]-amide (P-2077),
Pyridine-3-sulfonic acid [3-(5-cyano-1H-pyrrolo[2,3-b]pyridine-3-carbonyl)-2-fluoro-phenyl]-amide (P-2086),
5-{3-[2,6-Difluoro-3-(propane-1-sulfonylamino)-benzoyl]-1H-pyrrolo[2,3-b]pyridin-5-yl}-pyridine-2-carboxylic acid ethylamide (P-2151),
Propane-1-sulfonic acid {3-[5-(6-chloro-pyridin-3-yl)-1H-pyrrolo[2,3-b]pyridine-3-carbonyl]-2,4-difluoro-phenyl}-amide (P-2154),
Propane-1-sulfonic acid {2,4-difluoro-3-[5-(6-fluoro-pyridin-3-yl)-1H-pyrrolo[2,3-b]pyridine-3-carbonyl]-phenyl}-amide (P-2155),
N-(4-{3-[2,6-Difluoro-3-(propane-1-sulfonylamino)-benzoyl]-1H-pyrrolo[2,3-b]pyridin-5-yl}-phenyl)-acetamide (P-2161),
Propane-1-sulfonic acid [2,4-difluoro-3-(5-pyrimidin-5-yl-1H-pyrrolo[2,3-b]pyridine-3-carbonyl)-phenyl]-amide (P-2162),
Propane-1-sulfonic acid {2,4-difluoro-3-[5-(4-methanesulfonylamino-phenyl)-1H-pyrrolo[2,3-b]pyridine-3-carbonyl]-phenyl}-amide (P-2165),
Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide (P-2166),
4-{3-[2,6-Difluoro-3-(propane-1-sulfonylamino)-benzoyl]-1H-pyrrolo[2,3-b]pyridin-5-yl}-N-methyl-benzenesulfonamide (P-2167),
N-Cyclopropyl-4-{3-[2,6-difluoro-3-(propane-1-sulfonylamino)-benzoyl]-1H-pyrrolo[2,3-b]pyridin-5-yl}-benzenesulfonamide (P-2168),
Propane-1-sulfonic acid {2,4-difluoro-3-[5-(2-fluoro-6-methyl-pyridin-3-yl)-1H-pyrrolo[2,3-b]pyridine-3-carbonyl]-phenyl}-amide (P-2172),
Propane-1-sulfonic acid {2,4-difluoro-3-[5-(1H-pyrazol-4-yl)-1H-pyrrolo[2,3-b]pyridine-3-carbonyl]-phenyl}-amide (P-2174),
Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide (P-2177),
Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide (P-2178),
5-{3-[2,6-Difluoro-3-(propane-1-sulfonylamino)-benzoyl]-1H-pyrrolo[2,3-b]pyridin-5-yl}-pyridine-2-carboxylic acid methylamide (P-2180),
5-{3-[2,6-Difluoro-3-(propane-1-sulfonylamino)-benzoyl]-1H-pyrrolo[2,3-b]pyridin-5-yl}-pyridine-2-carboxylic acid cyclopropylamide (P-2181),
Propane-1-sulfonic acid {2,4-difluoro-3-[5-(4-methanesulfonyl-phenyl)-1H-pyrrolo[2,3-b]pyridine-3-carbonyl]-phenyl}-amide (P-2183),
Propane-1-sulfonic acid {3-[5-(2,6-dimethoxy-pyridin-3-yl)-1H-pyrrolo[2,3-b]pyridine-3-carbonyl]-2,4-difluoro-phenyl}-amide (P-2184),
4-{3-[2,6-Difluoro-3-(propane-1-sulfonylamino)-benzoyl]-1H-pyrrolo[2,3-b]pyridin-5-yl}-N,N-dimethyl-benzenesulfonamide (P-2185),
Propane-1-sulfonic acid {2,4-difluoro-3-[5-(6-methylsulfanyl-pyridin-3-yl)-1H-pyrrolo[2,3-b]pyridine-3-carbonyl]-phenyl}-amide (P-2187),
Propane-1-sulfonic acid {2,4-difluoro-3-[5-(5-methanesulfonyl-pyridin-3-yl)-1H-pyrrolo[2,3-b]pyridine-3-carbonyl]-phenyl}-amide (P-2188),
Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide (P-2189),
Propane-1-sulfonic acid {3-[5-(1-benzyl-1H-pyrazol-4-yl)-1H-pyrrolo[2,3-b]pyridine-3-carbonyl]-2,4-difluoro-phenyl}-amide (P-2190),
Propane-1-sulfonic acid {2,4-difluoro-3-[5-(2-fluoro-pyridin-4-yl)-1H-pyrrolo[2,3-b]pyridine-3-carbonyl]-phenyl}-amide (P-2192),
N-(5-{3-[2,6-Difluoro-3-(propane-1-sulfonylamino)-benzoyl]-1H-pyrrolo[2,3-b]pyridin-5-yl}-pyridin-2-yl)-acetamide (P-2193),
4-{3-[2,6-Difluoro-3-(propane-1-sulfonylamino)-benzoyl]-1H-pyrrolo[2,3-b]pyridin-5-yl}-benzenesulfonamide (P-2194),
Propane-1-sulfonic acid {3-[5-(2-dimethylamino-pyrimidin-5-yl)-1H-pyrrolo[2,3-b]pyridine-3-carbonyl]-2,4-difluoro-phenyl}-amide (P-2196),
Propane-1-sulfonic acid {2,4-difluoro-3-[5-(2-morpholin-4-yl-pyrimidin-5-yl)-1H-pyrrolo[2,3-b]pyridine-3-carbonyl]-phenyl}-amide (P-2197),
Propane-1-sulfonic acid {3-[5-(2,4-dimethoxy-pyrimidin-5-yl)-1H-pyrrolo[2,3-b]pyridine-3-carbonyl]-2,4-difluoro-phenyl}-amide (P-2199),
Propane-1-sulfonic acid (3-{5-[2-(3-dimethylamino-propoxy)-pyrimidin-5-yl]-1H-pyrrolo[2,3-b]pyridine-3-carbonyl}-2,4-difluoro-phenyl)-amide (P-2203),
Propane-1-sulfonic acid {2,4-difluoro-3-[5-(2-methyl-pyrimidin-5-yl)-1H-pyrrolo[2,3-b]pyridine-3-carbonyl]-phenyl}-amide (P-2211),
Propane-1-sulfonic acid {2,4-difluoro-3-[5-(6-methyl-pyridin-3-yl)-1H-pyrrolo[2,3-b]pyridine-3-carbonyl]-phenyl}-amide (P-2213),
Propane-1-sulfonic acid {3-[5-(6-amino-pyridin-3-yl)-1H-pyrrolo[2,3-b]pyridine-3-carbonyl]-2,4-difluoro-phenyl}-amide (P-2214),
Propane-1-sulfonic acid {3-[5-(4-ethanesulfonyl-phenyl)-1H-pyrrolo[2,3-b]pyridine-3-carbonyl]-2,4-difluoro-phenyl}-amide (P-2218),
Propane-1-sulfonic acid {2,4-difluoro-3-[5-(2-pyrrolidin-1-yl-pyrimidin-5-yl)-1H-pyrrolo[2,3-b]pyridine-3-carbonyl]-phenyl}-amide (P-2219),
5-{3-[2,6-Difluoro-3-(propane-1-sulfonylamino)-benzoyl]-1H-pyrrolo[2,3-b]pyridin-5-yl}-pyridine-2-carboxylic acid amide (P-2220),
Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222),
Propane-1-sulfonic acid (2,4-difluoro-3-{5-[4-(propane-2-sulfonyl)-phenyl]-1H-pyrrolo[2,3-b]pyridine-3-carbonyl}-phenyl)-amide (P-2223),
Propane-1-sulfonic acid {2,4-difluoro-3-[5-(6-propyl-pyridin-3-yl)-1H-pyrrolo[2,3-b]pyridine-3-carbonyl]-phenyl}-amide (P-2224),
Propane-1-sulfonic acid (2,4-difluoro-3-{5-[6-(3-methoxy-propyl)-pyridin-3-yl]-1H-pyrrolo[2,3-b]pyridine-3-carbonyl}-phenyl)-amide (P-2226),
Propane-1-sulfonic acid {2,4-difluoro-3-[5-(3-methanesulfonyl-phenyl)-1H-pyrrolo[2,3-b]pyridine-3-carbonyl]-phenyl}-amide (P-2228), Propane-1-sulfonic acid {3-[5-(6-dimethylamino-pyridin-3-yl)-1H-pyrrolo[2,3-b]pyridine-3-carbonyl]-2,4-difluoro-phenyl}-amide (P-2229),
Propane-1-sulfonic acid {2,4-difluoro-3-[5-(6-pyrrolidin-1-yl-pyridin-3-yl)-1H-pyrrolo[2,3-b]pyridine-3-carbonyl]-phenyl}-amide (P-2231),
Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide (P-2232),
Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide (P-2233),
Propane-1-sulfonic acid {2,4-difluoro-3-[5-(6-hydroxy-pyridin-3-yl)-1H-pyrrolo[2,3-b]pyridine-3-carbonyl]-phenyl}-amide (P-2234),
Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide (P-2235),
Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide (P-2236),
Propane-1-sulfonic acid {2,4-difluoro-3-[5-(3-methoxy-prop-1-ynyl)-1H-pyrrolo[2,3-b]pyridine-3-carbonyl]-phenyl}-amide (P-2239),
Propane-1-sulfonic acid {3-[5-(3-diethylamino-prop-1-ynyl)-1H-pyrrolo[2,3-b]pyridine-3-carbonyl]-2,4-difluoro-phenyl}-amide (P-2241),
Propane-1-sulfonic acid [3-(5-ethynyl-1H-pyrrolo[2,3-b]pyridine-3-carbonyl)-2,4-difluoro-phenyl]-amide (P-2260),
2-Methyl-propane-1-sulfonic acid {2,4-difluoro-3-[5-(1-methyl-1H-pyrazol-4-yl)-1H-pyrrolo[2,3-b]pyridine-3-carbonyl]-phenyl}-amide (P-2299),
Propane-1-sulfonic acid {2-fluoro-3-[5-(2-methoxy-pyrimidin-5-yl)-1H-pyrrolo[2,3-b]pyridine-3-carbonyl]-phenyl}-amide (P-2407),
Propane-1-sulfonic acid {3-[5-(2-dimethylamino-pyrimidin-5-yl)-1H-pyrrolo[2,3-b]pyridine-3-carbonyl]-2-fluoro-phenyl}-amide (P-2408), and
a salt, prodrug, or tautomer thereof.

In reference to compounds as described herein, including compounds of Formula I and all embodiments thereof, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, solid forms thereof, and prodrugs thereof.

In a second aspect, methods are provided for treating any Raf protein kinase mediated disease or condition in an animal subject in need thereof, wherein the method involves administering to the subject an effective amount of any one or more compound(s) as described herein. In one embodiment, the method involves administering to the subject an effective amount of any one or more compound(s) as described herein in combination with one or more other therapies for the disease or condition.

In a third aspect, methods are provided for treating any A-Raf protein kinase mediated disease or condition, including any A-Raf mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a fourth aspect, methods are provided for treating any B-Raf protein kinase mediated disease or condition, including any B-Raf mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a fifth aspect, methods are provided for treating any B-RafV600E mutant protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a sixth aspect, methods are provided for treating any c-Raf-1 protein kinase mediated disease or condition, including any c-Raf-1 mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In a seventh aspect, methods are provided for treating any Ras mutant-activated Raf protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In an eighth aspect, a compound as described herein is a Raf kinase inhibitor and has an $IC_{50}$ of less than 500 nM, less than 100 nM, less than 50 nM, less than 20 nM, less than 10 nM, less than 5 nM, or less than 1 nM as determined in a generally accepted Raf kinase activity assay. In some embodiments, a compound as described herein will have an $IC_{50}$ of less than 500 nm, less than 100 nM, less than 50 nM, less than 20 nM, less than 10 nM, less than 5 nM, or less than 1 nM with respect to A-Raf, B-Raf, c-Raf-1, or B-RafV600E mutant. In some embodiments, a compound as described herein will selectively inhibit one Raf kinase relative to one or more other non-Raf kinases.

In a ninth aspect, a compound as described herein is a pan Raf inhibitor, i.e. inhibits at least each of B-Raf kinase and c-Raf-1 kinase, with an $IC_{50}$ of less than 100 nM, less than 50 nM, less than 20 nM, less than 10 nM, less than 5 nM, or less than 1 nM as determined in each of a generally accepted B-Raf kinase activity assay, and c-Raf-1 kinase activity assay. In some embodiments, the compounds are approximately equipotent on each of B-Raf and c-Raf-1, i.e. the ratio of $IC_{50}$ for either of B-Raf and c-Raf-1 divided by the $IC_{50}$ for the other of B-Raf and c-Raf-1 (e.g. B-Raf $IC_{50}$ divided by c-Raf-1 $IC_{50}$) is in the range of 10 to 0.1, also 5 to 0.2. In some embodiments, the compound is selective relative to other protein kinases, such that the ratio of $IC_{50}$ for another kinase assessed comparably, divided by the $IC_{50}$ for either of B-Raf and c-Raf-1 is >10, also >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the pan Raf inhibitor also inhibits A-Raf kinase. In some embodiments, the compounds are approximately equipotent on each of B-Raf, c-Raf-1, and A-Raf. In some embodiments, the pan Raf inhibitor also inhibits B-Raf V600E mutant kinase. In some embodiments, the compounds are approximately equipotent on each of B-Raf, c-Raf-1, and B-Raf V600E. In some embodiments, the pan Raf inhibitor also inhibits A-Raf and B-Raf V600E mutant kinase. In some embodiments, the compounds are approximately equipotent on each of B-Raf, c-Raf-1, A-Raf and B-Raf V600E. In some embodiments, the pan Raf inhibitor also inhibits tumorigenic cell lines that are driven by Ras mutations, i.e. the compounds inhibit proliferation of a Ras mutation driven tumorigenic cell line with an $IC_{50}$ of less than 1 µM, less than 500 nM, less than 200 nM, or less than 100 nM as determined in a generally accepted cell proliferation assay (alternatively, >20%, >40%, >60%, or >80% inhibition at 1 µM). In some embodiments, the pan Raf inhibitor also inhibits IPC298 cells, i.e. the compounds inhibit proliferation of IPC298 cell line with an $IC_{50}$ of less than 1 µM, less than 500 nM, less than 200 nM, or less than 100 nM as determined in a generally accepted IPC298 cell proliferation assay (alternatively, >20%, >40%, >60%, or >80% inhibition at 1 µM).

In one embodiment of compounds of Formula I, the compound is a pan Raf inhibitor selected from the group consisting of:

N-[3-(5-Chloro-1H-pyrrolo[2,3-b]pyridine-3-carbonyl)-2,4-difluoro-phenyl]-2,5-difluoro-benzenesulfonamide (P-2002), N-[3-(5-Chloro-1H-pyrrolo[2,3-b]pyridine-3-carbonyl)-2,4-difluoro-phenyl]-2,6-difluoro-benzenesulfonamide (P-2003), N-[2,4-Difluoro-3-(5-methoxy-1H-pyrrolo[2,3-b]pyridine-3-carbonyl)-phenyl]-2-fluoro-benzenesulfonamide (P-2009), N-[2,4-Difluoro-3-(5-methoxy-1H-pyrrolo[2,3-b]pyridine-3-carbonyl)-phenyl]-2,5-difluoro-benzenesulfonamide (P-2010), N-[3-(5-Cyano-1H-pyrrolo[2,3-b]pyridine-3-carbonyl)-2,4-difluoro-phenyl]-2-fluoro-benzenesulfonamide (P-2011), N-[2,4-Difluoro-3-(5-methyl-1H-pyrrolo[2,3-b]pyridine-3-carbonyl)-phenyl]-2-fluoro-benzenesulfonamide (P-2014), N-[2,4-Difluoro-3-(5-methyl-1H-pyrrolo[2,3-b]pyridine-3-carbonyl)-phenyl]-2,5-difluoro-benzenesulfonamide (P-2015), N-[2,4-Difluoro-3-(5-methyl-1H-pyrrolo[2,3-b]pyridine-3-carbonyl)-phenyl]-3-fluoro-benzenesulfonamide (P-2016), N-[3-(4-Chloro-1H-pyrrolo[2,3-b]pyridine-3-carbonyl)-2,4-difluoro-phenyl]-2-fluoro-benzenesulfonamide (P-2017), N-[3-(4-Chloro-1H-pyrrolo[2,3-b]pyridine-3-carbonyl)-2,4-difluoro-phenyl]-2,5-difluoro-benzenesulfonamide (P-2018), N-[3-(4-Chloro-1H-pyrrolo[2,3-b]pyridine-3-carbonyl)-2,4-difluoro-phenyl]-3-fluoro-benzenesulfonamide (P-2019), N-[3-(4-Cyano-1H-pyrrolo[2,3-b]pyridine-3-carbonyl)-2,4-difluoro-phenyl]-2-fluoro-benzenesulfonamide (P-2020), N-[2,4-Difluoro-3-(4-methoxy-1H-pyrrolo[2,3-b]pyridine-3-carbonyl)-phenyl]-2-fluoro-benzenesulfonamide (P-2021), N-[2,4-Difluoro-3-(4-methoxy-1H-pyrrolo[2,3-b]pyridine-3-carbonyl)-phenyl]-2,5-difluoro-benzenesulfonamide (P-2022), N-[2,4-Difluoro-3-(4-methoxy-1H-pyrrolo[2,3-b]pyridine-3-carbonyl)-phenyl]-3-fluoro-benzenesulfonamide (P-2023), N-[2,4-Difluoro-3-(5-methyl-1H-pyrrolo[2,3-b]pyridine-3-carbonyl)-phenyl]-2,6-difluoro-benzenesulfonamide (P-2024), N-[3-(5-Cyano-1H-pyrrolo[2,3-b]pyridine-3-carbonyl)-2,4-difluoro-phenyl]-2,6-difluoro-benzenesulfonamide (P-2029), N-[3-(4-Chloro-1H-pyrrolo[2,3-b]pyridine-3-carbonyl)-2,4-difluoro-phenyl]-2,6-difluoro-benzenesulfonamide (P-2033), N-[3-(4-Cyano-1H-pyrrolo[2,3-b]pyridine-3-carbonyl)-2,4-difluoro-phenyl]-2,5-difluoro-benzenesulfonamide (P-2036), N-[3-(4-Cyano-1H-pyrrolo[2,3-b]pyridine-3-carbonyl)-2,4-difluoro-phenyl]-2,6-difluoro-benzenesulfonamide (P-2037), N-[3-(4-Cyano-1H-pyrrolo[2,3-b]pyridine-3-carbonyl)-2,4-difluoro-phenyl]-3-fluoro-benzenesulfonamide (P-2039), N-{2,4-Difluoro-3-[5-(2-methoxy-pyrimidin-5-yl)-1H-pyrrolo[2,3-b]pyridine-3-carbonyl]-phenyl}-2-fluoro-benzenesulfonamide (P-2041), N-{2,4-Difluoro-3-[5-(2-methoxy-pyrimidin-5-yl)-1H-pyrrolo[2,3-b]pyridine-3-carbonyl]-phenyl}-2,5-difluoro-benzenesulfonamide (P-2042), N-{2,4-Difluoro-3-[5-(2-methoxy-pyrimidin-5-yl)-1H-pyrrolo[2,3-b]pyridine-3-carbonyl]-phenyl}-2,6-difluoro-benzenesulfonamide (P-2043), N-{2,4-Difluoro-3-[5-(2-methoxy-pyrimidin-5-yl)-1H-pyrrolo[2,3-b]pyridine-3-carbonyl]-phenyl}-3-fluoro-benzenesulfonamide (P-2045), N-[3-(5-Cyano-1H-pyrrolo[2,3-b]pyridine-3-carbonyl)-2,4-difluoro-phenyl]-benzenesulfonamide (P-2046), N-[3-(5-Cyano-1H-pyrrolo[2,3-b]pyridine-3-carbonyl)-2-fluoro-phenyl]-2-fluoro-benzenesulfonamide (P-2051), N-[3-(5-Cyano-1H-pyrrolo[2,3-b]pyridine-3-carbonyl)-2-fluoro-phenyl]-2,5-difluoro-benzenesulfonamide (P-2052), N-[3-(5-Cyano-1H-pyrrolo[2,3-b]pyridine-3-carbonyl)-2-fluoro-phenyl]-3-fluoro-benzenesulfonamide (P-2053), N-[3-(5-Cyano-1H-pyrrolo[2,3-b]pyridine-3-carbonyl)-2-fluoro-phenyl]-2,6-difluoro-benzenesulfonamide (P-2054), N-[3-(5-Cyano-1H-pyrrolo[2,3-b]pyridine-3-carbonyl)-2-fluoro-phenyl]-benzenesulfonamide (P-2056), Pyridine-3-sulfonic acid [2,4-difluoro-3-(5-methyl-1H-pyrrolo[2,3-b]pyridine-3-carbonyl)-phenyl]-amide (P-2069), Pyridine-3-sulfonic acid [3-(5-chloro-1H-pyrrolo[2,3-b]pyridine-3-carbonyl)-2,4-difluoro-phenyl]-amide (P-2071), Pyridine-3-sulfonic acid [3-(5-cyano-1H-pyrrolo[2,3-b]pyridine-3-carbonyl)-2,4-difluoro-phenyl]-amide (P-2072), Pyridine-3-sulfonic acid [2,4-difluoro-3-(4-methoxy-1H-pyrrolo[2,3-b]pyridine-3-carbonyl)-phenyl]-amide (P-2073), Pyridine-3-sulfonic acid [3-(4-chloro-1H-pyrrolo[2,3-b]pyridine-3-carbonyl)-2,4-difluoro-phenyl]-amide (P-2074), Pyridine-3-sulfonic acid [3-(4-cyano-1H-pyrrolo[2,3-b]pyridine-3-carbonyl)-2,4-difluoro-phenyl]-amide (P-2077), Pyridine-3-sulfonic acid [3-(5-cyano-1H-pyrrolo[2,3-b]pyridine-3-carbonyl)-2-fluoro-phenyl]-amide (P-2086), 5-{3-[2,6-Difluoro-3-(propane-1-sulfonylamino)-benzoyl]-1H-pyrrolo[2,3-b]pyridin-5-yl}-pyridine-2-carboxylic acid ethylamide (P-2151), Propane-1-sulfonic acid {3-[5-(6-chloro-pyridin-3-yl)-1H-pyrrolo[2,3-b]pyridine-3-carbonyl]-2,4-difluoro-phenyl}-amide (P-2154), Propane-1-sulfonic acid {2,4-difluoro-3-[5-(6-fluoro-pyridin-3-yl)-1H-pyrrolo[2,3-b]pyridine-3-carbonyl]-phenyl}-amide (P-2155), N-(4-{3-[2,6-Difluoro-3-(propane-1-sulfonylamino)-benzoyl]-1H-pyrrolo[2,3-b]pyridin-5-yl}-phenyl)-acetamide (P-2161), Propane-1-sulfonic acid [2,4-difluoro-3-(5-pyrimidin-5-yl-1H-pyrrolo[2,3-b]pyridine-3-carbonyl)-phenyl]-amide (P-2162), Propane-1-sulfonic acid {2,4-difluoro-3-[5-(4-methanesulfonylamino-phenyl)-1H-pyrrolo[2,3-b]pyridine-3-carbonyl]-phenyl}-amide (P-2165), Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide (P-2166), 4-{3-[2,6-Difluoro-3-(propane-1-sulfonylamino)-benzoyl]-1H-pyrrolo[2,3-b]pyridin-5-yl}-N-methyl-benzenesulfonamide (P-2167), N-Cyclopropyl-4-{3-[2,6-difluoro-3-(propane-1-sulfonylamino)-benzoyl]-1H-pyrrolo[2,3-b]pyridin-5-yl}-benzenesulfonamide (P-2168), Propane-1-sulfonic acid {2,4-difluoro-3-[5-(2-fluoro-6-methyl-pyridin-3-yl)-1H-pyrrolo[2,3-b]pyridine-3-carbonyl]-phenyl}-amide (P-2172), Propane-1-sulfonic acid {2,4-difluoro-3-[5-(1H-pyrazol-4-yl)-1H-pyrrolo[2,3-b]pyridine-3-carbonyl]-phenyl}-amide (P-2174), Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide (P-2177), Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide (P-2178), 5-{3-[2,6-Difluoro-3-(propane-1-sulfonylamino)-benzoyl]-1H-pyrrolo[2,3-b]pyridin-5-yl}-pyridine-2-carboxylic acid methylamide (P-2180), 5-{3-[2,6-Difluoro-3-(propane-1-sulfonylamino)-benzoyl]-1H-pyrrolo[2,3-b]pyridin-5-yl}-pyridine-2-carboxylic acid cyclopropylamide (P-2181), Propane-1-sulfonic acid {2,4-difluoro-3-[5-(4-methanesulfonyl-phenyl)-1H-pyrrolo[2,3-b]pyridine-3-carbonyl]-phenyl}-amide (P-2183), Propane-1-sulfonic acid {3-[5-(2,6-dimethoxy-pyridin-3-yl)-1H-pyrrolo[2,3-b]pyridine-3-carbonyl]-2,4-difluoro-phenyl}-amide (P-2184), 4-{3-[2,6-Difluoro-3-(propane-1-sulfonylamino)-benzoyl]-1H-pyrrolo[2,3-b]pyridin-5-yl}-N,N-dimethyl-benzenesulfonamide (P-2185), Propane-1-sulfonic acid {2,4-difluoro-3-[5-(6-methylsulfanyl-pyridin-3-yl)-1H-pyrrolo[2,3-b]pyridine-3-carbonyl]-phenyl}-amide (P-2187), Propane-1-sulfonic acid {2,4-difluoro-3-[5-(5-methanesulfonyl-pyridin-3-yl)-1H-pyrrolo[2,3-b]pyridine-3-carbonyl]-phenyl}-amide (P-2188), Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide (P-2189), Propane-1-sulfonic acid {3-[5-(1-benzyl-1H-pyrazol-4-yl)-1H-pyrrolo[2,3-b]pyridine-3-carbonyl]-2,4-difluoro-phenyl}-amide (P-2190), Propane-1-sulfonic acid {2,4-difluoro-3-[5-(2-fluoro-pyridin-4-yl)-1H-pyrrolo[2,3-b]pyridine-3-carbonyl]-phenyl}-amide (P-2192), N-(5-{3-[2,6-Difluoro-3-(propane-1-sulfonylamino)-benzoyl]-1H-pyrrolo[2,3-b]pyridin-5-yl}-pyridin-2-yl)-acetamide (P-2193), 4-{3-[2,6-Difluoro-3-(propane-1-sulfonylamino)-benzoyl]-1H-pyrrolo[2,3-b]pyridin-5-yl}-benzenesulfonamide (P-2194), Propane-1-sulfonic acid {3-[5-(2-dimethylamino-pyrimidin-5-yl)-1H-pyrrolo[2,3-b]pyridine-3-carbonyl]-2,4-difluoro-phenyl}-amide (P-2196), Propane-1-sulfonic acid {2,4-difluoro-3-[5-(2-morpholin-4-yl-pyrimidin-5-yl)-1H-pyrrolo[2,3-b]pyridine-3-carbonyl]-phenyl}-amide (P-2197), Propane-1-sulfonic acid {3-[5-(2,4-dimethoxy-pyrimidin-5-yl)-1H-pyrrolo[2,3-b]pyridine-3-carbonyl]-2,4-difluoro-phenyl}-amide (P-2199), Propane-1-sulfonic acid (3-{5-[2-(3-dimethylamino-propoxy)-pyrimidin-5-yl]-1H-pyrrolo[2,3-b]pyridine-3-carbonyl}-2,4-difluoro-phenyl)-amide (P-2203), Propane-1-sulfonic acid {2,4-difluoro-3-[5-(2-methyl-pyrimidin-5-yl)-1H-pyrrolo[2,3-b]pyridine-3-carbonyl]-phenyl}-amide (P-2211), Propane-1-sulfonic acid {2,4-difluoro-3-[5-(6-methyl-pyridin-3-yl)-1H-pyrrolo[2,3-b]pyridine-3-carbonyl]-phenyl}-amide (P-2213), Propane-1-sulfonic acid {3-[5-(6-amino-pyridin-3-yl)-1H-pyrrolo[2,3-b]pyridine-3-carbonyl]-2,4-difluoro-phenyl}-amide (P-2214), Propane-1-sulfonic acid {3-[5-(4-ethanesulfonyl-phenyl)-1H-pyrrolo[2,3-b]pyridine-3-carbonyl]-2,4-difluoro-phenyl}-amide (P-2218), Propane-1-sulfonic acid {2,4-difluoro-3-[5-(2-pyrrolidin-1-yl-pyrimidin-5-yl)-1H-pyrrolo[2,3-b]pyridine-3-carbonyl]-phenyl}-amide (P-2219), 5-{3-[2,6-Difluoro-3-(propane-1-sulfonylamino)-benzoyl]-1H-pyrrolo[2,3-b]pyridin-5-yl}-pyridine-2-carboxylic acid amide (P-2220), Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222), Propane-1-sulfonic acid (2,4-difluoro-3-{5-[4-(propane-2-sulfonyl)-phenyl]-1H-pyrrolo[2,3-b]pyridine-3-carbonyl}-phenyl)-amide (P-2223), Propane-1-sulfonic acid {2,4-difluoro-3-[5-(6-propyl-pyridin-3-yl)-1H-pyrrolo[2,3-b]pyridine-3-carbonyl]-phenyl}-amide (P-2224), Propane-1-sulfonic acid (2,4-difluoro-3-{5-[6-(3-methoxy-propyl)-pyridin-3-yl]-1H-pyrrolo[2,3-b]pyridine-3-carbonyl}-phenyl)-amide (P-2226), Propane-1-sulfonic acid {2,4-difluoro-3-[5-(3-methanesulfonyl-phenyl)-1H-pyrrolo[2,3-b]pyridine-3-carbonyl]-phenyl}-amide (P-2228), Propane-1-sulfonic acid {3-[5-(6-dimethylamino-pyridin-3-yl)-1H-pyrrolo[2,3-b]pyridine-3-carbonyl]-2,4-difluoro-phenyl}-amide (P-2229), Propane-1-sulfonic acid {2,4-difluoro-3-[5-(6-pyrrolidin-1-yl-pyridin-3-yl)-1H-pyrrolo[2,3-b]pyridine-3-carbonyl]-phenyl}-amide (P-2231), Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide (P-2232), Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide (P-2233), Propane-1-sulfonic acid {2,4-difluoro-3-[5-(6-hydroxy-pyridin-3-yl)-1H-pyrrolo[2,3-b]pyridine-3-carbonyl]-phenyl}-amide (P-2234), Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide (P-2235), Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide (P-2236), Propane-1-sulfonic acid {2,4-difluoro-3-[5-(3-methoxy-prop-1-ynyl)-1H-pyrrolo[2,3-b]pyridine-3-carbonyl]-phenyl}-amide (P-2239), Propane-1-sulfonic acid {3-[5-(3-diethylamino-prop-1-ynyl)-1H-pyrrolo[2,3-b]pyridine-3-carbonyl]-2,4-difluoro-phenyl}-amide (P-2241), Propane-1-sulfonic acid [3-(5-ethynyl-1H-pyrrolo[2,3-b]pyridine-3-carbonyl)-2,4-difluoro-phenyl]-amide (P-2260), 2-Methyl-propane-1-sulfonic acid {2,4-difluoro-3-[5-(1-methyl-1H-pyrazol-4-yl)-1H-pyrrolo[2,3-b]pyridine-3-carbonyl]-phenyl}-amide (P-2299), Propane-1-sulfonic acid {2-fluoro-3-[5-(2-methoxy-pyrimidin-5-yl)-1H-pyrrolo[2,3-b]pyridine-3-carbonyl]-phenyl}-amide (P-2407), Propane-1-sulfonic acid {3-[5-(2-dimethylamino-pyrimidin-5-yl)-1H-pyrrolo[2,3-b]pyridine-3-carbonyl]-2-fluoro-phenyl}-amide (P-2408), and a salt, prodrug, or tautomer thereof.

In one embodiment of compounds of Formula I, the compound is a pan Raf inhibitor selected from the group consisting of:

N-[3-(5-Chloro-1H-pyrrolo[2,3-b]pyridine-3-carbonyl)-2,4-difluoro-phenyl]-2,5-difluoro-benzenesulfonamide (P-2002), N-[3-(4-Cyano-1H-pyrrolo[2,3-b]pyridine-3-carbonyl)-2,4-difluoro-phenyl]-2-fluoro-benzenesulfonamide (P-2020), N-[3-(4-Cyano-1H-pyrrolo[2,3-b]pyridine-3-carbonyl)-2,4-difluoro-phenyl]-2,5-difluoro-benzenesulfonamide (P-2036), N-{2,4-Difluoro-3-[5-(2-methoxy-pyrimidin-5-yl)-1H-pyrrolo[2,3-b]pyridine-3-carbonyl]-phenyl}-2-fluoro-benzenesulfonamide (P-2041), N-{2,4-Difluoro-3-[5-(2-methoxy-pyrimidin-5-yl)-1H-pyrrolo[2,3-b]pyridine-3-carbonyl]-phenyl}-2,5-difluoro-benzenesulfonamide (P-2042), N-{2,4-Difluoro-3-[5-(2-methoxy-pyrimidin-5-yl)-1H-pyrrolo[2,3-b]pyridine-3-carbonyl]-phenyl}-2,6-difluoro-benzenesulfonamide (P-2043), N-[3-(5-Cyano-1H-pyrrolo[2,3-b]pyridine-3-carbonyl)-2,4-difluoro-phenyl]-benzenesulfonamide (P-2046), N-[3-(5-Cyano-1H-pyrrolo[2,3-b]pyridine-3-carbonyl)-2-fluoro-phenyl]-3-fluoro-benzenesulfonamide (P-2053), Pyridine-3-sulfonic acid [2,4-difluoro-3-(5-methyl-1H-pyrrolo[2,3-b]pyridine-3-carbonyl)-phenyl]-amide (P-2069), Pyridine-3-sulfonic acid [3-(5-chloro-1H-pyrrolo[2,3-b]pyridine-3-carbonyl)-2,4-difluoro-phenyl]-amide (P-2071), Pyridine-3-sulfonic acid [3-(4-cyano-1H-pyrrolo[2,3-b]pyridine-3-carbonyl)-2,4-difluoro-phenyl]-amide (P-2077), Pyridine-3-sulfonic acid [3-(5-cyano-1H-pyrrolo[2,3-b]pyridine-3-carbonyl)-2-fluoro-phenyl]-amide (P-2086), 5-{3-[2,6-Difluoro-3-(propane-1-sulfonylamino)-benzoyl]-1H-pyrrolo[2,3-b]pyridin-5-yl}-pyridine-2-carboxylic acid ethylamide (P-2151), Propane-1-sulfonic acid {3-[5-(6-chloro-pyridin-3-yl)-1H-pyrrolo[2,3-b]pyridine-3-carbonyl]-2,4-difluoro-phenyl}-amide (P-2154), Propane-1-sulfonic acid {2,4-difluoro-3-[5-(6-fluoro-pyridin-3-yl)-1H-pyrrolo[2,3-b]pyridine-3-carbonyl]-phenyl}-amide (P-2155), N-(4-{3-[2,6-Difluoro-3-(propane-1-sulfonylamino)-benzoyl]-1H-pyrrolo[2,3-b]pyridin-5-yl}-phenyl)-acetamide (P-2161), Propane-1-sulfonic acid {2,4-difluoro-3-[5-(4-methanesulfonylamino-phenyl)-1H-pyrrolo[2,3-b]pyridine-3-carbonyl]-phenyl}-amide (P-2165), Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide (P-2166), 4-{3-[2,6-Difluoro-3-(propane-1-sulfonylamino)-benzoyl]-1H-pyrrolo[2,3-b]pyridin-5-yl}-N-methyl-benzenesulfonamide (P-2167), N-Cyclopropyl-4-{3-[2,6-difluoro-3-(propane-1-sulfonylamino)-benzoyl]-1H-pyrrolo[2,3-b]pyridin-5-yl}-benzenesulfonamide (P-2168), Propane-1-sulfonic acid {2,4-difluoro-3-[5-(1H-pyrazol-4-yl)-1H-pyrrolo[2,3-b]pyridine-3-carbonyl]-phenyl}-amide (P-2174), Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide (P-2177), Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide (P-2178), 5-{3-[2,6-Difluoro-3-(propane-1-sulfonylamino)-benzoyl]-1H-pyrrolo[2,3-b]pyridin-5-yl}-pyridine-2-carboxylic acid methylamide (P-2180), 5-{3-[2,6-Difluoro-3-(propane-1-sulfonylamino)-benzoyl]-1H-pyrrolo[2,3-b]pyridin-5-yl}-pyridine-2-carboxylic acid cyclopropylamide (P-2181), Propane-1-sulfonic acid {2,4-difluoro-3-[5-(4-methanesulfonyl-phenyl)-1H-pyrrolo[2,3-b]pyridine-3-carbonyl]-phenyl}-amide (P-2183), 4-{3-[2,6-Difluoro-3-(propane-1-sulfonylamino)-benzoyl]-1H-pyrrolo[2,3-b]pyridin-5-yl}-N,N-dimethyl-benzenesulfonamide (P-2185), Propane-1-sulfonic acid {2,4-difluoro-3-[5-(6-methylsulfanyl-pyridin-3-yl)-1H-pyrrolo[2,3-b]pyridine-3-carbonyl]-phenyl}-amide (P-2187), Propane-1-sulfonic acid {2,4-difluoro-3-[5-(5-methanesulfonyl-pyridin-3-yl)-1H-pyrrolo[2,3-b]pyridine-3-carbonyl]-phenyl}-amide (P-2188), Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide (P-2189), Propane-1-sulfonic acid {3-[5-(1-benzyl-1H-pyrazol-4-yl)-1H-pyrrolo[2,3-b]pyridine-3-carbonyl]-2,4-difluoro-phenyl}-amide (P-2190), Propane-1-sulfonic acid {2,4-difluoro-3-[5-(2-fluoro-pyridin-4-yl)-1H-pyrrolo[2,3-b]pyridine-3-carbonyl]-phenyl}-amide (P-2192), N-(5-{3-[2,6-Difluoro-3-(propane-1-sulfonylamino)-benzoyl]-1H-pyrrolo[2,3-b]pyridin-5-yl}-pyridin-2-yl)-acetamide (P-2193), 4-{3-[2,6-Difluoro-3-(propane-1-sulfonylamino)-benzoyl]-1H-pyrrolo[2,3-b]pyridin-5-yl}-benzenesulfonamide (P-2194), Propane-1-sulfonic acid {3-[5-(2-dimethylamino-pyrimidin-5-yl)-1H-pyrrolo[2,3-b]pyridine-3-carbonyl]-2,4-difluoro-phenyl}-amide (P-2196), Propane-1-sulfonic acid {2,4-difluoro-3-[5-(2-morpholin-4-yl-pyrimidin-5-yl)-1H-pyrrolo[2,3-b]pyridine-3-carbonyl]-phenyl}-amide (P-2197), Propane-1-sulfonic acid (3-{5-[2-(3-dimethylamino-propoxy)-pyrimidin-5-yl]-1H-pyrrolo[2,3-b]pyridine-3-carbonyl}-2,4-difluoro-phenyl)-amide (P-2203), Propane-1-sulfonic acid {2,4-difluoro-3-[5-(2-methyl-pyrimidin-5-yl)-1H-pyrrolo[2,3-b]pyridine-3-carbonyl]-phenyl}-amide (P-2211), Propane-1-sulfonic acid {2,4-difluoro-3-[5-(6-methyl-pyridin-3-yl)-1H-pyrrolo[2,3-b]pyridine-3-carbonyl]-phenyl}-amide (P-2213),
Propane-1-sulfonic acid {3-[5-(6-amino-pyridin-3-yl)-1H-pyrrolo[2,3-b]pyridine-3-carbonyl]-2,4-difluoro-phenyl}-amide (P-2214),
Propane-1-sulfonic acid {3-[5-(4-ethanesulfonyl-phenyl)-1H-pyrrolo[2,3-b]pyridine-3-carbonyl]-2,4-difluoro-phenyl}-amide (P-2218),
Propane-1-sulfonic acid {2,4-difluoro-3-[5-(2-pyrrolidin-1-yl-pyrimidin-5-yl)-1H-pyrrolo[2,3-b]pyridine-3-carbonyl]-phenyl}-amide (P-2219),
Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222),
Propane-1-sulfonic acid (2,4-difluoro-3-{5-[4-(propane-2-sulfonyl)-phenyl]-1H-pyrrolo[2,3-b]pyridine-3-carbonyl}-phenyl)-amide (P-2223),
Propane-1-sulfonic acid {2,4-difluoro-3-[5-(6-propyl-pyridin-3-yl)-1H-pyrrolo[2,3-b]pyridine-3-carbonyl]-phenyl}-amide (P-2224),
Propane-1-sulfonic acid (2,4-difluoro-3-{5-[6-(3-methoxypropyl)-pyridin-3-yl]-1H-pyrrolo[2,3-b]pyridine-3-carbonyl}-phenyl)-amide (P-2226),
Propane-1-sulfonic acid {2,4-difluoro-3-[5-(3-methanesulfonyl-phenyl)-1H-pyrrolo[2,3-b]pyridine-3-carbonyl]-phenyl}-amide (P-2228),
Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide (P-2232),
Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide (P-2233),
Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide (P-2235),
Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide (P-2236),
Propane-1-sulfonic acid {2,4-difluoro-3-[5-(3-methoxyprop-1-ynyl)-1H-pyrrolo[2,3-b]pyridine-3-carbonyl]-phenyl}-amide (P-2239),
Propane-1-sulfonic acid [3-(5-ethynyl-1H-pyrrolo[2,3-b]pyridine-3-carbonyl)-2,4-difluoro-phenyl]-amide (P-2260),
2-Methyl-propane-1-sulfonic acid {2,4-difluoro-3-[5-(1-methyl-1H-pyrazol-4-yl)-1H-pyrrolo[2,3-b]pyridine-3-carbonyl]-phenyl}-amide (P-2299), and
a salt, prodrug, or tautomer thereof.

In one embodiment of compounds of Formula I, the compound is a pan Raf inhibitor selected from the group consisting of:

N-[3-(5-Chloro-1H-pyrrolo[2,3-b]pyridine-3-carbonyl)-2,4-difluoro-phenyl]-2,5-difluoro-benzenesulfonamide (P-2002),
N-[3-(4-Cyano-1H-pyrrolo[2,3-b]pyridine-3-carbonyl)-2,4-difluoro-phenyl]-2,5-difluoro-benzenesulfonamide (P-2036),
N-{2,4-Difluoro-3-[5-(2-methoxy-pyrimidin-5-yl)-1H-pyrrolo[2,3-b]pyridine-3-carbonyl]-phenyl}-2-fluoro-benzenesulfonamide (P-2041),
N-{2,4-Difluoro-3-[5-(2-methoxy-pyrimidin-5-yl)-1H-pyrrolo[2,3-b]pyridine-3-carbonyl]-phenyl}-2,5-difluoro-benzenesulfonamide (P-2042),
N-{2,4-Difluoro-3-[5-(2-methoxy-pyrimidin-5-yl)-1H-pyrrolo[2,3-b]pyridine-3-carbonyl]-phenyl}-2,6-difluoro-benzenesulfonamide (P-2043),
N-[3-(5-Cyano-1H-pyrrolo[2,3-b]pyridine-3-carbonyl)-2,4-difluoro-phenyl]-benzenesulfonamide (P-2046),
N-[3-(5-Cyano-1H-pyrrolo[2,3-b]pyridine-3-carbonyl)-2-fluoro-phenyl]-3-fluoro-benzenesulfonamide (P-2053),
Pyridine-3-sulfonic acid [2,4-difluoro-3-(5-methyl-1H-pyrrolo[2,3-b]pyridine-3-carbonyl)-phenyl]-amide (P-2069),
Pyridine-3-sulfonic acid [3-(5-chloro-1H-pyrrolo[2,3-b]pyridine-3-carbonyl)-2,4-difluoro-phenyl]-amide (P-2071),
5-{3-[2,6-Difluoro-3-(propane-1-sulfonylamino)-benzoyl]-1H-pyrrolo[2,3-b]pyridin-5-yl}-pyridine-2-carboxylic acid ethylamide (P-2151),
Propane-1-sulfonic acid {2,4-difluoro-3-[5-(6-fluoro-pyridin-3-yl)-1H-pyrrolo[2,3-b]pyridine-3-carbonyl]-phenyl}-amide (P-2155),
Propane-1-sulfonic acid {2,4-difluoro-3-[5-(4-methanesulfonylamino-phenyl)-1H-pyrrolo[2,3-b]pyridine-3-carbonyl]-phenyl}-amide (P-2165),
Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide (P-2166),
4-{3-[2,6-Difluoro-3-(propane-1-sulfonylamino)-benzoyl]-1H-pyrrolo[2,3-b]pyridin-5-yl}-N-methyl-benzenesulfonamide (P-2167),
N-Cyclopropyl-4-{3-[2,6-difluoro-3-(propane-1-sulfonylamino)-benzoyl]-1H-pyrrolo[2,3-b]pyridin-5-yl}-benzenesulfonamide (P-2168),
Propane-1-sulfonic acid {2,4-difluoro-3-[5-(1H-pyrazol-4-yl)-1H-pyrrolo[2,3-b]pyridine-3-carbonyl]-phenyl}-amide (P-2174),
Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide (P-2177),
Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide (P-2178),
Propane-1-sulfonic acid {2,4-difluoro-3-[5-(4-methanesulfonyl-phenyl)-1H-pyrrolo[2,3-b]pyridine-3-carbonyl]-phenyl}-amide (P-2183),
4-{3-[2,6-Difluoro-3-(propane-1-sulfonylamino)-benzoyl]-1H-pyrrolo[2,3-b]pyridin-5-yl}-N,N-dimethyl-benzenesulfonamide (P-2185),
Propane-1-sulfonic acid {2,4-difluoro-3-[5-(6-methylsulfanyl-pyridin-3-yl)-1H-pyrrolo[2,3-b]pyridine-3-carbonyl]-phenyl}-amide (P-2187),
Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide (P-2189),
Propane-1-sulfonic acid {3-[5-(1-benzyl-1H-pyrazol-4-yl)-1H-pyrrolo[2,3-b]pyridine-3-carbonyl]-2,4-difluoro-phenyl}-amide (P-2190),
N-(5-{3-[2,6-Difluoro-3-(propane-1-sulfonylamino)-benzoyl]-1H-pyrrolo[2,3-b]pyridin-5-yl}-pyridin-2-yl)-acetamide (P-2193),
Propane-1-sulfonic acid {3-[5-(2-dimethylamino-pyrimidin-5-yl)-1H-pyrrolo[2,3-b]pyridine-3-carbonyl]-2,4-difluoro-phenyl}-amide (P-2196),
Propane-1-sulfonic acid {2,4-difluoro-3-[5-(2-methyl-pyrimidin-5-yl)-1H-pyrrolo[2,3-b]pyridine-3-carbonyl]-phenyl}-amide (P-2211),
Propane-1-sulfonic acid {2,4-difluoro-3-[5-(6-methyl-pyridin-3-yl)-1H-pyrrolo[2,3-b]pyridine-3-carbonyl]-phenyl}-amide (P-2213),
Propane-1-sulfonic acid {3-[5-(6-amino-pyridin-3-yl-1H-pyrrolo[2,3-b]pyridine-3-carbonyl]-2,4-difluoro-phenyl}-amide (P-2214), Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222),
Propane-1-sulfonic acid {2,4-difluoro-3-[5-(6-propyl-pyridin-3-yl)-1H-pyrrolo[2,3-b]pyridine-3-carbonyl]-phenyl}-amide (P-2224),
Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide (P-2232),
Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide (P-2233),
Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide (P-2235),
Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide (P-2236),
Propane-1-sulfonic acid [3-(5-ethynyl-1H-pyrrolo[2,3-b]pyridine-3-carbonyl)-2,4-difluoro-phenyl]-amide (P-2260), and
a salt, prodrug, or tautomer thereof.

In one embodiment of compounds of Formula I, the compound is a pan Raf inhibitor selected from the group consisting of:
5-{3-[2,6-Difluoro-3-(propane-1-sulfonylamino)-benzoyl]-1H-pyrrolo[2,3-b]pyridin-5-yl}-pyridine-2-carboxylic acid ethylamide (P-2151),
Propane-1-sulfonic acid {3-[5-(6-chloro-pyridin-3-yl)-1H-pyrrolo[2,3-b]pyridine-3-carbonyl]-2,4-difluoro-phenyl}-amide (P-2154),
Propane-1-sulfonic acid {2,4-difluoro-3-[5-(6-fluoro-pyridin-3-yl)-1H-pyrrolo[2,3-b]pyridine-3-carbonyl]-phenyl}-amide (P-2155),
Propane-1-sulfonic acid {2,4-difluoro-3-[5-(2-fluoro-6-methyl-pyridin-3-yl)-1H-pyrrolo[2,3-b]pyridine-3-carbonyl]-phenyl}-amide (P-2172),
Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide (P-2178),
5-{3-[2,6-Difluoro-3-(propane-1-sulfonylamino)-benzoyl]-1H-pyrrolo[2,3-b]pyridin-5-yl}-pyridine-2-carboxylic acid methylamide (P-2180),
5-{3-[2,6-Difluoro-3-(propane-1-sulfonylamino)-benzoyl]-1H-pyrrolo[2,3-b]pyridin-5-yl}-pyridine-2-carboxylic acid cyclopropylamide (P-2181),
Propane-1-sulfonic acid {3-[5-(2,6-dimethoxy-pyridin-3-yl)-1H-pyrrolo[2,3-b]pyridine-3-carbonyl]-2,4-difluoro-phenyl}-amide (P-2184),
Propane-1-sulfonic acid {2,4-difluoro-3-[5-(6-methylsulfanyl-pyridin-3-yl)-1H-pyrrolo[2,3-b]pyridine-3-carbonyl]-phenyl}-amide (P-2187),
Propane-1-sulfonic acid {2,4-difluoro-3-[5-(5-methanesulfonyl-pyridin-3-yl)-1H-pyrrolo[2,3-b]pyridine-3-carbonyl]-phenyl}-amide (P-2188),
N-(5-{3-[2,6-Difluoro-3-(propane-1-sulfonylamino)-benzoyl]-1H-pyrrolo[2,3-b]pyridin-5-yl}-pyridin-2-yl)-acetamide (P-2193),
Propane-1-sulfonic acid {2,4-difluoro-3-[5-(6-methyl-pyridin-3-yl)-1H-pyrrolo[2,3-b]pyridine-3-carbonyl]-phenyl}-amide (P-2213),
Propane-1-sulfonic acid {3-[5-(6-amino-pyridin-3-yl)-1H-pyrrolo[2,3-b]pyridine-3-carbonyl]-2,4-difluoro-phenyl}-amide (P-2214),
5-{3-[2,6-Difluoro-3-(propane-1-sulfonylamino)-benzoyl]-1H-pyrrolo[2,3-b]pyridin-5-yl}-pyridine-2-carboxylic acid amide (P-2220),
Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222),
Propane-1-sulfonic acid {2,4-difluoro-3-[5-(6-propyl-pyridin-3-yl)-1H-pyrrolo[2,3-b]pyridine-3-carbonyl]-phenyl}-amide (P-2224),
Propane-1-sulfonic acid (2,4-difluoro-3-{5-[6-(3-methoxy-propyl)-pyridin-3-yl]-1H-pyrrolo[2,3-b]pyridine-3-carbonyl}-phenyl)-amide (P-2226),
Propane-1-sulfonic acid {3-[5-(6-dimethylamino-pyridin-3-yl)-1H-pyrrolo[2,3-b]pyridine-3-carbonyl]-2,4-difluoro-phenyl}-amide (P-2229),
Propane-1-sulfonic acid {2,4-difluoro-3-[5-(6-pyrrolidin-1-yl-pyridin-3-yl)-1H-pyrrolo[2,3-b]pyridine-3-carbonyl]-phenyl}-amide (P-2231),
Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide (P-2232),
Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide (P-2233),
Propane-1-sulfonic acid {2,4-difluoro-3-[5-(6-hydroxy-pyridin-3-yl)-1H-pyrrolo[2,3-b]pyridine-3-carbonyl]-phenyl}-amide (P-2234),
Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide (P-2235),
Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide (P-2236), and
a salt, prodrug, or tautomer thereof.

In one embodiment of compounds of Formula I, the compound is a pan Raf inhibitor selected from the group consisting of:
Propane-1-sulfonic acid [2,4-difluoro-3-(5-pyrimidin-5-yl-1H-pyrrolo[2,3-b]pyridine-3-carbonyl)-phenyl]-amide (P-2162),
Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide (P-2189),
Propane-1-sulfonic acid {3-[5-(2-dimethylamino-pyrimidin-5-yl)-1H-pyrrolo[2,3-b]pyridine-3-carbonyl]-2,4-difluoro-phenyl}-amide (P-2196),
Propane-1-sulfonic acid {2,4-difluoro-3-[5-(2-morpholin-4-yl-pyrimidin-5-yl)-1H-pyrrolo[2,3-b]pyridine-3-carbonyl]-phenyl}-amide (P-2197),
Propane-1-sulfonic acid {3-[5-(2,4-dimethoxy-pyrimidin-5-yl)-1H-pyrrolo[2,3-b]pyridine-3-carbonyl]-2,4-difluoro-phenyl}-amide (P-2199),
Propane-1-sulfonic acid (3-{5-[2-(3-dimethylamino-propoxy)-pyrimidin-5-yl]-1H-pyrrolo[2,3-b]pyridine-3-carbonyl}-2,4-difluoro-phenyl)-amide (P-2203),
Propane-1-sulfonic acid {2,4-difluoro-3-[5-(2-methyl-pyrimidin-5-yl)-1H-pyrrolo[2,3-b]pyridine-3-carbonyl]-phenyl}-amide (P-2211),
Propane-1-sulfonic acid {2,4-difluoro-3-[5-(2-pyrrolidin-1-yl-pyrimidin-5-yl)-1H-pyrrolo[2,3-b]pyridine-3-carbonyl]-phenyl}-amide (P-2219),
Propane-1-sulfonic acid {2-fluoro-3-[5-(2-methoxy-pyrimidin-5-yl)-1H-pyrrolo[2,3-b]pyridine-3-carbonyl]-phenyl}-amide (P-2407),
Propane-1-sulfonic acid {3-[5-(2-dimethylamino-pyrimidin-5-yl)-1H-pyrrolo[2,3-b]pyridine-3-carbonyl]-2-fluoro-phenyl}-amide (P-2408), and
a salt, prodrug, or tautomer thereof.

In one embodiment of compounds of Formula I, the compound is a pan Raf inhibitor selected from the group consisting of:
Propane-1-sulfonic acid {2,4-difluoro-3-[5-(1H-pyrazol-4-yl)-1H-pyrrolo[2,3-b]pyridine-3-carbonyl]-phenyl}-amide (P-2174),
Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide (P-2177),
Propane-1-sulfonic acid {3-[5-(1-benzyl-1H-pyrazol-4-yl)-1H-pyrrolo[2,3-b]pyridine-3-carbonyl]-2,4-difluoro-phenyl}-amide (P-2190),
Propane-1-sulfonic acid {2,4-difluoro-3-[5-(2-fluoro-pyridin-4-yl)-1H-pyrrolo[2,3-b]pyridine-3-carbonyl]-phenyl}-amide (P-2192),
Propane-1-sulfonic acid {2,4-difluoro-3-[5-(3-methoxy-prop-1-ynyl)-1H-pyrrolo[2,3-b]pyridine-3-carbonyl]-phenyl}-amide (P-2239),
Propane-1-sulfonic acid {3-[5-(3-diethylamino-prop-1-ynyl)-1H-pyrrolo[2,3-b]pyridine-3-carbonyl]-2,4-difluoro-phenyl}-amide (P-2241),
Propane-1-sulfonic acid [3-(5-ethynyl-1H-pyrrolo[2,3-b]pyridine-3-carbonyl)-2,4-difluoro-phenyl]-amide (P-2260),
2-Methyl-propane-1-sulfonic acid {2,4-difluoro-3-[5-(1-methyl-1H-pyrazol-4-yl)-1H-pyrrolo[2,3-b]pyridine-3-carbonyl]-phenyl}-amide (P-2299), and
a salt, prodrug, or tautomer thereof.

In one embodiment of compounds of Formula I, the compound is a pan Raf inhibitor selected from the group consisting of:
N-(4-{3-[2,6-Difluoro-3-(propane-1-sulfonylamino)-benzoyl]-1H-pyrrolo[2,3-b]pyridin-5-yl}-phenyl)-acetamide (P-2161),
Propane-1-sulfonic acid {2,4-difluoro-3-[5-(4-methanesulfonylamino-phenyl)-1H-pyrrolo[2,3-b]pyridine-3-carbonyl]-phenyl}-amide (P-2165),
Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide (P-2166),
4-{3-[2,6-Difluoro-3-(propane-1-sulfonylamino)-benzoyl]-1H-pyrrolo[2,3-b]pyridin-5-yl}-N-methyl-benzene sulfonamide (P-2167),
N-Cyclopropyl-4-{3-[2,6-difluoro-3-(propane-1-sulfonylamino)-benzoyl]-1H-pyrrolo[2,3-b]pyridin-5-yl}-benzenesulfonamide (P-2168),
Propane-1-sulfonic acid {2,4-difluoro-3-[5-(4-methanesulfonyl-phenyl)-1H-pyrrolo[2,3-b]pyridine-3-carbonyl]-phenyl}-amide (P-2183),
4-{3-[2,6-Difluoro-3-(propane-1-sulfonylamino)-benzoyl]-1H-pyrrolo[2,3-b]pyridin-5-yl}-N,N-dimethyl-benzenesulfonamide (P-2185),
4-{3-[2,6-Difluoro-3-(propane-1-sulfonylamino)-benzoyl]-1H-pyrrolo[2,3-b]pyridin-5-yl}-benzenesulfonamide (P-2194),
Propane-1-sulfonic acid {3-[5-(4-ethanesulfonyl-phenyl)-1H-pyrrolo[2,3-b]pyridine-3-carbonyl]-2,4-difluoro-phenyl}-amide (P-2218),
Propane-1-sulfonic acid (2,4-difluoro-3-{5-[4-(propane-2-sulfonyl)-phenyl]-1H-pyrrolo[2,3-b]pyridine-3-carbonyl}-phenyl)-amide (P-2223),
Propane-1-sulfonic acid {2,4-difluoro-3-[5-(3-methanesulfonyl-phenyl)-1H-pyrrolo[2,3-b]pyridine-3-carbonyl]-phenyl}-amide (P-2228), and
a salt, prodrug, or tautomer thereof.

In one embodiment of compounds of Formula I, the compound is a pan Raf inhibitor selected from the group consisting of:
N-[3-(5-Chloro-1H-pyrrolo[2,3-b]pyridine-3-carbonyl)-2,4-difluoro-phenyl]-2,6-difluoro-benzenesulfonamide (P-2003),
N-[2,4-Difluoro-3-(5-methyl-1H-pyrrolo[2,3-b]pyridine-3-carbonyl)-phenyl]-2,6-difluoro-benzenesulfonamide (P-2024),
N-[3-(5-Cyano-1H-pyrrolo[2,3-b]pyridine-3-carbonyl)-2,4-difluoro-phenyl]-2,6-difluoro-benzenesulfonamide (P-2029),
N-[3-(4-Chloro-1H-pyrrolo[2,3-b]pyridine-3-carbonyl)-2,4-difluoro-phenyl]-2,6-difluoro-benzenesulfonamide (P-2033),
N-[3-(4-Cyano-1H-pyrrolo[2,3-b]pyridine-3-carbonyl)-2,4-difluoro-phenyl]-2,6-difluoro-benzenesulfonamide (P-2037),
N-{2,4-Difluoro-3-[5-(2-methoxy-pyrimidin-5-yl)-1H-pyrrolo[2,3-b]pyridine-3-carbonyl]-phenyl}-2,6-difluoro-benzenesulfonamide (P-2043),
N-[3-(5-Cyano-1H-pyrrolo[2,3-b]pyridine-3-carbonyl)-2-fluoro-phenyl]-2,6-difluoro-benzenesulfonamide (P-2054), and
a salt, prodrug, or tautomer thereof.

In one embodiment of compounds of Formula I, the compound is a pan Raf inhibitor selected from the group consisting of:
N-[2,4-Difluoro-3-(5-methyl-1H-pyrrolo[2,3-b]pyridine-3-carbonyl)-phenyl]-3-fluoro-benzenesulfonamide (P-2016),
N-[3-(4-Chloro-1H-pyrrolo[2,3-b]pyridine-3-carbonyl)-2,4-difluoro-phenyl]-3-fluoro-benzenesulfonamide (P-2019),
N-[2,4-Difluoro-3-(4-methoxy-1H-pyrrolo[2,3-b]pyridine-3-carbonyl)-phenyl]-3-fluoro-benzenesulfonamide (P-2023),
N-[3-(4-Cyano-1H-pyrrolo[2,3-b]pyridine-3-carbonyl)-2,4-difluoro-phenyl]-3-fluoro-benzenesulfonamide (P-2039),
N-{2,4-Difluoro-3-[5-(2-methoxy-pyrimidin-5-yl)-1H-pyrrolo[2,3-b]pyridine-3-carbonyl]-phenyl}-3-fluoro-benzenesulfonamide (P-2045),
N-[3-(5-Cyano-1H-pyrrolo[2,3-b]pyridine-3-carbonyl)-2-fluoro-phenyl]-3-fluoro-benzenesulfonamide (P-2053), and
a salt, prodrug, or tautomer thereof.

In one embodiment of compounds of Formula I, the compound is a pan Raf inhibitor selected from the group consisting of:
N-[3-(5-Chloro-1H-pyrrolo[2,3-b]pyridine-3-carbonyl)-2,4-difluoro-phenyl]-2,5-difluoro-benzenesulfonamide (P-2002),
N-[2,4-Difluoro-3-(5-methoxy-1H-pyrrolo[2,3-b]pyridine-3-carbonyl)-phenyl]-2,5-difluoro-benzenesulfonamide (P-2010),
N-[2,4-Difluoro-3-(5-methyl-1H-pyrrolo[2,3-b]pyridine-3-carbonyl)-phenyl]-2,5-difluoro-benzenesulfonamide (P-2015),
N-[3-(4-Chloro-1H-pyrrolo[2,3-b]pyridine-3-carbonyl)-2,4-difluoro-phenyl]-2,5-difluoro-benzenesulfonamide (P-2018),
N-[2,4-Difluoro-3-(4-methoxy-1H-pyrrolo[2,3-b]pyridine-3-carbonyl)-phenyl]-2,5-difluoro-benzenesulfonamide (P-2022),
N-[3-(4-Cyano-1H-pyrrolo[2,3-b]pyridine-3-carbonyl)-2,4-difluoro-phenyl]-2,5-difluoro-benzenesulfonamide (P-2036), N-{2,4-Difluoro-3-[5-(2-methoxy-pyrimidin-5-yl)-1H-pyrrolo[2,3-b]pyridine-3-carbonyl]-phenyl}-2,5-difluoro-benzenesulfonamide (P-2042),
N-[3-(5-Cyano-1H-pyrrolo[2,3-b]pyridine-3-carbonyl)-2-fluoro-phenyl]-2,5-difluoro-benzenesulfonamide (P-2052), and
a salt, prodrug, or tautomer thereof.

In one embodiment of compounds of Formula I, the compound is a pan Raf inhibitor selected from the group consisting of:
N-[2,4-Difluoro-3-(5-methoxy-1H-pyrrolo[2,3-b]pyridine-3-carbonyl)-phenyl]-2-fluoro-benzenesulfonamide (P-2009),
N-[3-(5-Cyano-1H-pyrrolo[2,3-b]pyridine-3-carbonyl)-2,4-difluoro-phenyl]-2-fluoro-benzenesulfonamide (P-2011),
N-[2,4-Difluoro-3-(5-methyl-1H-pyrrolo[2,3-b]pyridine-3-carbonyl)-phenyl]-2-fluoro-benzenesulfonamide (P-2014),
N-[3-(4-Chloro-1H-pyrrolo[2,3-b]pyridine-3-carbonyl)-2,4-difluoro-phenyl]-2-fluoro-benzenesulfonamide (P-2017),
N-[3-(4-Cyano-1H-pyrrolo[2,3-b]pyridine-3-carbonyl)-2,4-difluoro-phenyl]-2-fluoro-benzenesulfonamide (P-2020),
N-[2,4-Difluoro-3-(4-methoxy-1H-pyrrolo[2,3-b]pyridine-3-carbonyl)-phenyl]-2-fluoro-benzenesulfonamide (P-2021),
N-{2,4-Difluoro-3-[5-(2-methoxy-pyrimidin-5-yl)-1H-pyrrolo[2,3-b]pyridine-3-carbonyl]-phenyl}-2-fluoro-benzenesulfonamide (P-2041),
N-[3-(5-Cyano-1H-pyrrolo[2,3-b]pyridine-3-carbonyl)-2-fluoro-phenyl]-2-fluoro-benzenesulfonamide (P-2051), and
a salt, prodrug, or tautomer thereof.

In one embodiment of compounds of Formula I, the compound is a pan Raf inhibitor selected from the group consisting of:
Pyridine-3-sulfonic acid [2,4-difluoro-3-(5-methyl-1H-pyrrolo[2,3-b]pyridine-3-carbonyl)-phenyl]-amide (P-2069),
Pyridine-3-sulfonic acid [3-(5-chloro-1H-pyrrolo[2,3-b]pyridine-3-carbonyl)-2,4-difluoro-phenyl]-amide (P-2071),
Pyridine-3-sulfonic acid [3-(5-cyano-1H-pyrrolo[2,3-b]pyridine-3-carbonyl)-2,4-difluoro-phenyl]-amide (P-2072),
Pyridine-3-sulfonic acid [2,4-difluoro-3-(4-methoxy-1H-pyrrolo[2,3-b]pyridine-3-carbonyl)-phenyl]-amide (P-2073),
Pyridine-3-sulfonic acid [3-(4-chloro-1H-pyrrolo[2,3-b]pyridine-3-carbonyl)-2,4-difluoro-phenyl]-amide (P-2074),
Pyridine-3-sulfonic acid [3-(4-cyano-1H-pyrrolo[2,3-b]pyridine-3-carbonyl)-2,4-difluoro-phenyl]-amide (P-2077),
Pyridine-3-sulfonic acid [3-(5-cyano-1H-pyrrolo[2,3-b]pyridine-3-carbonyl)-2-fluoro-phenyl]-amide (P-2086), and
a salt, prodrug, or tautomer thereof.

In one embodiment of compounds of Formula I, the compound is a pan Raf inhibitor selected from the group consisting of:
N-[3-(5-Cyano-1H-pyrrolo[2,3-b]pyridine-3-carbonyl)-2,4-difluoro-phenyl]-benzene sulfonamide (P-2046),
N-[3-(5-Cyano-1H-pyrrolo[2,3-b]pyridine-3-carbonyl)-2-fluoro-phenyl]-benzene sulfonamide (P-2056), and
a salt, prodrug, or tautomer thereof.

In a tenth aspect, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are therapeutically effective for the same disease indication. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In an eleventh aspect, methods are provided for treating a disease or condition mediated by one or more Raf kinases (including A-Raf, B-Raf, and c-Raf-1) including mutations thereof, in a subject in need thereof by administering to the subject an effective amount of a composition including any one or more compound(s) as described herein. In one embodiment, the invention provides methods for treating a disease or condition mediated by one or more Raf kinases, including mutations thereof, by administering to the subject an effective amount of a composition including any one or more compound(s) as described herein in combination with one or more other suitable therapies for treating the disease.

In a twelfth aspect, methods are provided for treating a disease or condition mediated by A-Raf kinase, including any mutations thereof, in a subject in need thereof by administering to the subject an effective amount of a composition including any one or more compound(s) as described herein. In one embodiment, the invention provides methods for treating a disease or condition mediated by A-Raf kinase, including any mutations thereof, by administering to the subject an effective amount of a composition including any one or more compound(s) as described herein in combination with one or more other suitable therapies for treating the disease.

In a thirteenth aspect, methods are provided for treating a disease or condition mediated by B-Raf kinase, including any mutations thereof, in a subject in need thereof by administering to the subject an effective amount of a composition including any one or more compound(s) as described herein. In one embodiment, the invention provides methods for treating a disease or condition mediated by B-Raf kinase, including any mutations thereof, by administering to the subject an effective amount of a composition including any one or more compound(s) as described herein in combination with one or more other suitable therapies for treating the disease.

In a fourteenth aspect, methods are provided for treating a cancer disease or condition mediated by B-Raf V600E mutant kinase, in a subject in need thereof by administering to the subject an effective amount of a composition including any one or more compound(s) of the invention as described herein. In one embodiment, the invention provides methods for treating a disease or condition mediated by B-Raf V600E mutant kinase, by administering to the subject an effective amount of a composition including any one or more compound(s) as described herein in combination with one or more other suitable therapies for treating the disease. In one embodiment, the invention provides methods for treating a cancer mediated by B-Raf V600E mutant by administering to the subject an effective amount of a composition including any one or more compound(s) as described herein. In one embodiment, the invention provides methods for treating a cancer mediated by B-Raf V600E mutant by administering to the subject an effective amount of a composition including any one or more compound(s) as described herein in combination with one or more suitable anticancer therapies, such as one or more chemotherapeutic drugs.

In a fifteenth aspect, methods are provided for treating a disease or condition mediated by c-Raf-1 kinase, including any mutations thereof, in a subject in need thereof by administering to the subject an effective amount of a composition including any one or more compound(s) as described herein. In one embodiment, the invention provides methods for treating a disease or condition mediated by c-Raf-1 kinase, including any mutations thereof, by administering to the subject an effective amount of a composition including any one or more compound(s) as described herein in combination with one or more other suitable therapies for treating the disease.

In a sixteenth aspect, methods are provided for treating a disease or condition mediated by a Ras mutant-activated Raf kinase, in a subject in need thereof by administering to the subject an effective amount of a composition including any one or more compound(s) as described herein. In one embodiment, the invention provides methods for treating a disease or condition mediated by a Ras mutant-activated Raf kinase, by administering to the subject an effective amount of a composition including any one or more compound(s) as described herein in combination with one or more other suitable therapies for treating the disease.

In a seventeenth aspect, methods are provided for treating a cancer in a subject in need thereof by administering to the subject an effective amount of a composition including any one or more compound(s) as described herein. In one embodiment, the invention provides a method of treating a cancer in a subject in need thereof by administering to the subject an effective amount of a composition including any one or more compound(s) as described herein in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In an eighteenth aspect, methods are provided for treating a cancer in a subject in need thereof by administering to the subject an effective amount of a composition including any one or more compound(s) as described herein, in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, azathioprine, raltitrexed, tegafur-uracil, thioguanine, trimethoprim, trimetrexate, and vidarabine; an immunotherapy, including, but not limited to, alemtuzumab, bevacizumab, cetuximab, galiximab, gemtuzumab, panitumumab, pertuzumab, rituximab, tositumomab, trastuzumab, 90Y ibritumomab tiuxetan, ipilimumab, and tremelimumab; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. tanespimycin) and farnesyltransferase inhibitors (e.g. tipifarnib). Preferably, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-α, interleukin-2, or erlotinib.

In a nineteenth aspect, methods are provided for treating a disease or condition in a subject in need thereof, by administering to the subject a therapeutically effective amount of any one or more compound(s) as described herein, a prodrug of such compound, or a pharmaceutically acceptable salt of such compound or prodrug, or a pharmaceutically acceptable formulation of such compound or prodrug. The compound can be alone or can be part of a composition. In one embodiment, methods are provided for treating a disease or condition in a subject, by administering to the subject a therapeutically effective amount of any one or more compound(s) as described herein, a prodrug of such compound, a pharmaceutically acceptable salt of such compound or prodrug, or a pharmaceutically acceptable formulation of such compound or prodrug in combination with one or more other suitable therapies for the disease or condition.

In a twentieth aspect, the invention provides kits that include any one or more compound(s) or composition(s) thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit may include written instructions for use and/or other indication that the compound or composition is suitable or approved for administration to a mammal, e.g., a human, for a Raf protein kinase-mediated disease or condition; and the compound or composition may be packaged in unit dose or single dose form, e.g., single dose pills, capsules, or the like.

In aspects and embodiments involving treatment of a disease or condition with any one or more compound(s) as described herein, the invention provides methods for treating an A-Raf-mediated, B-Raf-mediated and/or c-Raf-1-mediated disease or condition in a subject in need thereof, e.g., a disease or condition characterized by abnormal A-Raf, B-Raf, and/or c-Raf-1 activity (e.g. kinase activity). In some embodiments, invention methods may involve administering to the subject suffering from or at risk of an A-Raf-mediated, B-Raf-mediated and/or c-Raf-1-mediated disease or condition an effective amount of any one or more Raf inhibitor(s) as described herein. In one embodiment, the A-Raf-mediated, B-Raf-mediated, and/or c-Raf-1-mediated disease is selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, and pheochromocytoma. In one embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the disease or condition is selected from the group consisting of melanoma, glioma, colorectal cancer, thyroid cancer, lung cancer, ovarian cancer, prostate cancer, and biliary tract cancer. In one embodiment, the disease or condition is selected from the group consisting of melanoma, colorectal cancer, thyroid cancer, ovarian cancer and biliary tract cancer.

In aspects and embodiments involving treatment of a disease or condition with any one or more compound(s) as described herein, the invention provides methods for treating a Ras mutant-activated Raf-mediated disease or condition in a subject in need thereof, e.g., a disease or condition characterized by Raf kinase activated by a Ras mutation. In some embodiments, invention methods may involve administering to the subject suffering from or at risk of Ras mutant-activated Raf-mediated disease or condition an effective amount of any one or more pan Raf inhibitor(s) as described herein. In one embodiment, the Ras mutant-activated Raf-mediated disease or condition is selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia.

In aspects and embodiments involving treatment of a disease or condition with any one or more compound(s) as described herein, methods are provided for treating a disease or condition in a subject in need thereof, wherein the disease or condition is selected from the group consisting of polycystic kidney disease, acute pain, and chronic pain.

In aspects and embodiments involving treatment of a disease or condition with any one or more compound(s) as described herein, methods are provided for treating a disease or condition in a subject in need thereof, wherein the disease or condition is a cancer. In one embodiment, the cancer is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the cancer is selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia.

In aspects and embodiments involving treatment of a disease or condition with any one or more compound(s) as described herein, methods are provided for treating a cancer in a subject in need thereof. In some embodiments, methods may involve administering to the subject suffering from or at risk of a cancer an effective amount of any one or more pan Raf inhibitor(s) as described herein, wherein the cancer is selected from the group consisting of melanoma, glioma, glioblastoma, pilocytic astrocytoma, liver cancer, biliary tract cancer, colorectal cancer, lung cancer, bladder cancer, gallbladder cancer, breast cancer, pancreatic cancer, thyroid cancer, kidney cancer, ovarian cancer, adrenocortical cancer, prostate cancer, cervical cancer, endometrial cancer, gastrointestinal stromal tumors, medullary thyroid cancer, tumor angiogenesis, acute myeloid leukemia, chronic myelomonocytic leukemia, childhood acute lymphoblastic leukemia, plasma cell leukemia, and multiple myeloma. In one embodiment, the cancer is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the cancer is selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia.

In a twenty-first aspect, compounds as described herein can be used in the preparation of a medicament for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, and pheochromocytoma. In one embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the disease or condition is selected from the group consisting of melanoma, glioma, colorectal cancer, thyroid cancer, lung cancer, ovarian cancer, prostate cancer, and biliary tract cancer. In one embodiment, the disease or condition is selected from the group consisting of melanoma, colorectal cancer, thyroid cancer, ovarian cancer and biliary tract cancer.

In a twenty-second aspect, compounds as described herein can be used in the preparation of a medicament for the treatment of a Ras mutant-activated Raf-mediated disease or condition selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia.

In a twenty-third aspect, compounds as described herein can be used in the preparation of a medicament for the treatment of a disease or condition selected from the group consisting of polycystic kidney disease, acute pain, and chronic pain.

In a twenty-fourth aspect, compounds as described herein can be used in the preparation of a medicament for the treatment of a disease or condition selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the disease or condition is selected from the group consisting of melanoma, glioma, colorectal cancer, thyroid cancer, lung cancer, ovarian cancer, prostate cancer, and biliary tract cancer.

In a twenty-fifth aspect, compounds as described herein can be used in the preparation of a medicament for the treatment of a disease or condition selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia. In one embodiment, the disease or condition is selected from the group consisting of melanoma, colorectal cancer, thyroid cancer, ovarian cancer and biliary tract cancer.

In a twenty-sixth aspect, there are provided compounds as described herein for the treatment of an A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to *Helicobacter pylori*, Hepatitis and Influenza viruses, fever, HIV and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, and pheochromocytoma. In one embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the disease or condition is selected from the group consisting of melanoma, glioma, colorectal cancer, thyroid cancer, lung cancer, ovarian cancer, prostate cancer, and biliary tract cancer. In one embodiment, the disease or condition is selected from the group consisting of melanoma, colorectal cancer, thyroid cancer, ovarian cancer and biliary tract cancer.

In a twenty-seventh aspect, there are provided compounds as described herein for the treatment of a Ras mutant-activated Raf-mediated disease or condition selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia.

In a twenty-eighth aspect, there are provided compounds as described herein for the treatment of a disease or condition selected from the group consisting of polycystic kidney disease, acute pain, and chronic pain.

In a twenty-ninth aspect, there are provided compounds as described herein for the treatment of a disease or condition selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, and biliary tract cancer. In one embodiment, the disease or condition is selected from the group consisting of melanoma, glioma, colorectal cancer, thyroid cancer, lung cancer, ovarian cancer, prostate cancer, and biliary tract cancer.

In a thirtieth aspect, there are provided compounds as described herein for the treatment of a disease or condition selected from the group consisting of melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia. In one embodiment, the disease or condition is selected from the group consisting of melanoma, colorectal cancer, thyroid cancer, ovarian cancer and biliary tract cancer.

Any one or more of compounds as provided herein demonstrate desirable inhibitory activity on Raf kinases, including desirable activity profiles within the Raf kinases with selectivity relative to other kinases. In some embodiments, compounds as provided herein demonstrate inhibition of proliferation of tumorigenic cell lines that are driven by a Ras mutation. Compounds further demonstrate one or more desirable properties, including enhanced pharmacokinetic properties, greater solubility, lesser Cyp inhibition, and the like.

Additional aspects and embodiments will be apparent from the following Detailed Description and from the claims.

DETAILED DESCRIPTION OF THE PREFERRED EMBODIMENTS

As used herein the following definitions apply unless clearly indicated otherwise:

All atoms designated within a Formula or compound described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example; $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes example $^{35}Cl$, $^{36}Cl$, $^{37}Cl$, $^{38}Cl$, $^{39}Cl$; and the like.

"Halogen" refer to all halogens, that is, chloro (Cl), fluoro (F), bromo (Br), or iodo (I).

"Hydroxyl" or "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. A "lower alkyl" may be independently substituted as described herein, unless indicated otherwise, with one or more, preferably 1, 2, 3, 4 or 5, also 1, 2, or 3 substituents, wherein the substituents are as indicated. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. It is understood that any such substitutions, or substitution of lower alkyl on another moiety, are chemically feasible and attached at any available atom to provide a stable compound.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. The straight chain or branched lower alkenyl group is chemically feasible and attached at any available point to provide a stable compound. Examples of lower alkenyl groups include ethenyl, propenyl, isopropenyl, butenyl, and the like. A "lower alkenyl" may be independently substituted as described herein, unless indicated otherwise, with one or more, preferably 1, 2, 3, 4 or 5, also 1, 2, or 3 substituents, wherein the substituents are as indicated. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. It is understood that any such substitutions, or substitution of lower alkenyl on another moiety, are chemically feasible and attached at any available atom to provide a stable compound.

"Lower alkynyl" alone or in combination means a straight or branched hydrocarbon containing 2-6 carbon atoms (unless specifically defined) containing at least one, preferably one, carbon to carbon triple bond. The straight chain or branched lower alkynyl group is chemically feasible and attached at any available point to provide a stable compound. Examples of alkynyl groups include ethynyl, propynyl, butynyl, and the like. A "lower alkynyl" may be independently substituted as described herein, unless indicated otherwise, with one or more, preferably 1, 2, 3, 4 or 5, also 1, 2, or 3 substituents, wherein the substituents are as indicated. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. It is understood that any such substitutions, or substitution of lower alkynyl on another moiety, are chemically feasible and attached at any available atom to provide a stable compound "Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, cycloheptyl, and the like. A "cycloalkyl" may be independently substituted as described herein, unless indicated otherwise, with one or more, preferably 1, 2, 3, 4 or 5, also 1, 2, or 3 substituents, wherein the substituents are as indicated. It is understood that any such substitutions, or substitutions of cycloalkyl on another moiety, are chemically feasible and attached at any available atom to provide a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which a ring carbon may be oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. A "heterocycloalkyl" may be independently substituted as described herein, unless indicated otherwise, with one or more, preferably 1, 2, 3, 4 or 5, also 1, 2, or 3 substituents, wherein the substituents are as indicated. It is understood that any such substitutions, or substitutions of heterocycloalkyl on another moiety, are chemically feasible and attached at any available atom to provide a stable compound.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. An "aryl" may be independently substituted as described herein, unless indicated otherwise, with one or more, preferably 1, 2, 3, 4 or 5, also 1, 2, or 3 substituents, wherein the substituents area as indicated. It is understood that any such substitutions, or substitutions of aryl on another moiety, are chemically feasible and attached at any available atom to provide a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A "heteroaryl" may be independently substituted as described herein, unless indicated otherwise, with one or more, preferably 1, 2, 3, 4 or 5, also 1, 2, or 3 substituents, wherein the substituents are as indicated. It is understood that any such substitutions, or substitutions of heteroaryl on another moiety, are chemically feasible and attached at any available atom to provide a stable compound.

"Lower alkoxy" denotes the group —$OR^a$, where $R^a$ is lower alkyl. A "lower alkoxy" may be independently substituted, i.e. $R^a$ is lower alkyl substituted with one or more substituents as indicated herein. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. It is understood that substitutions on alkoxy, or alkoxy substitution of other moieties, are chemically feasible and attached at any available atom to provide a stable compound.

"Lower alkylthio" denotes the group —$SR^b$, where $R^b$ is lower alkyl. A "lower alkylthio" may be independently substituted, i.e. $R^b$ is lower alkyl substituted with one or more substituents as indicated herein. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. It is understood that substitutions on alkylthio, or alkylthio substitution of other moieties, are chemically feasible and attached at any available atom to provide a stable compound.

"Mono-alkylamino" denotes the group —$NHR^c$ where $R^c$ is lower alkyl. "Di-alkylamino" denotes the group —$NR^cR^d$, where $R^c$ and $R^d$ are independently lower alkyl. "Cycloalkylamino" denotes the group —$NR^eR^f$, where $R^e$ and $R^f$ combine with the nitrogen to form a 5-7 membered heterocycloalkyl, where the heterocycloalkyl may contain an additional heteroatom within the ring, such as O, N, or S, and may also be further substituted with one or more lower alkyl. Examples of 5-7 membered heterocycloalkyl include, but are not limited to, piperidine, piperazine, 4-methylpiperazine, morpholine, and thiomorpholine. It is understood that when mono-alkylamino, di-alkylamino, or cycloalkylamino are substituents on other moieties, these are chemically feasible and attached at any available atom to provide a stable compound.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "Raf protein kinase mediated disease or condition" refers to a disease or condition in which the biological function of a Raf protein kinase (also referred to as Raf kinase, or Raf), including any of A-Raf protein kinase, B-Raf protein kinase or c-Raf-1 protein kinase, or any mutation thereof, affects the development, course, and/or symptoms of the disease or condition, and/or in which modulation of Raf alters the development, course, and/or symptoms of the disease or condition. The Raf mediated disease or condition includes a disease or condition for which Raf modulation provides a therapeutic benefit, e.g. wherein treatment with Raf inhibitor(s), including one or more compound(s) described herein, provides a therapeutic benefit to the subject suffering from or at risk of the disease or condition.

As used herein, the term "A-Raf protein kinase mediated disease or condition," and the like refer to a disease or condition in which the biological function of an A-Raf protein kinase (also referred to as A-Raf kinase, or A-Raf), including any mutations thereof, affects the development, course, and/or symptoms of the disease or condition, and/or in which modulation of A-Raf alters the development, course, and/or symptoms of the disease or condition. The A-Raf mediated disease or condition includes a disease or condition for which A-Raf inhibition provides a therapeutic benefit, e.g. wherein treatment with a compound that inhibits A-Raf, including one or more compound(s) described herein, provides a therapeutic benefit to the subject suffering from or at risk of the disease or condition.

As used herein, the term "B-Raf protein kinase mediated disease or condition," and the like refer to a disease or condition in which the biological function of a B-Raf protein kinase (also referred to as B-Raf kinase, or B-Raf), including any mutations thereof, affects the development, course, and/or symptoms of the disease or condition, and/or in which modulation of B-Raf alters the development, course, and/or symptoms of the disease or condition. The B-Raf mediated disease or condition includes a disease or condition for which B-Raf inhibition provides a therapeutic benefit, e.g. wherein treatment with a compound that inhibits B-Raf, including one or more compound(s) described herein, provides a therapeutic benefit to the subject suffering from or at risk of the disease or condition.

As used herein, the term "B-Raf V600E mutant protein kinase mediated disease or condition," and the like refer to a disease or condition in which the biological function of B-Raf V600E mutant protein kinase (also referred to as B-Raf V600E kinase, or B-Raf V600E) affects the development, course, and/or symptoms of the disease or condition, and/or in which modulation of B-Raf V600E alters the development, course, and/or symptoms of the disease or condition. The B-Raf V600E mediated disease or condition includes a disease or condition for which B-Raf V600E inhibition provides a therapeutic benefit, e.g. wherein treatment with a compound that inhibits B-Raf V600E, including one or more compound(s) described herein, provides a therapeutic benefit to the subject suffering from or at risk of the disease or condition.

As used herein, the term "c-Raf-1 protein kinase mediated disease or condition," and the like refer to a disease or condition in which the biological function of a c-Raf-1 protein kinase (also referred to as c-Raf-1 kinase, or c-Raf-1), including any mutations thereof, affects the development, course, and/or symptoms of the disease or condition, and/or in which modulation of c-Raf-1 alters the development, course, and/or symptoms of the disease or condition. The c-Raf-1 mediated disease or condition includes a disease or condition for which c-Raf-1 inhibition provides a therapeutic benefit, e.g. wherein treatment with a compound that inhibits c-Raf-1, including one or more compound(s) described herein, provides a therapeutic benefit to the subject suffering from or at risk of the disease or condition.

As used herein, the term "Ras mutant-activated Raf protein kinase mediated disease or condition," and the like refer to a disease or condition in which the biological function of a Raf protein kinase is activated by a mutation in Ras protein kinase, such that the Ras mutation-activated Raf kinase affects the development, course, and/or symptoms of the disease or condition. The Ras mutant-activated Raf kinase-mediated disease or condition includes a disease or condition for which a pan Raf inhibitor as described herein provides a therapeutic benefit, e.g. wherein treatment with a compound that inhibits A-Raf, B-Raf, B-Raf V600E, and c-Raf-1 including one or more compound(s) described herein, provides a therapeutic benefit to the subject suffering from or at risk of the disease or condition.

As used herein, the term "Raf inhibitor" refers to a compound that inhibits at least one of A-Raf, B-Raf, c-Raf-1, or any mutations thereof, i.e. a compound having an $IC_{50}$ of less than 500 nM, less than 100 nM, less than 50 nM, less than 20 nM, less than 10 nM, less than 5 nM, or less than 1 nM as determined in a generally accepted Raf kinase activity assay. Such compounds are preferably, but not necessarily, selective with respect to other protein kinases, i.e. when compared to another protein kinase, the $IC_{50}$ for the other kinase divided by the $IC_{50}$ for the Raf kinase is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR.

As used herein, the term "pan Raf inhibitor" refers to a compound that inhibits at least each of B-Raf and c-Raf-1, i.e. a compound having an $IC_{50}$ of less than 100 nM, less than 50 nM, less than 20 nM, less than 10 nM, less than 5 nM, or less than 1 nM as determined in a generally accepted B-Raf kinase activity assay, and having an $IC_{50}$ of less than 500 nM, less than 100 nM, less than 50 nM, less than 20 nM, less than 10 nM, less than 5 nM, or less than 1 nM as determined in a comparable generally accepted c-Raf-1 kinase activity assay. The pan Raf inhibitor may be, but is not necessarily, approximately equipotent on each of B-Raf and c-Raf-1. Compounds are considered approximately equipotent on each of B-Raf and c-Raf-1 if the ratio of $IC_{50}$ for either of B-Raf and c-Raf-1 divided by the $IC_{50}$ for the other of B-Raf and c-Raf-1 (e.g. B-Raf $IC_{50}$ divided by c-Raf-1 $IC_{50}$) is in the range of 10 to 0.1, also 5 to 0.2. Such compounds are preferably, but not necessarily, selective with respect to other protein kinases, i.e. when compared to another protein kinase, the $IC_{50}$ for the other kinase divided by the $IC_{50}$ for either of B-Raf and c-Raf-1 is >10, also >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. The pan Raf inhibitor may also inhibit either or both of A-Raf and B-Raf V600E, where preferably the inhibition of A-Raf and/or B-Raf V600E is approximately equipotent with the inhibition of B-Raf and c-Raf-1. Preferred pan Raf inhibitors inhibit each of A-Raf, B-Raf, c-Raf-1 and B-Raf V600E with approximately equal potency, with an $IC_{50}$ for each of A-Raf, B-Raf, c-Raf-1 and B-Raf V600E of less than 500 nM, less than 100 nM, less than 50 nM, less than 20 nM, less than 10 nM, less than 5 nM, or less than 1 nM as determined in a generally accepted Raf kinase activity assay. While it is understood that a pan Raf inhibitor may be used to treat any A-Raf, B-Raf, c-Raf-1 or B-Raf V600E kinase mediated disease or condition, the inhibition of each of A-Raf, B-Raf, c-Raf-1 and B-Raf V600E provides beneficial effects in treating cancers, in particular cancers having a Ras pathway mutation, such as a Ras mutation that activates Raf kinase, e.g. cancers including, but not limited to, melanoma, liver cancer, biliary tract cancer, colorectal cancer, lung cancer, bladder cancer, breast cancer, pancreatic cancer, thyroid cancer, kidney cancer, ovarian cancer, cervical cancer, endometrial cancer, and acute myeloid leukemia. Such compounds are also beneficial in treating B-Raf V600E mediated cancers that become resistant to B-Raf V600E selective inhibitors.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with an acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailability. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of a combination of two or more components, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

As used herein, the term "biopharmaceutical properties" refers to the pharmacokinetic action of a compound or complex of the present invention, including the dissolution, absorption and distribution of the compound on administration to animal subject. As such, certain solid forms of compounds as described herein, such as amorphous complexes of compounds as described herein are intended to provide improved dissolution and absorption of the active compound, which is typically reflected in improved $C_{max}$ (i.e. the maximum achieved concentration in the plasma after administration of the drug) and improved AUC (i.e. area under the curve of drug plasma concentration vs. time after administration of the drug).

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the term "modulating" or "modulate" refers to an effect of altering a biological activity (i.e. increasing or decreasing the activity), especially a biological activity associated with a particular biomolecule such as a protein kinase. For example, an inhibitor of a particular biomolecule modulates the activity of that biomolecule, e.g., an enzyme, by decreasing the activity of the biomolecule, such as an enzyme. Such activity is typically indicated in terms of an inhibitory concentration ($IC_{50}$) of the compound for an inhibitor with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Description of Raf target protein kinases contemplated by the present invention follow:

A-Raf: Target kinase A-Raf (i.e., v-raf murine sarcoma 3611 viral oncogene homolog 1) is a 67.6 kDa serine/threonine kinase encoded by chromosome Xp11.4-p11.2 (symbol: ARAF). The mature protein comprises RBD (i.e., Ras binding domain) and phorbol-ester/DAG-type zinc finger domain and is involved in the transduction of mitogenic signals from the cell membrane to the nucleus. A-Raf inhibitors may be useful in treating neurologic diseases such as multi-infarct dementia, head injury, spinal cord injury, Alzheimer's disease (AD), Parkinson's disease; neoplastic diseases including, but not limited to, melanoma, glioma, sarcoma, carcinoma (e.g. colorectal, lung, breast, pancreatic, thyroid, renal, ovarian), lymphoma (e.g. histiocytic lymphoma), neurofibromatosis, myelodysplastic syndrome, leukemia, tumor angiogenesis; pain of neuropathic or inflammatory origin, including acute pain, chronic pain, cancer-related pain and migraine; and diseases associated with muscle regeneration or degeneration, including, but not limited to, vascular restenosis, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

B-Raf: Target kinase B-Raf (i.e., v-raf murine sarcoma viral oncogene homolog B1) is a 84.4 kDa serine/threonine kinase encoded by chromosome 7q34 (symbol: BRAF). The mature protein comprises RBD (i.e., Ras binding domain), C1 (i.e., protein kinase C conserved region 1) and STK (i.e., serine/threonine kinase) domains.

Target kinase B-Raf is involved in the transduction of mitogenic signals from the cell membrane to the nucleus and may play a role in the postsynaptic responses of hippocampal neurons. As such, genes of the RAF family encode kinases that are regulated by Ras and mediate cellular responses to growth signals. Indeed, B-Raf kinase is a key component of the RAS->Raf->MEK->ERK/MAP kinase signaling pathway, which plays a fundamental role in the regulation of cell growth, division and proliferation, and, when constitutively activated, causes tumorigenesis. Among several isoforms of Raf kinase, the B-type, or B-Raf, is the strongest activator of the downstream MAP kinase signaling.

The BRAF gene is frequently mutated in a variety of human tumors, especially in malignant melanoma and colon carcinoma. The most common reported mutation was a missense thymine (T) to adenine (A) transversion at nucleotide 1796 (T1796A; amino acid change in the B-Raf protein is Val<600> to Glu<600>) observed in 80% of malignant melanoma tumors. Functional analysis reveals that this transversion is the only detected mutation that causes constitutive activation of B-Raf kinase activity, independent of RAS activation, by converting B-Raf into a dominant transforming protein. Based on precedents, human tumors develop resistance to kinase inhibitors by mutating a specific amino acid in the catalytic domain as the "gatekeeper". (Balak, et. al., Clin Cancer Res. 2006, 12:6494-501). Mutation of Thr-529 in BRAF to Ile is thus anticipated as a mechanism of resistance to BRAF inhibitors, and this can be envisioned as a transition in codon 529 from ACC to ATC.

Niihori et al., report that in 43 individuals with cardio-facio-cutaneous (CFC) syndrome, they identified two heterozygous KRAS mutations in three individuals and eight BRAF mutations in 16 individuals, suggesting that dysregulation of the RAS-RAF-ERK pathway is a common molecular basis for the three related disorders (Niihori et al., Nat. Genet. 2006, 38(3):294-6).

c-Raf-1: Target kinase c-Raf-1 (i.e., v-raf murine sarcoma viral oncogene homolog 1) is a 73.0 kDa STK encoded by chromosome 3p25 (symbol: RAF1). c-Raf-1 can be targeted to to the mitochondria by BCL2 (i.e., oncogene B-cell leukemia 2) which is a regulator of apoptotic cell death. Active c-Raf-1 improves BCL2-mediated resistance to apoptosis, and c-Raf-1 phosphorylates BAD (i.e., BCL2-binding protein). c-Raf-1 is implicated in carcinomas, including colorectal, ovarian, lung and renal cell carcinoma. c-Raf-1 is also implicated as an important mediator of tumor angiogenesis (Hood, J. D. et al., 2002, Science 296, 2404). C-Raf-1 inhibitors may also be useful for the treatment of acute myeloid leukemia and myelodysplastic syndromes (Crump, Curr Pharm Des 2002, 8 (25):2243-8). Raf-1 activators may be useful as treatment for neuroendocrine tumors, such as medullary thyroid cancer, carcinoid, small cell lung cancer and pheochromocytoma (Kunnimalaiyaan et al., Anticancer Drugs 2006, 17(2):139-42).

A-Raf, B-Raf and/or C-Raf-1 inhibitors may be useful in treating A-Raf-mediated, B-Raf-mediated or c-Raf-1-mediated disease or condition selected from the group consisting of neurologic diseases, including, but not limited to, multi-infarct dementia, head injury, spinal cord injury, Alzheimer's disease (AD), Parkinson's disease seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract (e.g. bile duct, cholangiocarcinoma), colorectal, lung, gallbladder, breast, pancreatic, thyroid, renal, ovarian, adrenocortical, prostate), lymphoma (e.g. histiocytic lymphoma) neurofibromatosis, acute myeloid leukemia, myelodysplastic syndrome, leukemia, tumor angiogenesis, gastrointestinal stromal tumors, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases, including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to, *Helicobacter pylori*, Hepatitis and Influenza viruses, fever, HIV and sepsis; pulmonary diseases, including, but not limited to, chronic obstructive pulmonary disease (COPD) and acute respiratory distress syndrome (ARDS); genetic developmental diseases, including, but not limited to, Noonan's syndrome, Costello syndrome, (faciocutaneoskeletal syndrome), LEOPARD syndrome, cardio-faciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency).

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, compounds as described herein may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the pyrrolo[2,3-b]pyridine ring or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.,* 40:2011-2016; Shan et al., 1997, *J Pharm Sci* 86(7):756-757; Bagshawe, 1995, *Drug Dev. Res.,* 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds as described herein may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such steroisomeric forms are included within the formulae provided herein.

In some embodiments, a chiral compound as described herein is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds as described herein can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound as described herein may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences,* 19th ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds as described herein are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining compounds as described herein with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, compounds as described herein may include hydrated or solvated as well as unhydrated or unsolvated forms of the identified compound. For example, the indicated compounds include both hydrated and non-hydrated forms. Other examples of solvates include compounds as described herein in combination with a suitable solvent, such as isopropanol, ethanol, methanol, DMSO, ethyl acetate, acetic acid, or ethanolamine.

Formulations and Administration

Compounds as described herein will typically be used in therapy for human subjects. However, compounds as described herein may also be used to treat similar or identical indications in other animal subjects, and can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds as described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as cross-linked polyvinylpyrrolidone, agar, or alginic acid, or a salt thereof such as sodium alginate; a lubricant, such as talc or magnesium stearate; a plasticizer, such as glycerol or sorbitol; a sweetening agent such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compound may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds as described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds as described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds as described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds as described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds as described herein may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of compounds as described herein to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds as described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds as described herein or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound as described herein, or at the same time as a compound as described herein. Use in combination also includes use with a therapy or medical procedure that is administered once or infrequently, such as surgery, along with a compound as described herein administered within a short time or longer time before or after the other therapy or procedure. In some embodiments, the present invention provides for delivery of a compound as described herein and one or more other drug therapeutics delivered by a different route of administration or by the same route of administration. The use in combination for any route of administration includes delivery of a compound as described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound as described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound as described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the synthesis and use of compounds as described herein are provided below. In most cases, alternative synthetic and analysis techniques can be used. Additional synthetic methods may be used in the synthesis of compounds as described in the following examples, such as methods found, for example, in U.S. patent application Ser. No. 11/473,347 (see also, PCT publication WO2007002433), U.S. patent application Ser. No. 11/960,590 (Publication number 2008/0167338), U.S. patent application Ser. No. 11/961,901 (Publication number 2008/0188514), U.S. patent application Ser. No. 11/986,667 (see also, PCT publication WO2008064265), U.S. Provisional Patent Application Ser. No. 61/060,418, U.S. Provisional Patent Application Ser. No. 61/054,445, and PCT patent application PCT/US2008/070124, the disclosures of which are hereby incorporated by reference regarding methods of making compounds. The examples are intended to be illustrative and are not limiting or restrictive to the scope of the invention. For example, where additional compounds are prepared following a protocol of a Scheme for a particular compound, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. In some examples, the mass spectrometry result indicated for a compound may have more than one value due to the isotope distribution of an atom in the molecule, such as a compound having a bromo or chloro substituent.

Ring numbering for the 1H-pyrrolo[2,3-b]pyridine in the following Examples is as follows:

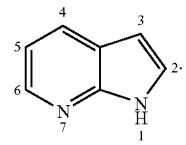

Example 1

Synthesis of (3-amino-2,6-difluoro-phenyl)-(1H-pyrrolo[2,3-b]pyridin-3-yl)-methanone compounds (3-amino-2,6-difluoro-phenyl)-(1H-pyrrolo[2,3-b]pyridin-3-yl)-methanone compounds substituted at the 4 or 5 position were prepared by the following schemes.

Scheme 1

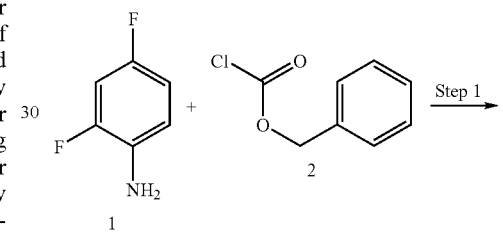

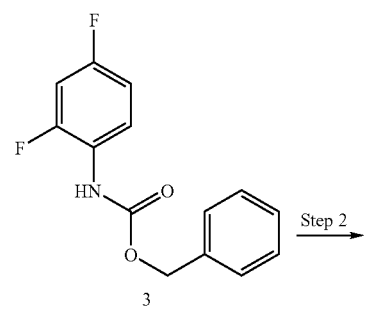

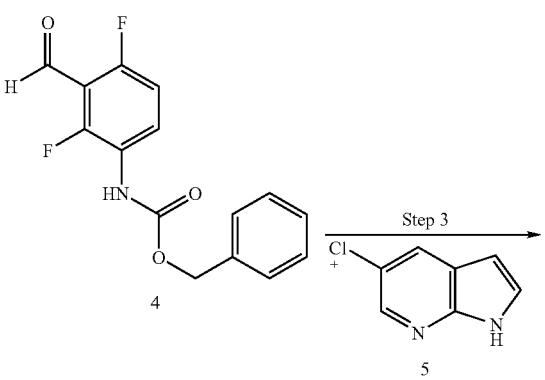

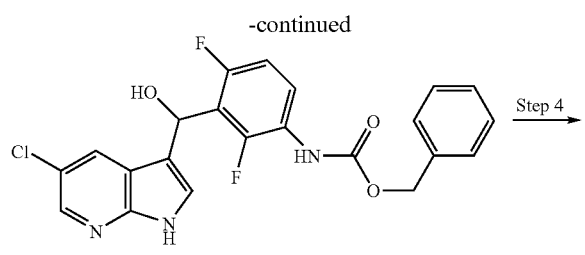

6

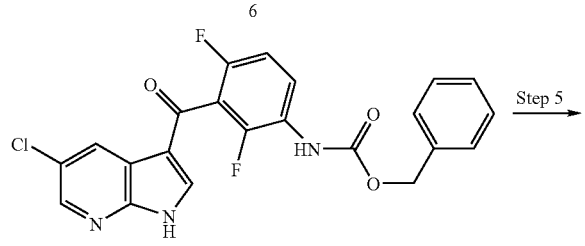

7

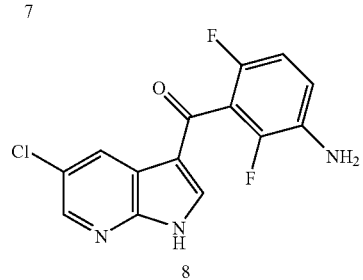

8

Step 1—Preparation of (2,4-difluoro-phenyl)-carbamic acid benzyl ester (3)

To 2,4-difluoro-phenylamine (1, 7.0 mL, 70.0 mmol) in 100 mL of dichloromethane, pyridine (11 mL, 140.0 mmol) and benzyl chloroformate (2, 11.9 mL, 83.4 mmol) were added. The reaction mixture was stirred at room temperature for 1.5 hours. The reaction mixture was concentrated under vacuum and the residue was partitioned between ethyl acetate and potassium bisulfate solution. The organic layer was dried with magnesium sulfate, filtered and the filtrate concentrated under vacuum and crystallized from hexanes to give the desired compound (3, 15.6 g, 85%).

Step 2—Preparation of (2,4-difluoro-3-formyl-phenyl)-carbamic acid benzyl ester (4)

Into a round bottom flask was added (2,4-difluoro-phenyl)-carbamic acid benzyl ester (3, 3.83 g, 14.5 mmol) in 148 mL of tetrahydrofuran. The solution was chilled to −78° C. and n-butyllithium (1.60 M in hexane, 19.1 mL, 30.0 mmol) was added over 30 minutes followed by the addition of 1.12 mL of N,N-dimethylformamide. The reaction mixture was allowed to warm to room temperature and stirred overnight. The reaction mixture was poured into water and extracted with ethyl acetate and the organic layer was washed with brine, dried over sodium sulfate, filtered and the filtrate concentrated under vacuum and crystallized from ether to give the desired compound (4, 3.0 g, 71%).

Step 3—Preparation of {3-[(5-chloro-1H-pyrrolo[2,3-b]pyridin-3-yl)-hydroxy-methyl]-2,4-difluoro-phenyl}-carbamic acid benzyl ester (6)

Into a round bottom flask was added 5-chloro-1H-pyrrolo[2,3-b]pyridine (5, 0.524 g, 3.43 mmol) in 5.00 mL of metha-nol. Potassium hydroxide (0.800 g, 14.2 mmol) and (2,4-difluoro-3-formyl-phenyl)-carbamic acid benzyl ester (4, 1.02 g, 3.5 mmol) were added and the reaction mixture was stirred overnight. The reaction mixture was poured into 1N hydrochloric acid and extracted with ethyl acetate. The organic layer was washed with brine, dried over sodium sulfate, filtered and the filtrate concentrated under vacuum and crystallized from ethyl acetate to give the desired compound (6, 710 mg, 46%). MS (ESI) [M+H$^+$]$^+$=444.

Step 4—Preparation of [3-(5-chloro-1H-pyrrolo[2,3-b]pyridine-3-carbonyl)-2,4-difluoro-phenyl]-carbamic acid benzyl ester (7)

Into a round bottom flask was added {3-[(5-chloro-1H-pyrrolo[2,3-b]pyridin-3-yl)-hydroxy-methyl]-2,4-difluoro-phenyl}-carbamic acid benzyl ester (6, 1.01 g, 2.28 mmol) in 5.00 mL of tetrahydrofuran. Dess-Martin periodinane (1.20 g, 2.89 mmol) was added in portions. The reaction mixture was stirred at room temperature for 10 minutes, then poured into water and extracted with ethyl acetate. The organic layer was washed with brine, dried over sodium sulfate, filtered and the filtrate concentrated under vacuum and purified by silica gel chromatography to give the desired compound (7, 914 mg, 91%). MS (ESI) [M+H$^+$]$^+$=442.

Step 5—Preparation of (3-amino-2,6-difluoro-phenyl)-(5-chloro-1H-pyrrolo[2,3-b]pyridin-3-yl)-methanone (8)

[3-(5-chloro-1H-pyrrolo[2,3-b]pyridine-3-carbonyl)-2,4-difluoro-phenyl]-carbamic acid benzyl ester (7, 800 mg, 1.81 mmol) was added to 15.00 mL of 10 M sodium hydroxide and warmed to reflux overnight. The reaction mixture was diluted with 30 mL of water and extracted with ethyl acetate. The organic layer was separated, dried, filtered and the filtrate concentrated under vacuum to give the desired compound (8, 450 mg, 81%).

3-(3-Amino-2,6-difluoro-benzoyl)-1H-pyrrolo[2,3-b]pyridine-5-carbonitrile 9, (3-amino-2,6-difluoro-phenyl)-(4-methoxy-1H-pyrrolo[2,3-b]pyridin-3-yl)-methanone 10, and (3-amino-2,6-difluoro-phenyl)-(5-methoxy-1H-pyrrolo[2,3-b]pyridin-3-yl)-methanone 11,

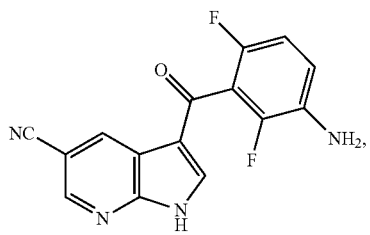

9

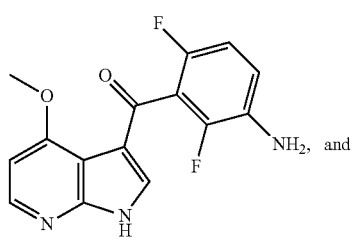

10

-continued

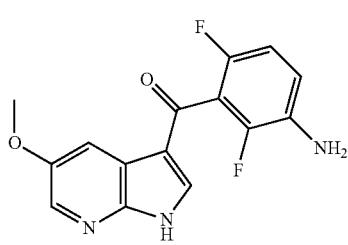

were prepared similarly to the protocol of Scheme 1, replacing 5-chloro-1H-pyrrolo[2,3-b]pyridine 5 with 1H-pyrrolo[2,3-b]pyridine-5-carbonitrile, 4-methoxy-1H-pyrrolo[2,3-b]pyridine, and 5-methoxy-1H-pyrrolo[2,3-b]pyridine, respectively, in Step 3.

3-(3-Amino-2,6-difluoro-benzoyl)-1H-pyrrolo[2,3-b]pyridine-4-carbonitrile 13

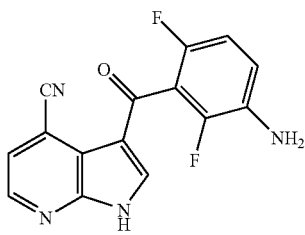

was prepared similarly, replacing 5-chloro-1H-pyrrolo[2,3-b]pyridine 5 with 1H-pyrrolo[2,3-b]pyridine-4-carbonitrile in Step 3, resulting in the methyl ester of the carbamic acid along with the benzyl ester. The methyl ester is carried through Step 4 and the resulting [3-(4-cyano-1H-pyrrolo[2,3-b]pyridine-3-carbonyl)-2,4-difluoro-phenyl]-carbamic acid methyl ester (12) was reacted by the following Step 5a:

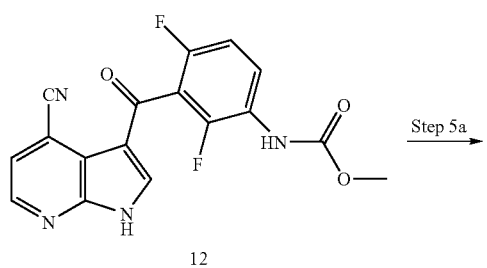

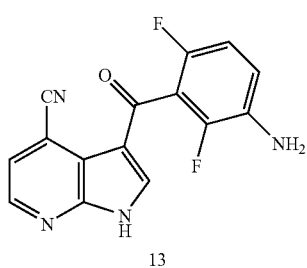

Step 5a—Preparation of 3-(3-amino-2,6-difluoro-benzoyl)-1H-pyrrolo[2,3-b]pyridine-4-carbonitrile (13)

To [3-(4-cyano-1H-pyrrolo[2,3-b]pyridine-3-carbonyl)-2,4-difluoro-phenyl]-carbamic acid methyl ester (12, 0.290 g, 0.814 mmol) in 3.0 mL of acetonitrile at 25° C. under an atmosphere of nitrogen, iodotrimethylsilane (0.431 mL, 3.03 mmol) was added. The reaction was stirred at room temperature overnight, then concentrated and washed with ethyl acetate and hexane to give a brown solid, which was used without further purification (13, 245 mg, 79.1% purity) or further purified. MS (ESI) [M+H$^+$]$^+$=299.0.

(3-Amino-2,6-difluoro-phenyl)-(5-methyl-1H-pyrrolo[2,3-b]pyridin-3-yl)-methanone 17 was prepared in two steps from 2,6-difluoro-3-nitro-benzoyl chloride 14 and 5-methyl-1H-pyrrolo[2,3-b]pyridine 15 as shown in Scheme 1a.

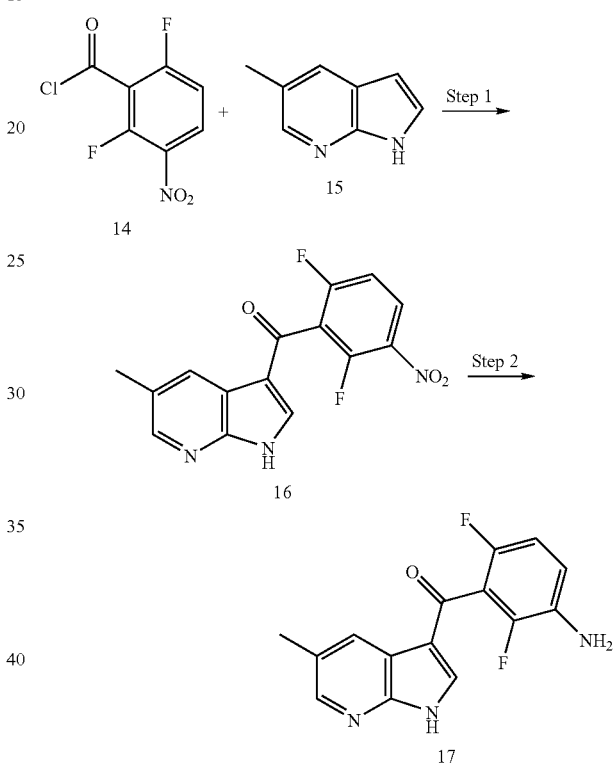

Scheme 1a

Step 1—Preparation of (2,6-difluoro-3-nitro-phenyl)-(5-methyl-1H-pyrrolo[2,3-b]pyridin-3-yl)-methanone (16)

To 5-methyl-1H-pyrrolo[2,3-b]pyridine (15, 2.00 g, 15.1 mmol) and aluminum trichloride (11.6 g, 87.2 mmol), nitromethane (63.1 mL, 1.16 mol) was added, followed by the addition of 2,6-difluoro-3-nitro-benzoyl chloride (14, 3.22 g, 14.5 mmol). The reaction was placed in an oil bath at 45° C. and stirred for 3 days, then cooled to room temperature and 30 mL of methanol was added. The reaction was then diluted with 200 mL of ethyl acetate and 100 mL each of water and 1N hydrochloric acid, resulting in a precipitate that was collected to provide the desired compound (16, 2.761 g). Additional compound was recovered from the organic layer, removing the solvent and purifying by silica gel column chromatography eluting with a gradient of 5 to 70% ethyl acetate in hexanes to provide another 126 mg of compound. MS (ESI) [M+H$^+$]$^+$=317.9.

Step 2—Preparation of (3-amino-2,6-difluoro-phenyl)-(5-methyl-1H-pyrrolo[2,3-b]pyridin-3-yl)-methanone (17)

To (2,6-difluoro-3-nitro-phenyl)-(5-methyl-1H-pyrrolo[2,3-b]pyridin-3-yl)-methanone (16, 1.165 g, 3.672 mmol), 80 mL of ethyl acetate was added, followed by stannous chloride, dihydrate (2.86 g, 12.6 mmol). The suspension was stirred in an oil bath at 65° C. for 18 hours, then poured into a beaker with 200 mL each of water and saturated bicarbonate. The resulting milky suspension was treated with celite, then vacuum filtered through a thin pad of celite. The resulting clear layers of the filtrate were separated and the solvents were removed from the ethyl acetate layer. The resulting material was purified by silica gel column chromatography eluting with a gradient from 30 to 100% ethyl acetate in hexanes to give the desired compound with some impurities. This material was re-purified by silica gel column chromatography eluting with a gradient from 1 to 60% methanol in dichloromethante to give the desired compound (17, 760 mg). $^1$H NMR was consistent with the desired compound structure. MS (ESI) [M+H$^+$]$^+$=288.5.

(3-Amino-2,6-difluoro-phenyl)-(4-chloro-1H-pyrrolo[2,3-b]pyridin-3-yl)-methanone 18

18

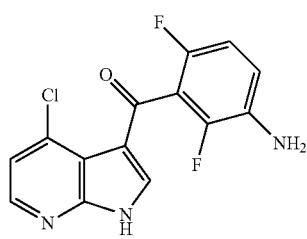

was prepared similarly to the protocol of Scheme 1a, replacing 5-methyl-1H-pyrrolo[2,3-b]pyridine 15 with 4-chloro-1H-pyrrolo[2,3-b]pyridine in Step 1, and in Step 1a, the nitro compound is reduced in ethanol using iron instead of stannous chloride, and the reaction is carried out at 85° C. MS (ESI) [M+H$^+$]$^+$=308.4.

(3-Amino-2,6-difluoro-phenyl)-(5-iodo-1H-pyrrolo[2,3-b]pyridin-3-yl)-methanone 19

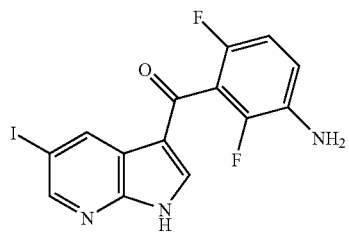

was prepared similarly to the protocol of Scheme 1a, replacing 5-methyl-1H-pyrrolo[2,3-b]pyridine 15 with 5-iodo-1H-pyrrolo[2,3-b]pyridine in Step 1. MS (ESI) [M+H$^+$]$^+$=399.9. This was reacted further to provide (3-amino-2,6-difluoro-phenyl)-[5-(2-methoxy-pyrimidin-5-yl)-1H-pyrrolo[2,3-b]pyridin-3-yl]-methanone 21 via the following Step 3a:

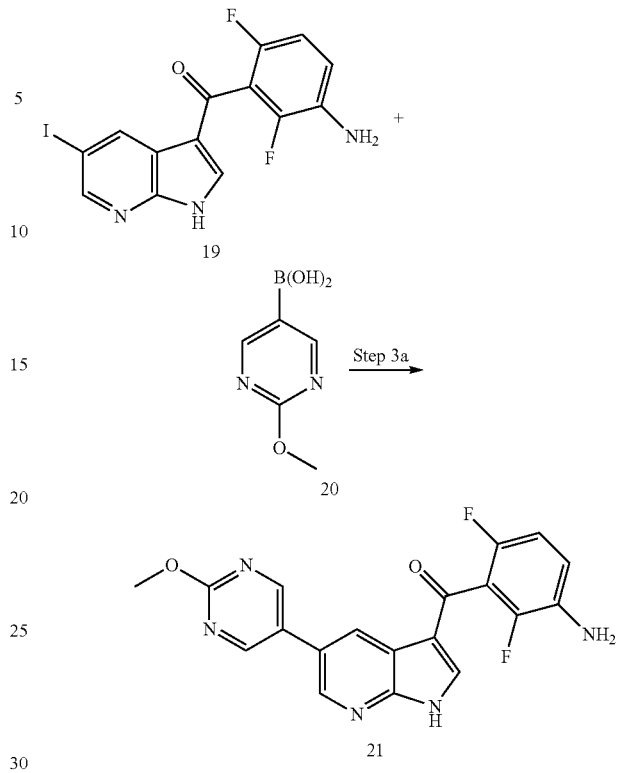

Step 3a—Preparation of (3-amino-2,6-difluoro-phenyl)-[5-(2-methoxy-pyrimidin-5-yl)-1H-pyrrolo[2,3-b]pyridin-3-yl]-methanone (21)

In a microwave vial, (3-amino-2,6-difluoro-phenyl)-(5-iodo-1H-pyrrolo[2,3-b]pyridin-3-yl)-methanone (19, 1.36 g, 3.41 mmol), 2-methoxy-pyrimidine-5-boronic acid (20, 1.05 g, 6.81 mmol), and [1,1'-bis(diphenylphosphino)ferrocene]dichloropalladium(II) (0.25 g, 0.34 mmol) were mixed in 22 mL of 1.00 M potassium carbonate in water and 18 mL of acetonitrile. The resulting mixture was heated at 160° C. in the microwave for 15 minutes. The resulting mixture was filtered through a thin layer of celite, and the celite bed was washed with a mixture of water and ethyl acetate. The two layers of the filtrate were separated, and the aqueous layer was extracted with ethyl acetate. The combined organic layers were washed with brine, dried over sodium sulfate, filtered, and the filtrate concentrated under vacuum. The residue was purified by flash silica gel chromatography eluting with ethyl acetate and dichloromethane to provide the desired compound (21, 0.567 g). MS (ESI) [M+H$^+$]$^+$=382.1.

(3-Amino-2-fluoro-phenyl)-(5-bromo-1H-pyrrolo[2,3-b]pyridin-3-yl)-methanone 22

22

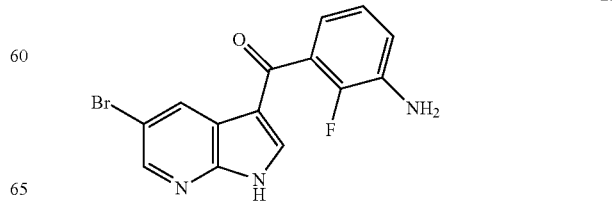

was prepared similarly to the protocol of Scheme 1a, replacing 5-methyl-1H-pyrrolo[2,3-b]pyridine 15 with 5-bromo-1H-pyrrolo[2,3-b]pyridine and replacing 2,6-difluoro-3-nitro-benzoyl chloride 14 with 2-fluoro-3-nitro-benzoyl chloride in Step 1. MS (ESI) [M+H⁺]⁺=334.3 and 336.3. This was reacted further to provide (3-amino-2-fluoro-phenyl)-(5-cyano-1H-pyrrolo[2,3-b]pyridin-3-yl)-methanone 23 via the following Step 3b:

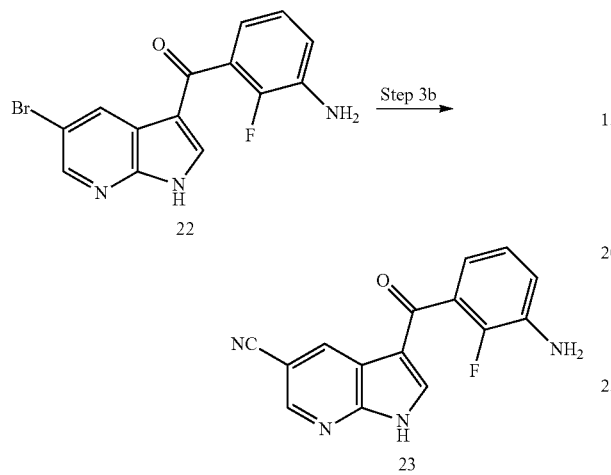

Step 3—Preparation of (3-amino-2-fluoro-phenyl)-(5-cyano-1H-pyrrolo[2,3-b]pyridin-3-yl)-methanone (23)

To (3-amino-2-fluoro-phenyl)-(5-bromo-1H-pyrrolo[2,3-b]pyridin-3-yl)-methanone (22, 1.080 g, 3.232 mmol) in a vial, N,N-dimethylacetamide (2.90 mL, 31.2 mmol) was added. The suspension was degassed by bubbling with argon and zinc powder (0.032 g, 0.48 mmol), 1,1'-bis(diphenylphosphino)ferrocene (0.0568 g, 0.102 mmol), zinc cyanide (0.223 g, 1.90 mmol), and tris(dibenzylideneacetone)dipalladium (0) (0.053 g, 0.052 mmol) were added at room temperature under argon. The mixture was heated to 120° C., resulting in most of the solid dissolving, and the mixture was heated at 120° C. for 2 hours, then cooled to 100° C. and 8 mL of water was added and the reaction mixture cooled to room temperature. The reaction mixture was extracted with ethyl acetate and saturated sodium chloride in water. The organic layer was washed with water and brine, then dried with magnesium sulfate, filtered and the filtrate concentrated under vacuum. The residue was suspended in acetonitrile and sonicated for 30 minutes, after which the precipitated material was collected by filtration to provide the desired compound as a tan solid (23, 613 mg). Additional material was recovered from the filtrate by silica gel chromatography eluting with ethyl acetate and hexanes, the appropriate fractions were combined and the solvent removed to provide an additional 42 mg. MS (ESI) [M+H⁺]⁺=280.9.

Example 2

Synthesis of 5-ethynyl-1H-pyrrolo[2,3-b]pyridine 27

5-Ethynyl-1H-pyrrolo[2,3-b]pyridine 27 was synthesized in two steps from 5-iodo-1H-pyrrolo[2,3-b]pyridine 24 as shown in Scheme 2.

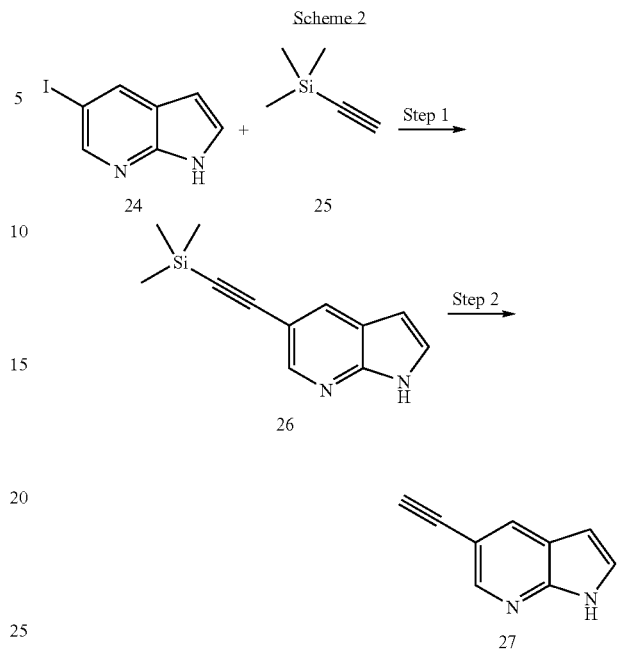

Step 1—Preparation of 5-trimethylsilanylethynyl-1H-pyrrolo[2,3-b]pyridine (26)

5-Iodo-1H-pyrrolo[2,3-b]pyridine (24, 0.303 g, 1.22 mmol), (trimethylsilyl)acetylene (25, 0.210 mL, 1.46 mmol), bis(triphenylphosphine)palladium(II) chloride (0.039 g, 0.055 mmol), and copper(I) iodide (0.0019 g, 0.010 mmol) were dissolved in triethylamine (19 mL, 0.14 mol) under an atmosphere of nitrogen. The resulting mixture was heated to 60° C. and stirred under an atmosphere of nitrogen for 16 hours. The triethylamine was removed under vacuum, 30 mL of water was added to the residue, and it was extracted with 2×20 mL with ether. The combined organic layers were washed with brine and dried over sodium sulfate. Solids were filtered out and the filtrate was concentrated under vacuum. The crude material was purified by silica gel flash chromatography, eluting with ethyl acetate and dichloromethane. The appropriate fractions were combined and the solvents removed under vacuum to provide the desired compound as a solid (26, 0.237 g). MS (ESI) [M+H⁺]⁺=215.3.

Step 2—Preparation of 5-ethynyl-1H-pyrrolo[2,3-b]pyridine (27)

5-Trimethylsilanylethynyl-1H-pyrrolo[2,3-b]pyridine (26, 0.235 g, 1.10 mmol) was dissolved in 16 mL of methanol, and potassium carbonate (0.0152 g, 0.110 mmol) was added. The reaction was stirred for 2 hours at room temperature, then concentrated under vacuum, and the residue was dissolve in dichloromethane, dried over sodium sulfate. Solids were filtered out and the filtrate was concentrated under vacuum. The crude material was purified by silica gel flash chromatography, eluting with ethyl acetate and hexane. The appropriate fractions were combined and the solvents removed under vacuum to provide the desired compound as a solid (27, 0.155 g). MS (ESI) [M+H⁺]⁺=143.3.

Example 3

Synthesis of 5-(3-methoxy-prop-1-ynyl)-1H-pyrrolo[2,3-b]pyridine 32

5-(3-Methoxy-prop-1-ynyl)-1H-pyrrolo[2,3-b]pyridine 32 was synthesized in three steps from 5-iodo-1H-pyrrolo[2,3-b]pyridine 24 as shown in Scheme 3.

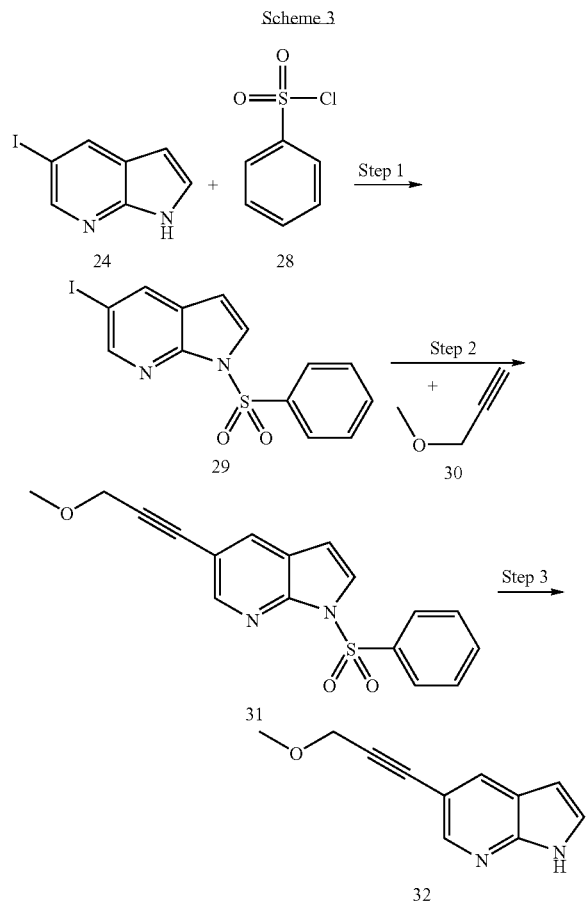

Step 1—Preparation of 1-benzenesulfonyl-5-iodo-1H-pyrrolo[2,3-b]pyridine (29)

5-Iodo-1H-pyrrolo[2,3-b]pyridine (24, 0.521 g, 2.13 mmol), tetra-N-butylammonium bromide (0.0689 g, 0.214 mmol), and 5.00 M sodium hydroxide in water (5.50 mL, 0.0275 mol) were combined in a round bottom flask. Benzenesulfonyl chloride (28, 0.327 mL, 2.56 mmol) in 5.0 mL of tetrahydrofuran was added dropwise at room temperature. The reaction was stirred at room temperature overnight and the two layers were separated. The aqueous layer was washed with ethyl acetate and the combined organic layers were washed with 1M aqueous sodium bicarbonate followed by water. The organic layer was washed with brine and dried over anhydrous sodium sulfate, then filtered and the filtrate concentrated. The crude material was purified by silica gel flash chromatography eluting with ethyl acetate and dichloromethane. The appropriate fractions were combined and the solvents removed under vacuum to provide the desired compound (29, 0.702 g).

Step 2—Preparation of 1-benzenesulfonyl-5-(3-methoxy-prop-1-ynyl)-1H-pyrrolo[2,3b]pyridine (31)

1-Benzenesulfonyl-5-iodo-1H-pyrrolo[2,3-b]pyridine (29, 0.482 g, 1.23 mmol), 3-methoxy-propyne (30, 0.127 mL, 1.48 mmol), bis(triphenylphosphine)palladium(II) chloride (0.039 g, 0.056 mmol), and copper(I) iodide (0.0020 g, 0.010 mmol) were dissolved in 19 mL of triethylamine under an atmosphere of nitrogen. The resulting mixture was heated to 60° C. and stirred under an atmosphere of nitrogen for 16 hours. The triethylamine was removed under vacuum and 30 mL of water was added to the residue, and extracted with 2×20 mL of ether. The combined organic layers were washed with brine and dried over sodium sulfate, filtered and the filtrate concentrated under vacuum. The crude material was purified by silica gel flash chromatography eluting with ethyl acetate and dichloromethane. The appropriate fractions were combined and the solvents removed under vacuum to provide the desired compound.

Step 3—Preparation of 5-(3-methoxy-prop-1-ynyl)-1H-pyrrolo[2,3-b]pyridine (32)

Under an atmosphere of nitrogen 1-benzenesulfonyl-5-(3-methoxy-prop-1-ynyl)-1H-pyrrolo[2,3-b]pyridine (31, 0.541 g, 1.66 mmol) was dissolved in 13 mL of tetrahydrofuran and 1.00 M tetra-n-butylammonium fluoride in 9.12 mL of tetrahydrofuran was added. The resulting solution was stirred for three hours at room temperature under an atmosphere of nitrogen. The reaction was quenched with water and the two layers were separated. The aqueous layer was extracted with ethyl acetate and the combined organic layers were washed with brine and dried over anhydrous sodium sulfate, then filtered and the filtrate concentrated under vacuum. The crude material was purified by silica gel flash chromatography eluting with ethyl acetate and dichloromethane. The appropriate fractions were combined and the solvents removed under vacuum to provide the desired compound (32, 0.215 g).

Diethyl-[3-(1H-pyrrolo[2,3-b]pyridin-5-yl)-prop-2-ynyl]-amine 33

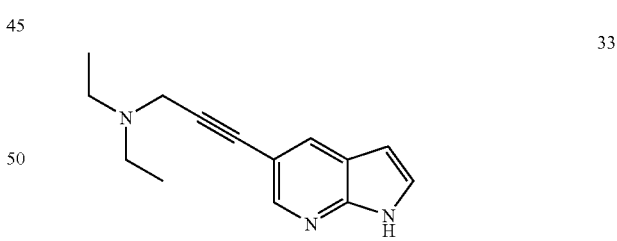

was prepared similarly to the protocol of Scheme 3, replacing 3-methoxy-propyne 30 with diethyl-prop-2-ynyl-amine in Step 2.

Example 4

Synthesis of 5-(1H-pyrrolo[2,3-b]pyridin-5-yl)-pyridine-2-carboxylic acid ethylamide 38

5-(1H-Pyrrolo[2,3-b]pyridin-5-yl)-pyridine-2-carboxylic acid ethylamide 38 was synthesized in two steps from 5-bromo-pyridine-2-carboxylic acid 34 as shown in Scheme 4.

Scheme 4

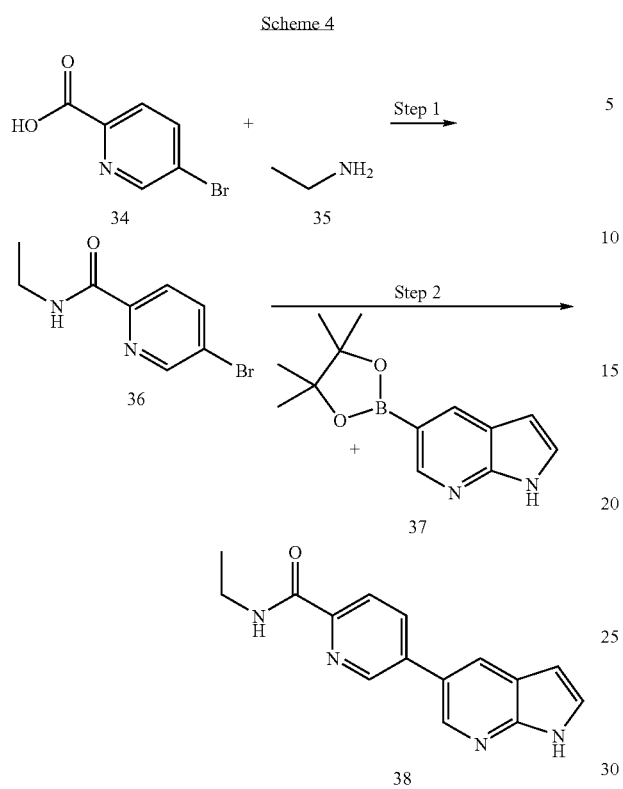

Step 1—Preparation of 5-bromo-pyridine-2-carboxylic acid ethylamide (36)

5-Bromo-pyridine-2-carboxylic acid (34, 0.417 g, 2.06 mmol) was dissolved in 19 mL of tetrahydrofuran. N-(3-Dimethylaminopropyl)-N'-ethylcarbodiimide hydrochloride (0.633 g, 3.30 mmol), N,N-diisopropylethylamine (1.81 mL, 10.4 mmol), and 1-hydroxybenzotriazole (0.363 g, 2.68 mmol) were added, followed by 2.00 M ethylamine in tetrahydrofuran (35, 1.20 mL, 2.40 mmol). The reaction mixture was stirred overnight at room temperature, after which 1.5 mL of dimethylformamide was added and stirred for another 4 hours. The resulting mixture was poured into water and extracted with ethyl acetate. The combined organic layers were washed with brine, dried over anhydrous sodium sulfate and filtered. The filtrate was concentrated under vacuum. The crude material was purified by silica gel flash chromatography. The appropriate fractions were combined and the solvents removed under vacuum to provide the desired compound (36, 163 mg). MS (ESI) [M+H$^+$]$^+$=229.29, 231.3.

Step 2—Preparation of 5-(1H-pyrrolo[2,3-b]pyridin-5-yl)-pyridine-2-carboxylic acid ethylamide (38)

5-(4,4,5,5-Tetramethyl-[1,3,2]dioxaborolan-2-yl)-1H-pyrrolo[2,3-b]pyridine (37, 0.424 g, 1.74 mmol), 5-bromo-pyridine-2-carboxylic acid ethylamide (36, 0.159 g, 0.694 mmol), and tetrakis(triphenylphosphine)palladium(0) (0.016 g, 0.014 mmol) were mixed in 1.00 M potassium carbonate in water (4.2 mL, 4.2 mmol). The reaction mixture was heated at 80° C. overnight. The two layers were separated, and the aqueous layer was extracted with ethyl acetate. The combined organic layers were washed with brine, dried over anhydrous sodium sulfate and filtered. The filtrate was concentrated under vacuum. The crude material was purified by silica gel flash chromatography. The appropriate fractions were combined and the solvents removed under vacuum to provide the desired compound (38, 200 mg). MS (ESI) [M+H$^+$]$^+$=267.2.

5-(1H-Pyrrolo[2,3-b]pyridin-5-yl)-pyridine-2-carboxylic acid methylamide 39, and 5-(1H-pyrrolo[2,3-b]pyridin-5-yl)-pyridine-2-carboxylic acid cyclopropylamide 40,

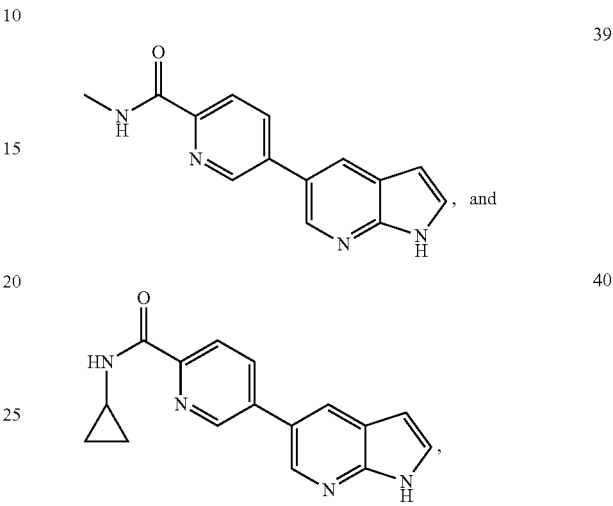

were prepared following the protocol of Scheme 4, replacing ethylamine 35 with methylammonium chloride and cycloalkylamine, respectively in Step 1. MS (ESI) [M+H$^+$]$^+$=253.1 (39), and 279.1 (40).

Example 5

Synthesis of 5-[6-(3-methoxy-propyl)-pyridin-3-yl]-1H-pyrrolo[2,3-b]pyridine 44

5-[6-(3-Methoxy-propyl)-pyridin-3-yl]-1H-pyrrolo[2,3-b]pyridine 44 was synthesized in three steps from 2,5-dibromo-pyridine 41 as shown in Scheme 5.

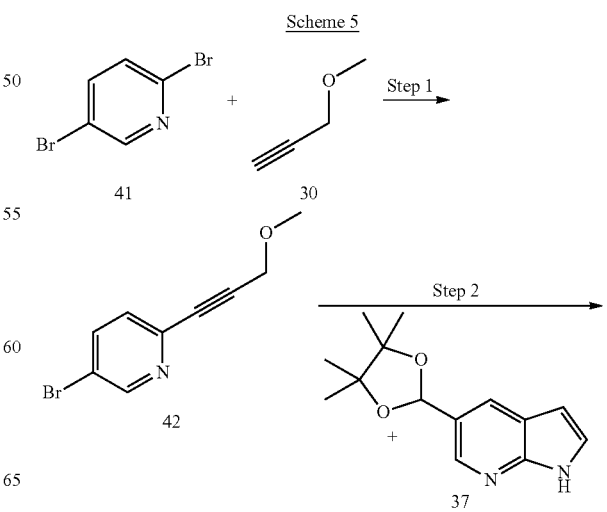

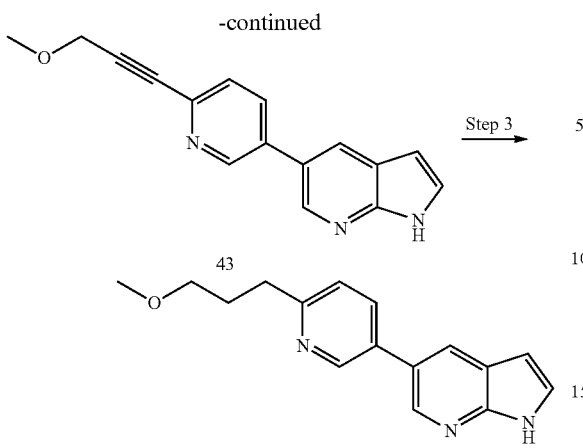

Step 1—Preparation of 5-bromo-2-(3-methoxy-prop-1-ynyl)-pyridine (108)

A solution of 2,5-dibromo-pyridine (41, 4.64 g, 19.6 mmol), 3-methoxy-propyne (30, 1.66 mL, 19.7 mmol), and copper(I) iodide (0.084 g, 0.44 mmol) in 61.6 mL of triethylamine was purged with nitrogen, and bis(triphenylphosphine)palladium(II) chloride (0.31 g, 0.44 mmol) was added at 0° C. The resulting mixture was stirred at 0° C. for 1 hour, then at room temperature for 1 hour. The reaction mixture was diluted with ethyl acetate, then washed with water and brine. The organic layer was dried with anhydrous sodium sulfate, filtered and the filtrate concentrated under vacuum. The crude material was purified by silica gel flash chromatography eluting with ethyl acetate and hexane. The appropriate fractions were combined and the solvents removed under vacuum to provide the desired compound (42, 2.64 g).

Step 2—Preparation of 5-[6-(3-methoxy-prop-1-ynyl)-pyridin-3-yl]-1H-pyrrolo[2,3-b]pyridine (43)

5-(4,4,5,5-Tetramethyl-[1,3,2]dioxaborolan-2-yl)-1H-pyrrolo[2,3-b]pyridine (37, 0.998 g, 4.09 mmol), 5-bromo-2-(3-methoxy-prop-1-ynyl)-pyridine (42, 0.616 g, 2.72 mmol), and tetrakis(triphenylphosphine)palladium(0) (0.157 g, 0.136 mmol) were mixed in 8.2 mL of 1.00 M potassium carbonate in water (8.2 mmol) and 22 mL of tetrahydrofuran. The resulting mixture was heated at 80° C. Ethyl acetate and water were added, and the two layers were separated. The aqueous layer was extracted with ethyl acetate. The combined organic layers were washed with brine, dried over sodium sulfate, filtered, and the filtrate concentrated under vacuum. The crude material was purified by silica gel flash chromatography. The appropriate fractions were combined and the solvents removed under vacuum to provide the desired compound (43, 565 mg). MS (ESI) [M+H⁺]⁺=264.3.

Step 3—Preparation of 5-[6-(3-methoxy-propyl)-pyridin-3-yl]-1H-pyrrolo[2,3-b]pyridine (44)

5-[6-(3-Methoxy-prop-1-ynyl)-pyridin-3-yl]-1H-pyrrolo[2,3-b]pyridine (43, 0.534 g, 2.03 mmol) was dissolved in 8.1 mL of methanol. Palladium hydroxide (0.028 g, 0.20 mmol) was added, and the resulting mixture was stirred under an atmosphere of hydrogen for a few hours, then filtered through a bed of celite. The filtrate was concentrated under vacuum. The crude material was purified by silica gel flash chromatography eluting with ethyl acetate and hexane. The appropriate fractions were combined and the solvents removed under vacuum to provide the desired compound (44, 419 g). MS (ESI) [M+H⁺]⁺=268.3.

Diethyl-{3-[5-(1H-pyrrolo[2,3-b]pyridin-5-yl)-pyridin-2-yl]-prop-2-ynyl}-amine 45

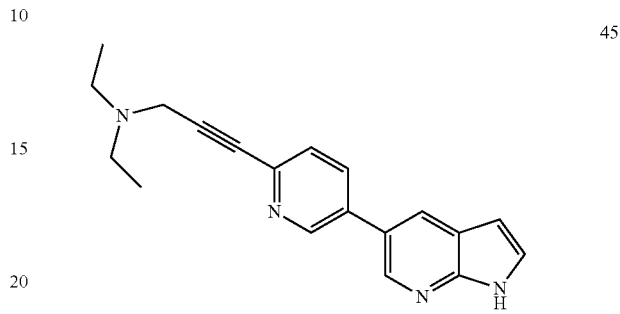

was prepared following the protocol of Scheme 5, steps 1 and 2, replacing 3-methoxy-propyne 30 with diethyl-prop-2-ynyl-amine in step 1. MS (ESI) [M+H⁺]⁺=305.3.

Example 6

Synthesis of dimethyl-{3-[5-(1H-pyrrolo[2,3-b]pyridin-5-yl)-pyrimidin-2-yloxy]-propyl}-amine 49

Dimethyl-{3-[5-(1H-pyrrolo[2,3-b]pyridin-5-yl)-pyrimidin-2-yloxy]-propyl}-amine 49 was synthesized in two steps from 5-bromo-2-chloro-pyrimidine 46 as shown in Scheme 6.

Scheme 6

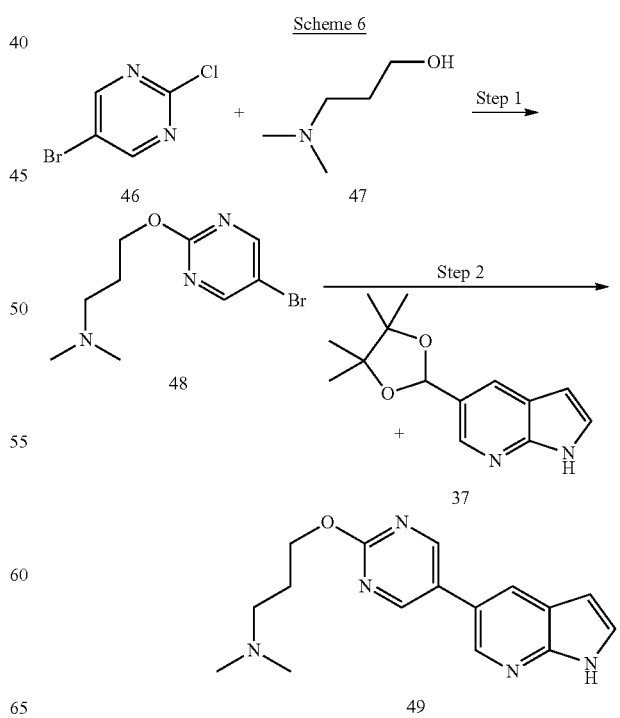

Step 1—Preparation of [3-(5-bromo-pyrimidin-2-yloxy)-propyl]-dimethyl-amine (48)

To a solution of 3-(dimethylamino)-1-propanol (47, 3.45 mL, 2.84 mmol) in 10 mL of dry tetrahydrofuran, sodium hydride (0.0784 g, 3.10 mmol) was added at room temperature. After 15 minutes, 5-bromo-2-chloro-pyrimidine (46, 0.500 g, 2.58 mmol) was added and the mixture was stirred at room temperature for 16 hours. To this, ~500 µL of saturated ammonium chloride was added and the reaction was treated with ethyl acetate and filtered. The solvents were removed from the filtrate under vacuum, then added diethyl ether, removed solvent under vacuum and repeated twice. The resulting residue was taken up with tetrahydrofuran/acetonitrile and filtered. Silica gel was added to the filtrate and solvents removed under vacuum, then purified by silica gel chromatography eluting with 1 to 6% methanol in dichloromethane, followed with 20% methanol in dichloromethane. The appropriate fractions were combined and the solvents removed under vacuum to provide the desired compound (48, 259 mg). MS (ESI) [M+H$^+$]$^+$=261.9.

Step 2—Preparation of dimethyl-{3-[5-(1H-pyrrolo[2,3-b]pyrimidin-5-yl)-pyrimidin-2-yloxy]-propyl}-amine (49)

Into a round bottom flask, [3-(5-bromo-pyrimidin-2-yloxy)-propyl]-dimethyl-amine (48, 259 mg, 0.996 mmol), 5-(4,4,5,5-tetramethyl-[1,3,2]dioxaborolan-2-yl)-1H-pyrrolo[2,3-b]pyridine (37, 364 mg, 1.49 mmol), tetrakis(triphenylphosphine)palladium(0) (57.5 mg, 0.0498 mmol), and tetra-n-butylammonium iodide (37 mg, 0.10 mmol) were mixed in 6 mL of 1.00 M potassium carbonate in water (6.0 mmol) and 12 mL of tetrahydrofuran. The resulting mixture was heated at 70° C. overnight. The two layers were separated and the aqueous layer was extracted with ethyl acetate. The organic layers were washed with saturated aqueous sodium bicarbonate, water, and brine, dried over anhydrous sodium sulfate, filtered, and the filtrate concentrated under vacuum. The crude material was purified by silica gel chromatography, eluting with up to 30% methanol in dichloromethane. The appropriate fractions were combined and concentrated under vacuum, then further purified on a new column eluting with 15% methanol in ethyl acetate with 8% triethylamine. The appropriate fractions were combined and concentrated under vacuum to provide the desired compound as an off-white solid (49, 76 mg). MS (ESI) [M+H$^+$]$^+$=298.0.

Example 7

Synthesis of propane-1-sulfonic acid [3-(5-bromo-1H-pyrrolo[2,3-b]pyridine-3-carbonyl)-2,4-difluoro-phenyl]-amide 56

Propane-1-sulfonic acid [3-(5-bromo-1H-pyrrolo[2,3-b]pyridine-3-carbonyl)-2,4-difluoro-phenyl]amide 56 was synthesized in five steps from 2,4-difluoro-phenylamine 1 as shown in Scheme 7.

Scheme 7

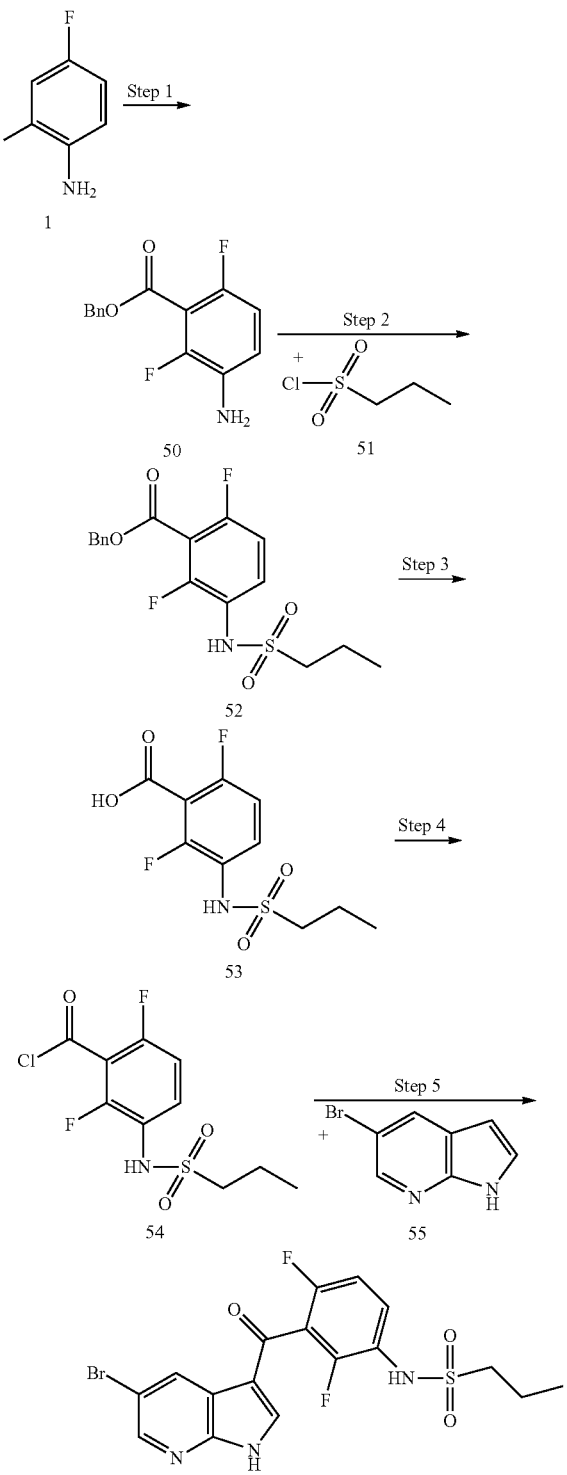

Step 1—Preparation of 3-amino-2,6-difluoro-benzoic acid benzyl ester (50)

To 2,4-difluoro-phenylamine (1, 5.11 mL, 50.7 mmol) in tetrahydrofuran (250 mL), cooled with dry ice/acetone bath under an atmosphere of nitrogen, was added n-butyllithium (1.60 M in hexane, 34.0 mL, 54.4 mmol) slowly. After 30 minutes, 1,2-Bis-(chloro-dimethyl-silanyl)-ethane (11.5 g, 53.4 mmol) dissolved in tetrahydrofuran (40.0 mL) was added to the reaction slowly. After 1 hour, n-butyllithium (1.60 M in hexane, 31.9 mL, 51.0 mmol) was added slowly to the reaction. The reaction was stirred at −78° C. for 30 minutes and then allowed to warm to room temperature over 40 minutes. The reaction was cooled to −78° C., followed by addition of n-butyllithium (1.60 M in hexane, 35.1 mL, 56.2 mmol) slowly. After 70 minutes, benzyl chloroformate (7.97 mL, 55.8 mmol) was added to the reaction. The reaction mixture was stirred at −78° C. overnight followed by addition of 2 N HCl (120 mL). The reaction was allowed to warm to room temperature for 2 hours. The organic layer was separated. The aqueous layer was basified with potassium carbonate and extracted with ethyl acetate. The organic layers were combined and washed with brine, dried over anhydrous sodium sulfate, filtrated and concentrated. The desired compound was isolated by silica gel column chromatography (ethyl acetate/hexane 20%) to give a colorless oil (50, 10.6 g, 79.7%). MS (ESI) [M+H$^+$]$^+$=264.1.

Step 2—Preparation of 2,6-difluoro-3-(propane-1-sulfonylamino)-benzoic acid benzyl ester (52)

To 3-amino-2,6-difluoro-benzoic acid benzyl ester (50, 6.00 g, 22.8 mmol) in methylene chloride (150 mL) was added pyridine (2.76 mL, 34.2 mmol) and propane-1-sulfonyl chloride (51, 3.80 mL, 33.8 mmol). The reaction was stirred at room temperature overnight. Then the reaction was poured into water, and extracted with ethyl acetate. The organic layer was washed with brine, dried over anhydrous sodium sulfate, filtrated and concentrated. The desired compound was isolated with silica gel column chromatography to give a colorless oil (52, 7.0 g, 83.1%). MS (ESI) [M+H$^+$]$^+$=370.1.

Step 3—Preparation of 2,6-difluoro-3-(propane-1-sulfonylamino)-benzoic acid (53)

To 2,6-difluoro-3-(propane-1-sulfonylamino)-benzoic acid benzyl ester (52, 2.0 g, mmol) in methanol (30 mL) was added 20% palladium hydroxide on carbon (100 mg). The reaction was stirred under hydrogen at 1 atm for 15 minutes. The reaction was filtered and the filtrate concentrated under vacuum to provide the desired compound.

Step 4—Preparation of 2,6-difluoro-3-(propane-1-sulfonylamino)-benzoyl chloride (54)

To 2,6-difluoro-3-(propane-1-sulfonylamino)-benzoic acid (53, 1.50 g, 5.4 mmol) was added toluene (7.0 mL) and thionyl chloride (15.0 mL, 0.21 mmol). The reaction was heated to reflux for 3 hours. The reaction was concentrated to give crude compound that was used in the next step.

Step 5—Preparation of propane-1-sulfonic acid [3-(5-bromo-1H-pyrrolo[2,3-b]pyridine-3-carbonyl)-2,4-difluoro-phenyl]-amide (56)

To aluminum trichloride (8.89 g, 66.7 mmol) was added methylene chloride (150 mL) under an atmosphere of nitrogen below 5° C. Into this, 5-bromo-1H-pyrrolo[2,3-b]pyridine (55, 1.64 g, 8.34 mmol) in methylene chloride (20 mL) was added. The reaction was stirred for 60.0 minutes and 2,6-difluoro-3-(propane-1-sulfonylamino)-benzoyl chloride (54, 3.50 g, 11.8 mmol) in methylene chloride (20 mL) was added. The reaction was stirred for 6 hours and warmed to room temperature overnight. The reaction mixture was poured into water and extracted with ethyl acetate. The organic layer was dried over anhydrous sodium sulfate, filtrated and concentrated. The desired compound was isolated by silica gel column chromatography (methylene chloride/methanol 5%) to give a white solid (56, 1.2 g, 31.4%). MS (ESI) [M+H$^+$]$^+$=460.0, 462.0.

Example 8

Synthesis of propane-1-sulfonic acid (2,4-difluoro-3-formyl-phenyl)-amide 58

Propane-1-sulfonic acid (2,4-difluoro-3-formyl-phenyl)-amide 58 was synthesized in two steps from 2,4-difluorophenylamine 1 as shown in Scheme 8.

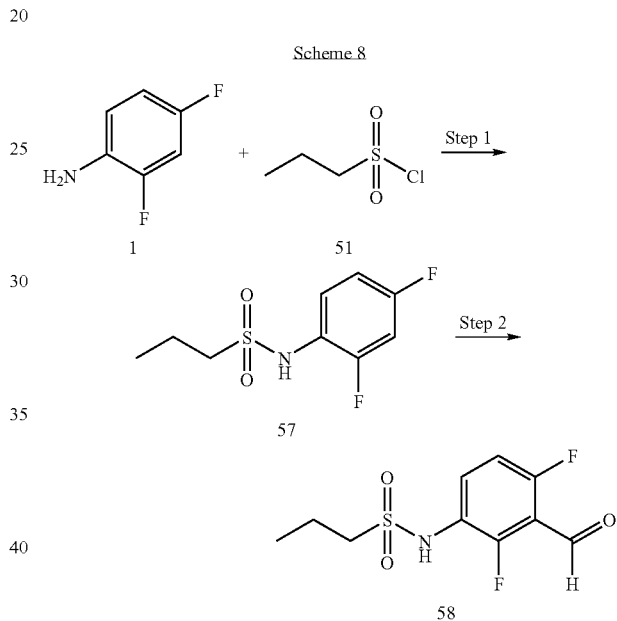

Step 1—Preparation of propane-1-sulfonic acid (2,4-difluoro-phenyl)-amide (57)

To 2,4-difluoro-phenylamine (1, 3.0 mL, 29.8 mmol) in tetrahydrofuran (50 mL) were added triethylamine (9.13 mL, 65.5 mmol) and propane-1-sulfonyl chloride (51, 2.90 mL, 25.8 mmol) under an atmosphere of nitrogen. The reaction was stirred at room temperature overnight. The reaction was poured into 1 M HCl and extracted with ethyl acetate. The organic layer was washed with brine, dried over anhydrous sodium sulfate and filtered. The filtrate was concentrated to give the compound (57, 2.0 g, 28%) that was used in the next step.

Step 2—Preparation of propane-1-sulfonic acid (2,4-difluoro-3-formyl-phenyl)-amide (58)

To propane-1-sulfonic acid (2,4-difluoro-phenyl)-amide (57, 1.5 g, 6.38 mmol) in tetrahydrofuran (10 mL) under an atmosphere of nitrogen, cooled in a −78° C. acetone/dry ice bath was added lithium diisopropylamide (0.80 M in tetrahydrofuran, 24 mL, freshly prepared from n-butyllithium and diisopropylamine). After 30 minutes, N,N-dimethyl-formamide (542 µL, 7.018 mmol) was added dropwise to the reaction. The reaction was stirred for 30 minutes at −78° C. and then allowed to warm to room temperature for 40 minutes. The reaction was poured into water and extracted with ethyl acetate. The organic layer was washed with brine, dried over anhydrous sodium sulfate and filtered. The filtrate was concentrated and purified by silica gel column chromatography eluting with 5% ethyl acetate in hexane to give a light yellow solid (58, 300 mg, 18%). MS (ESI) [M−H$^+$]$^−$=262.3.

2-Methyl-propane-1-sulfonic acid (2,4-difluoro-3-formyl-phenyl)-amide 59

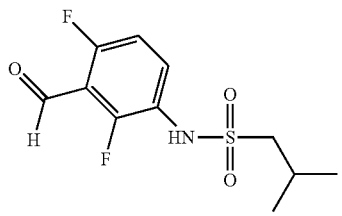

59 was prepared similarly to the protocol of Scheme 8, replacing propane-1-sulfonyl chloride 51 with 2-methyl-propane-1-sulfonyl chloride in Step 1.

Example 9

Synthesis of propane-1-sulfonic acid (2-fluoro-3-formyl-phenyl)-amide 67

Propane-1-sulfonic acid (2-fluoro-3-formyl-phenyl)-amide 67 was synthesized in seven steps from 4-chloro-2-fluoro-phenylamine 60 as shown in Scheme 9.

Scheme 9

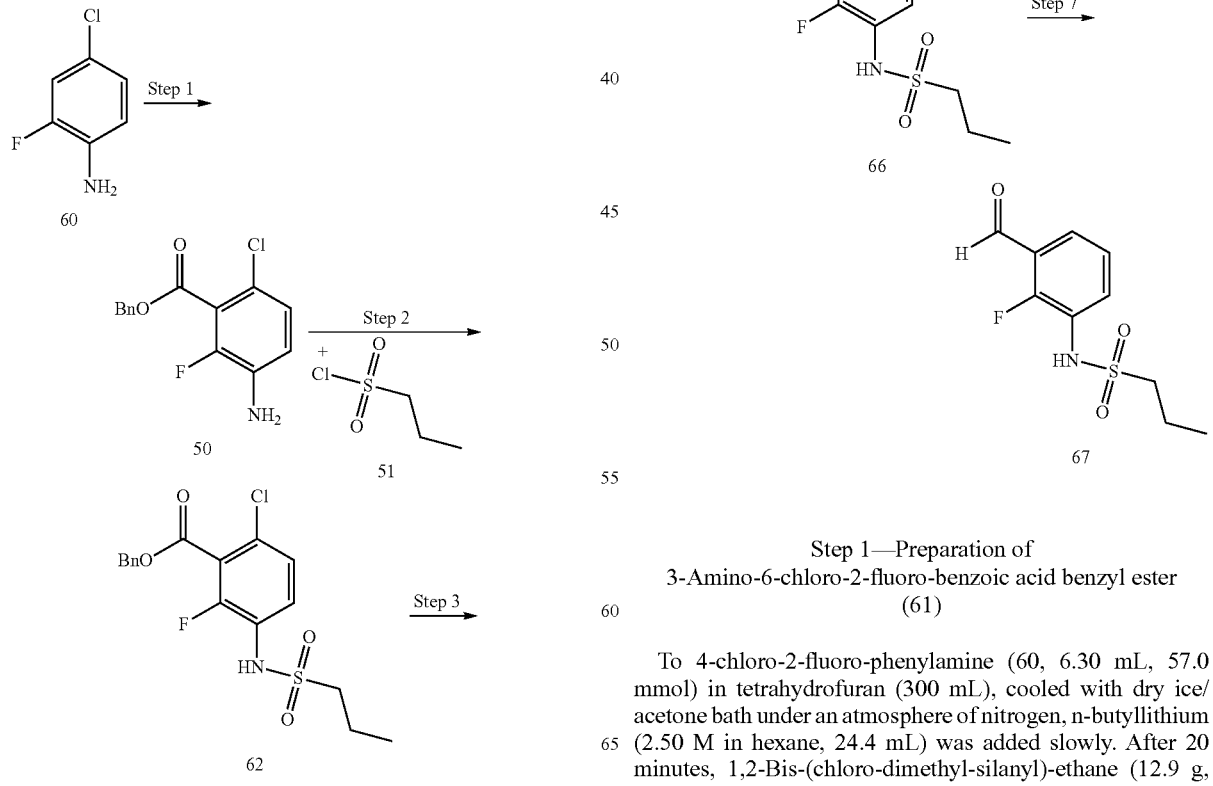

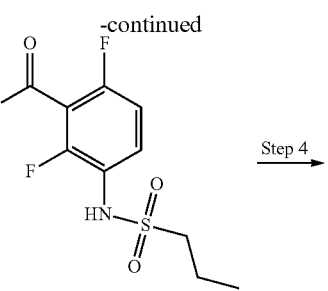

63

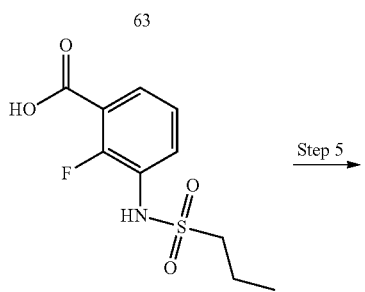

64

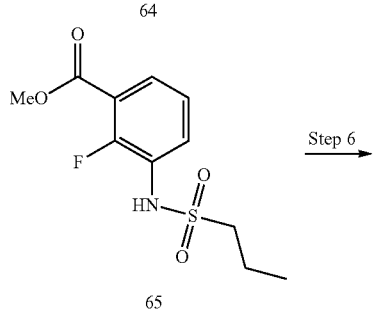

65

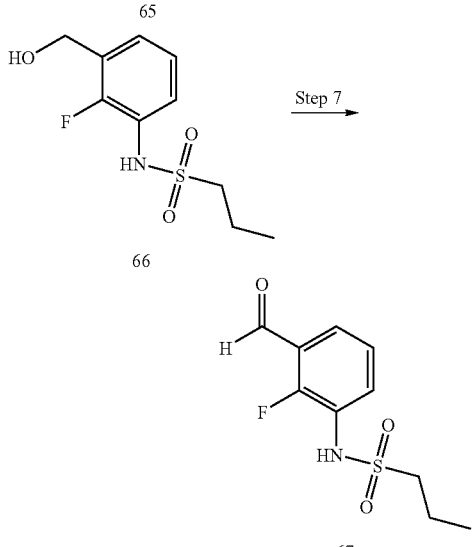

66

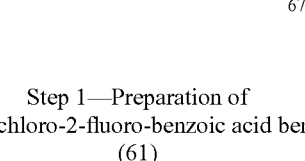

67

Step 1—Preparation of 3-Amino-6-chloro-2-fluoro-benzoic acid benzyl ester (61)

To 4-chloro-2-fluoro-phenylamine (60, 6.30 mL, 57.0 mmol) in tetrahydrofuran (300 mL), cooled with dry ice/acetone bath under an atmosphere of nitrogen, n-butyllithium (2.50 M in hexane, 24.4 mL) was added slowly. After 20 minutes, 1,2-Bis-(chloro-dimethyl-silanyl)-ethane (12.9 g, 60.0 mmol) dissolved in tetrahydrofuran (40.0 mL) was added slowly to the reaction. After 1 hour, n-butyllithium (2.50 M in hexane, 25.0 mL) was added slowly to the reaction. The reaction was stirred at −78° C. for 20 minutes and then allowed to warm to room temperature over 60 minutes. The reaction was cooled to −78° C., followed by addition of n-butyllithium (2.50 M in hexane, 26.0 mL) slowly. After 80 minutes, benzyl chloroformate (10.0 mL, 70.0 mmol) was added to the reaction. The reaction mixture was stirred at −78° C. overnight followed by addition of water (80 mL) and concentrated hydrochloric acid (25 mL). The reaction was allowed to warm to room temperature for 2 hours. The organic layer was separated. The aqueous layer was basified with potassium carbonate and extracted with ethyl acetate. The organic layers were combined and washed with brine, dried over anhydrous sodium sulfate, filtered and concentrated. The desired compound was isolated by silica gel column chromatography (ethyl acetate/hexane 20%) to give a colorless oil (61, 12.5 g, 78.3%). MS (ESI) [M+H$^+$]$^+$=280.0.

Step 2—Preparation of 6-chloro-2-fluoro-3-(propane-1-sulfonylamino)-benzoic acid benzyl ester (62)

To 3-amino-6-chloro-2-fluoro-benzoic acid benzyl ester (61, 1.20 g, 4.3 mmol) in methylene chloride (28 mL) was added pyridine (0.52 mL, 6.4 mmol) and propane-1-sulfonyl chloride (51, 0.685 g, 4.8 mmol). The reaction was stirred at room temperature overnight, then poured into water, and extracted with ethyl acetate. The organic layer was washed with brine, dried over anhydrous sodium sulfate, filtered and concentrated. The desired compound was isolated with silica gel column chromatography to give a colorless oil (62, 960 mg, 58.0%). MS (ESI) [M−H$^+$]$^−$=384.1.

Step 3—Preparation of 6-chloro-2-fluoro-3-(propane-1-sulfonylamino)-benzoic acid (63)

To 6-chloro-2-fluoro-3-(propane-1-sulfonylamino)-benzoic acid benzyl ester (62, 6.00 g, 15.6 mmol) in tetrahydrofuran (100 mL) was added 1.0 M aqueous potassium hydroxide (100 mL). The reaction was heated to reflux overnight. The reaction was poured into water, acidified to pH 2 with 1 N hydrochloric acid and extracted with ethyl acetate. The organic portion was dried over anhydrous sodium sulfate, filtered and concentrated to give a white solid (63, 3.95 g, 85.8%).

Step 4—Preparation of 2-fluoro-3-(propane-1-sulfonylamino)-benzoic acid (64)

To 6-chloro-2-fluoro-3-(propane-1-sulfonylamino)-benzoic acid (63, 0.69 g, 2.3 mmol) in methanol (10 mL) was added 20% palladium hydroxide on carbon (200 mg). The reaction was stirred under hydrogen at 50 psi for 2 hours. The reaction was filtered and concentrated to give the desired compound. MS (ESI) [M−H$^+$]$^−$=260.1.

Step 5—Preparation of 2-fluoro-3-(propane-1-sulfonylamino)-benzoic acid methyl ester (65)

To a 2-fluoro-3-(propane-1-sulfonylamino)-benzoic acid (64, 5.05 g, 0.0193 mol) in methylene chloride (100 mL) was added N,N-dimethylformamide (0.075 mL, 0.97 mmol) under an atmosphere of nitrogen. The reaction was cooled with ice/water, followed by slow addition of Oxalyl chloride (2.00 M of in methylene chloride, 10.8 mL, 21.6 mmol). The reaction mixture was stirred at room temperature for 3.0 hours. The reaction was cooled with ice/water, followed by addition of methanol (36.0 mL, 0.89 mol) slowly. The reaction was stirred at room temperature overnight. The reaction was concentrate and purified with silica gel column chromatography eluting with 30% ethyl acetate in hexane to give a crude white solid 4.0 g.

Step 6—Preparation of Propane-1-sulfonic acid (2-fluoro-3-hydroxymethyl-phenyl)-amide (66)

To 2-fluoro-3-(propane-1-sulfonylamino)-benzoic acid methyl ester (65, 3.80 g, 13.8 mmol) in tetrahydrofuran (133 mL) was added lithium tetrahydroaluminate (1.00 M in tetrahydrofuran, 20.0 mL, 20.0 mmol) under an atmosphere of nitrogen at room temperature. The reaction was stirred at room temperature for 8 hours, followed by addition of 10 g of NaSO$_4$.10H$_2$O. After 12 hours, the reaction was filtered, concentrated and purified with silica gel column chromatography eluting with 5% methanol in methylene chloride to give a white solid (66, 3.0 g, 87.9%).

Step 7—Preparation of propane-1-sulfonic acid (2-fluoro-3-formyl-phenyl)-amide (67)

To propane-1-sulfonic acid (2-fluoro-3-hydroxymethyl-phenyl)-amide (66, 0.20 g, 0.81 mmol) in tetrahydrofuran (5.0 mL) was added Dess-Martin periodinane (0.377 g, 0.89 mmol). The reaction was stirred at room temperature for 10 minutes, then poured into water and extracted with ethyl acetate. The organic layer was dried over anhydrous sodium sulfate, and filtered. The filtrate was concentrated and purified by silica gel column chromatography eluting with 20% ethyl acetate in hexane to give a white solid (67, 100 mg, 50.0%). MS (ESI) [M−H$^+$]$^+$=244.1.

Example 10

Synthesis of 2-methyl-propane-1-sulfonic acid [3-(5-bromo-1H-pyrrolo[2,3-b]pyridine-3-carbonyl)-2,4-difluoro-phenyl]-amide 69

2-Methyl-propane-1-sulfonic acid [3-(5-bromo-1H-pyrrolo[2,3-b]pyridine-3-carbonyl)-2,4-difluoro-phenyl]-amide 69 was synthesized in two steps from 5-bromo-1H-pyrrolo[2,3-b]pyridine 55 as shown in Scheme 10.

Scheme 10

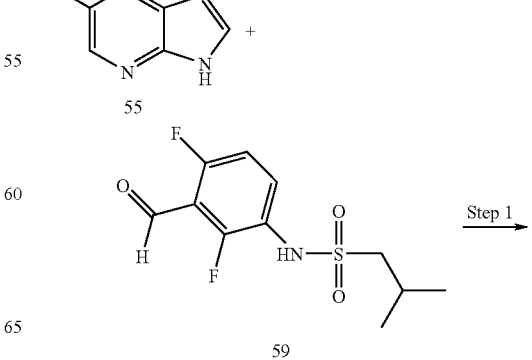

83

-continued

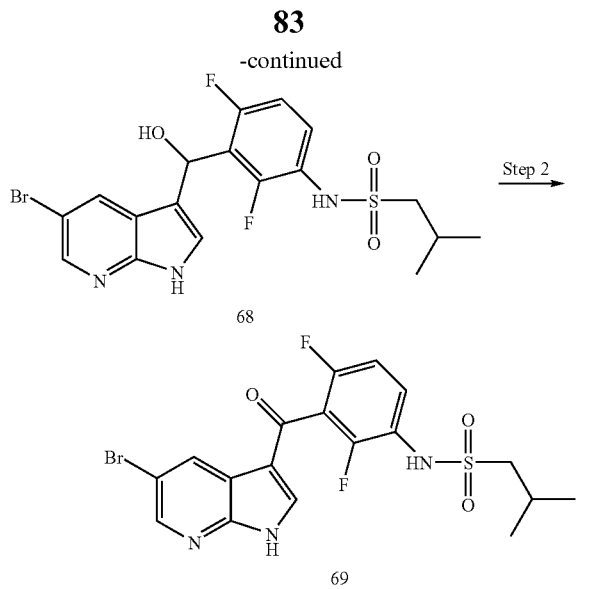

Step 1—Preparation of 2-methyl-propane-1-sulfonic acid {3-[(5-bromo-1H-pyrrolo[2,3-b]pyridin-3-yl)-hydroxy-methyl]-2,4-difluoro-phenyl}-amide (68)

In a reaction vial, 5-bromo-1H-pyrrolo[2,3-b]pyridine (55, 287 mg, 1.46 mmol), 2-methyl-propane-1-sulfonic acid (2,4-difluoro-3-formyl-phenyl)-amide (59, 445 mg, 1.60 mmol) and potassium hydroxide (246 mg, 4.38 mmol) are combined with 7 mL of methanol and stirred at room temperature overnight. The reaction was combined with ethyl acetate and aqueous saturated sodium chloride, and extracted. The organic layer was washed with water, brine, and dried over magnesium sulfate, filtered and the filtrate concentrated under vacuum. The residue was treated with 75 mL of acetonitrile:water 4:1 with 5% trifluoroacetic acid and stirred overnight at room temperature. The reaction was combined with ethyl acetate and aqueous saturated sodium chloride, and extracted. The organic layer was washed with water, brine, and dried over magnesium sulfate, filtered and the filtrate concentrated under vacuum to provide the desired compound (68, 618 mg).

Step 2—Preparation of 2-methyl-propane-1-sulfonic acid [3-(5-bromo-1H-pyrrolo[2,3-b]pyridine-3-carbonyl)-2,4-difluoro-phenyl]-amide (69)

In a round bottom flask, 2-methyl-propane-1-sulfonic acid {3-[(5-bromo-1H-pyrrolo[2,3-b]pyridin-3-yl)-hydroxy-methyl]-2,4-difluoro-phenyl}-amide (68, 618 mg, 1.30 mmol) was dissolved in 20 mL of tetrahydrofuran, and Dess-Martin periodinane (555 mg, 1.31 mmol) was added. The reaction was stirred at room temperature for 30 minutes, then quenched with water and extracted with ethyl acetate. The organic layer was washed with sodium bicarbonate, water, and brine, then dried with magnesium sulfate, filtered and concentrated under vacuum. The resulting material was purified by silica gel column chromatography, eluting with dichloromethane and methanol. Appropriate fractions were collected and concentrated under vacuum to provide the desired compound (69, 257 mg). MS (ESI) [M–H+]⁻=469.9, 471.9.

84

Propane-1-sulfonic acid [2-fluoro-3-(5-iodo-1H-pyrrolo[2,3-b]pyridine-3-carbonyl)-phenyl]-amide 70

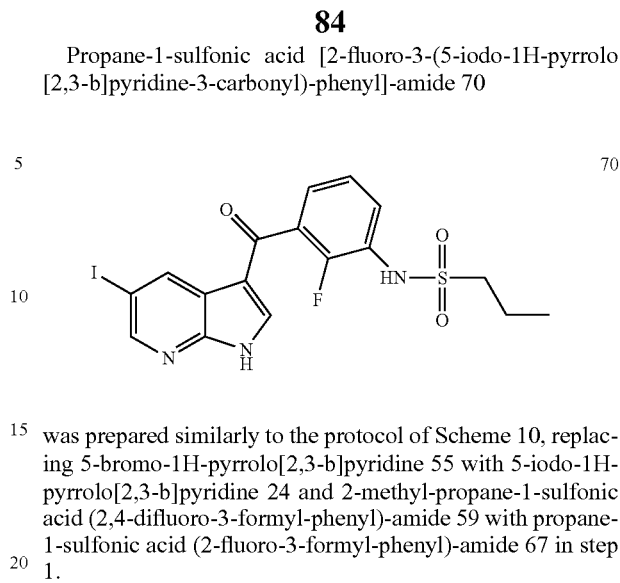

was prepared similarly to the protocol of Scheme 10, replacing 5-bromo-1H-pyrrolo[2,3-b]pyridine 55 with 5-iodo-1H-pyrrolo[2,3-b]pyridine 24 and 2-methyl-propane-1-sulfonic acid (2,4-difluoro-3-formyl-phenyl)-amide 59 with propane-1-sulfonic acid (2-fluoro-3-formyl-phenyl)-amide 67 in step 1.

Example 11

Synthesis of N-{2,4-difluoro-3-(5-methyl-1H-pyrrolo[2,3-b]pyridine-3-carbonyl)-phenyl}-3-fluoro-benzenesulfonamide P-2016

N-[2,4-Difluoro-3-(5-methyl-1H-pyrrolo[2,3-b]pyridine-3-carbonyl)-phenyl]-3-fluoro-benzenesulfonamide P-2016 was synthesized in one step from (3-amino-2,6-difluoro-phenyl)-(5-methyl-1H-pyrrolo[2,3-b]pyridin-3-yl)-methanone 17 as shown in Scheme 11.

Scheme 11

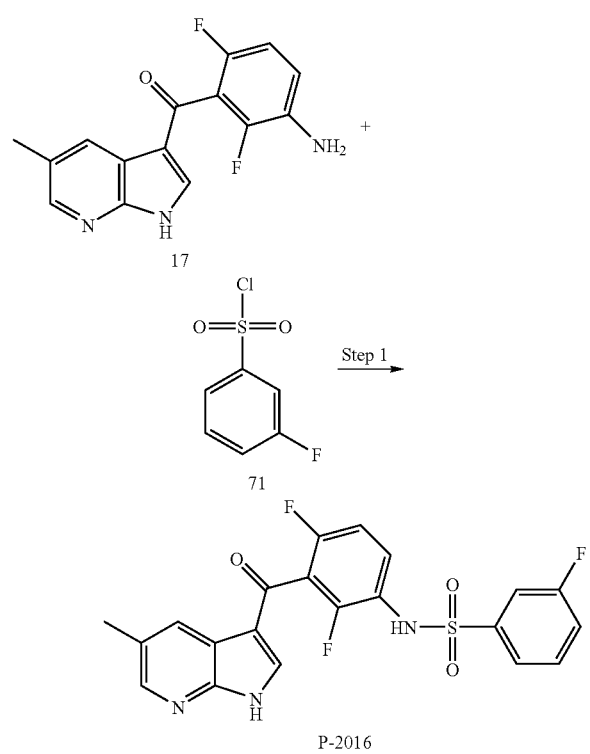

Step 1—Preparation of N-[2,4-difluoro-3-(5-methyl-1H-pyrrolo[2,3-b]pyridine-3-carbonyl)-phenyl]-3-fluoro-benzenesulfonamide (P-2016)

To (3-amino-2,6-difluoro-phenyl)-(5-methyl-1H-pyrrolo[2,3-b]pyridin-3-yl)-methanone (17, 20 mg, 0.07 mmol) in 0.5 mL of tetrahydrofuran and pyridine (50 µL, 0.62 mmol), 4-fluoro-benzenesulfonyl chloride (71, 20.4 mg, 0.105 mmol) was added and the reaction was stirred at room temperature overnight. The mixture was concentrated under vacuum and the crude dry material was dissolved in 0.5 mL of dimethylsulfoxide and purified by reverse phase HPLC, eluting with 0.1% trifluoroacetic acid in water and 0.1% trifluoroacetic acid in acetonitrile, 20-100% acetonitrile over 40 minutes at 20 mL per minute. Appropriate fractions were combined and the solvent removed under reduced pressure to provide the desired compound. MS (ESI) $[M+H^+]^+=445.9$.

Additional compounds were prepared similarly to the protocol of Scheme 11, where optimal reaction conditions may have varied in terms of time and temperature of the reaction, and in chromatography conditions for purification of the desired compounds. The reactions were performed optionally replacing (3-amino-2,6-difluoro-phenyl)-(5-methyl-1H-pyrrolo[2,3-b]pyridin-3-yl)-methanone 17 with 5-(2-methoxy-pyrimidin-5-yl), 5-chloro, 5-cyano, 5-methoxy, 4-methoxy, 4-cyano, or 4-chloro (3-amino-2,6-difluoro-phenyl)-(1H-pyrrolo[2,3-b]pyridin-3-yl)-methanone (prepared as described in Example 1) and/or replacing 4-fluoro-benzenesulfonyl chloride 71 with an appropriate sulfonyl chloride. The following compounds were prepared by this procedure:

N-[3-(5-Chloro-1H-pyrrolo[2,3-b]pyridine-3-carbonyl)-2,4-difluoro-phenyl]-2,5-difluoro-benzenesulfonamide (P-2002),
N-[3-(5-Chloro-1H-pyrrolo[2,3-b]pyridine-3-carbonyl)-2,4-difluoro-phenyl]-2,6-difluoro-benzenesulfonamide (P-2003),
N-[2,4-Difluoro-3-(5-methoxy-1H-pyrrolo[2,3-b]pyridine-3-carbonyl)-phenyl]-2-fluoro-benzenesulfonamide (P-2009),
N-[2,4-Difluoro-3-(5-methoxy-1H-pyrrolo[2,3-b]pyridine-3-carbonyl)-phenyl]-2,5-difluoro-benzenesulfonamide (P-2010),
N-[3-(5-Cyano-1H-pyrrolo[2,3-b]pyridine-3-carbonyl)-2,4-difluoro-phenyl]-2-fluoro-benzenesulfonamide (P-2011),
N-[2,4-Difluoro-3-(5-methyl-1H-pyrrolo[2,3-b]pyridine-3-carbonyl)-phenyl]-2-fluoro-benzenesulfonamide (P-2014),
N-[2,4-Difluoro-3-(5-methyl-1H-pyrrolo[2,3-b]pyridine-3-carbonyl)-phenyl]-2,5-difluoro-benzenesulfonamide (P-2015),
N-[3-(4-Chloro-1H-pyrrolo[2,3-b]pyridine-3-carbonyl)-2,4-difluoro-phenyl]-2-fluoro-benzenesulfonamide (P-2017),
N-[3-(4-Chloro-1H-pyrrolo[2,3-b]pyridine-3-carbonyl)-2,4-difluoro-phenyl]-2,5-difluoro-benzenesulfonamide (P-2018),
N-[3-(4-Chloro-1H-pyrrolo[2,3-b]pyridine-3-carbonyl)-2,4-difluoro-phenyl]-3-fluoro-benzenesulfonamide (P-2019),
N-[3-(4-Cyano-1H-pyrrolo[2,3-b]pyridine-3-carbonyl)-2,4-difluoro-phenyl]-2-fluoro-benzenesulfonamide (P-2020),
N-[2,4-Difluoro-3-(4-methoxy-1H-pyrrolo[2,3-b]pyridine-3-carbonyl)-phenyl]-2-fluoro-benzenesulfonamide (P-2021),
N-[2,4-Difluoro-3-(4-methoxy-1H-pyrrolo[2,3-b]pyridine-3-carbonyl)-phenyl]-2,5-difluoro-benzenesulfonamide (P-2022),
N-[2,4-Difluoro-3-(4-methoxy-1H-pyrrolo[2,3-b]pyridine-3-carbonyl)-phenyl]-3-fluoro-benzenesulfonamide (P-2023),
N-[2,4-Difluoro-3-(5-methyl-1H-pyrrolo[2,3-b]pyridine-3-carbonyl)-phenyl]-2,6-difluoro-benzenesulfonamide (P-2024),
N-[3-(5-Cyano-1H-pyrrolo[2,3-b]pyridine-3-carbonyl)-2,4-difluoro-phenyl]-2,6-difluoro-benzenesulfonamide (P-2029),
N-[2,4-Difluoro-3-(4-methoxy-1H-pyrrolo[2,3-b]pyridine-3-carbonyl)-phenyl]-2,6-difluoro-benzenesulfonamide (P-2031),
N-[3-(4-Chloro-1H-pyrrolo[2,3-b]pyridine-3-carbonyl)-2,4-difluoro-phenyl]-2,6-difluoro-benzenesulfonamide (P-2033),
N-[3-(4-Cyano-1H-pyrrolo[2,3-b]pyridine-3-carbonyl)-2,4-difluoro-phenyl]-2,5-difluoro-benzenesulfonamide (P-2036),
N-[3-(4-Cyano-1H-pyrrolo[2,3-b]pyridine-3-carbonyl)-2,4-difluoro-phenyl]-2,6-difluoro-benzenesulfonamide (P-2037),
N-[3-(4-Cyano-1H-pyrrolo[2,3-b]pyridine-3-carbonyl)-2,4-difluoro-phenyl]-3-fluoro-benzenesulfonamide (P-2039),
N-{2,4-Difluoro-3-[5-(2-methoxy-pyrimidin-5-yl)-1H-pyrrolo[2,3-b]pyridine-3-carbonyl]-phenyl}-2-fluoro-benzenesulfonamide (P-2041),
N-{2,4-Difluoro-3-[5-(2-methoxy-pyrimidin-5-yl)-1H-pyrrolo[2,3-b]pyridine-3-carbonyl]-phenyl}-2,5-difluoro-benzenesulfonamide (P-2042),
N-{2,4-Difluoro-3-[5-(2-methoxy-pyrimidin-5-yl)-1H-pyrrolo[2,3-b]pyridine-3-carbonyl]-phenyl}-2,6-difluoro-benzenesulfonamide (P-2043),
N-{2,4-Difluoro-3-[5-(2-methoxy-pyrimidin-5-yl)-1H-pyrrolo[2,3-b]pyridine-3-carbonyl]-phenyl}-3-fluoro-benzenesulfonamide (P-2045),
N-[3-(5-Cyano-1H-pyrrolo[2,3-b]pyridine-3-carbonyl)-2,4-difluoro-phenyl]-benzenesulfonamide (P-2046),
N-[3-(5-Cyano-1H-pyrrolo[2,3-b]pyridine-3-carbonyl)-2-fluoro-phenyl]-2-fluoro-benzenesulfonamide (P-2051),
N-[3-(5-Cyano-1H-pyrrolo[2,3-b]pyridine-3-carbonyl)-2-fluoro-phenyl]-2,5-difluoro-benzenesulfonamide (P-2052),
N-[3-(5-Cyano-1H-pyrrolo[2,3-b]pyridine-3-carbonyl)-2-fluoro-phenyl]-3-fluoro-benzenesulfonamide (P-2053),
N-[3-(5-Cyano-1H-pyrrolo[2,3-b]pyridine-3-carbonyl)-2-fluoro-phenyl]-2,6-difluoro-benzenesulfonamide (P-2054),
N-[3-(5-Cyano-1H-pyrrolo[2,3-b]pyridine-3-carbonyl)-2-fluoro-phenyl]-benzenesulfonamide (P-2056),
Pyridine-3-sulfonic acid [2,4-difluoro-3-(5-methyl-1H-pyrrolo[2,3-b]pyridine-3-carbonyl)-phenyl]-amide (P-2069),
Pyridine-3-sulfonic acid [3-(5-chloro-1H-pyrrolo[2,3-b]pyridine-3-carbonyl)-2,4-difluoro-phenyl]-amide (P-2071),
Pyridine-3-sulfonic acid [3-(5-cyano-1H-pyrrolo[2,3-b]pyridine-3-carbonyl)-2,4-difluoro-phenyl]-amide (P-2072),
Pyridine-3-sulfonic acid [2,4-difluoro-3-(4-methoxy-1H-pyrrolo[2,3-b]pyridine-3-carbonyl)-phenyl]-amide (P-2073),
Pyridine-3-sulfonic acid [3-(4-chloro-1H-pyrrolo[2,3-b]pyridine-3-carbonyl)-2,4-difluoro-phenyl]-amide (P-2074),
Pyridine-3-sulfonic acid [3-(4-cyano-1H-pyrrolo[2,3-b]pyridine-3-carbonyl)-2,4-difluoro-phenyl]-amide (P-2077), and
Pyridine-3-sulfonic acid [3-(5-cyano-1H-pyrrolo[2,3-b]pyridine-3-carbonyl)-2-fluoro-phenyl]-amide (P-2086).

The following table indicates the 1H-pyrrolo[2,3-b]pyridine (column 2) and sulfonyl chloride (column 3) used to afford the desired compound (column 4). The compound number is provided in column 1, and the observed mass is in column 5.

| | 1H-pyrrolo[2,3-b]pyridine | Sulfonyl chloride |
|---|---|---|
| P-2002 | 5-chloro-3-(2,6-difluoro-3-amino-benzoyl)-1H-pyrrolo[2,3-b]pyridine | 2,5-difluorobenzenesulfonyl chloride |
| P-2003 | 5-chloro-3-(2,6-difluoro-3-amino-benzoyl)-1H-pyrrolo[2,3-b]pyridine | 2,6-difluorobenzenesulfonyl chloride |
| P-2009 | 5-methoxy-3-(2,6-difluoro-3-amino-benzoyl)-1H-pyrrolo[2,3-b]pyridine | 2-fluorobenzenesulfonyl chloride |
| P-2010 | 5-methoxy-3-(2,6-difluoro-3-amino-benzoyl)-1H-pyrrolo[2,3-b]pyridine | 2,5-difluorobenzenesulfonyl chloride |
| P-2011 | 5-cyano-3-(2,6-difluoro-3-amino-benzoyl)-1H-pyrrolo[2,3-b]pyridine | 2-fluorobenzenesulfonyl chloride |
| P-2014 | 5-methyl-3-(2,6-difluoro-3-amino-benzoyl)-1H-pyrrolo[2,3-b]pyridine | 2-fluorobenzenesulfonyl chloride |

| | | |
|---|---|---|
| P-2015 | 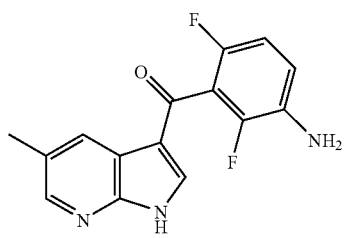 | 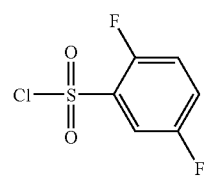 |
| P-2017 | 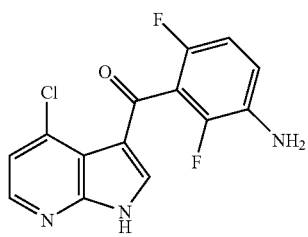 | 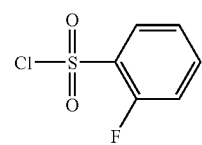 |
| P-2018 | 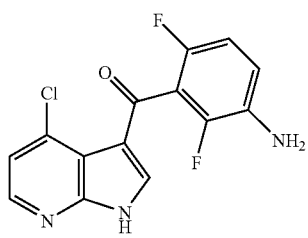 | 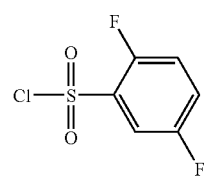 |
| P-2019 | 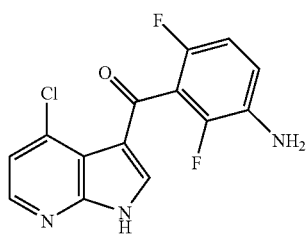 | 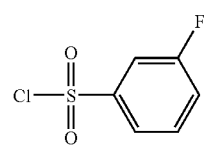 |
| P-2020 | 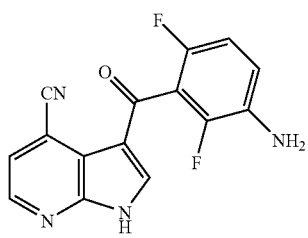 | 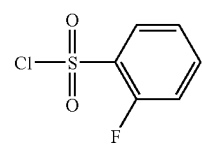 |
| P-2021 | 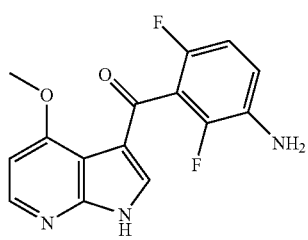 | 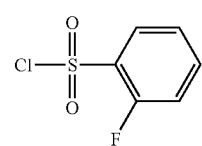 |

P-2022 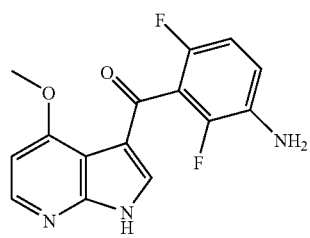 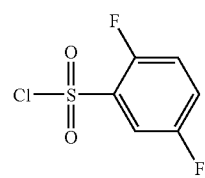
P-2023 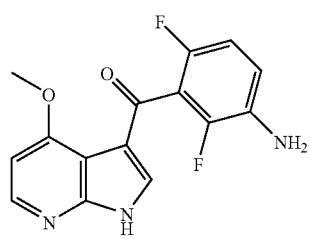 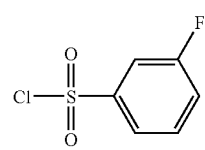
P-2024 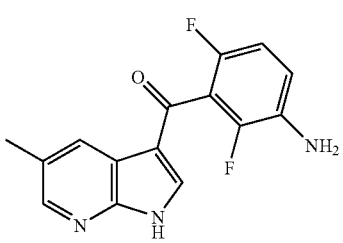 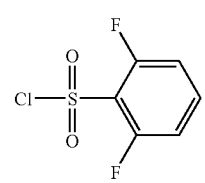
P-2029 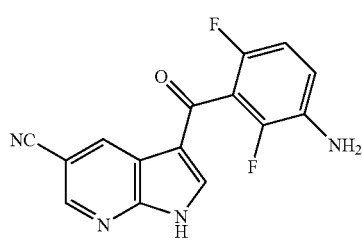 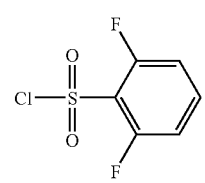
P-2031 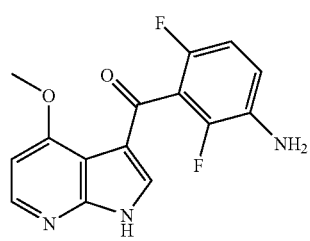 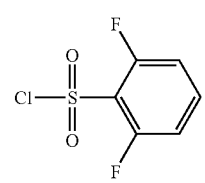
P-2033 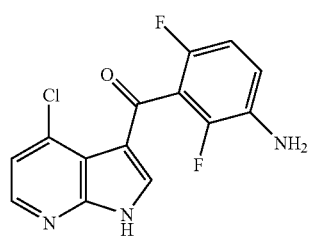 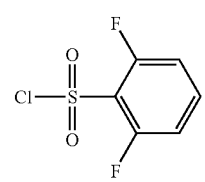

P-2036 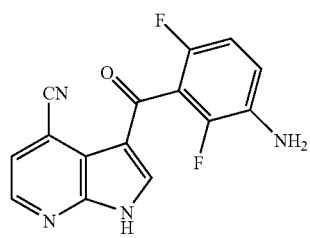 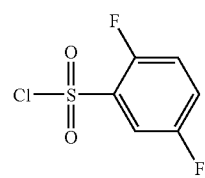
P-2037 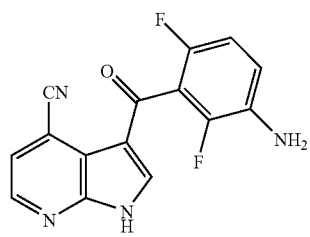 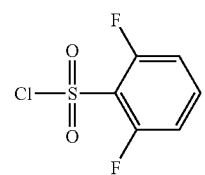
P-2039 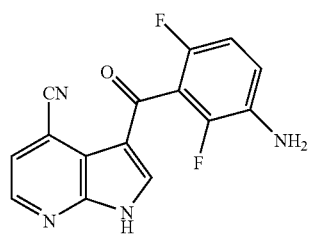 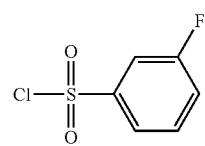
P-2041 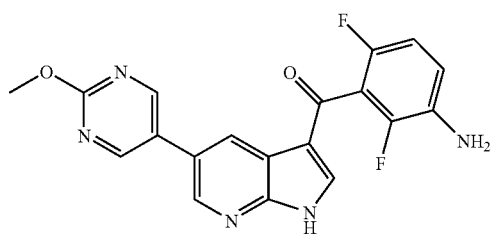 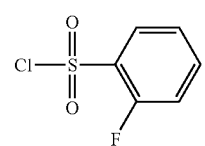
P-2042 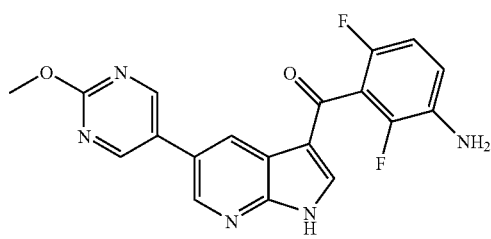 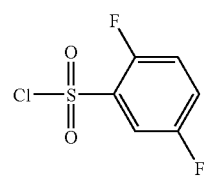
P-2043 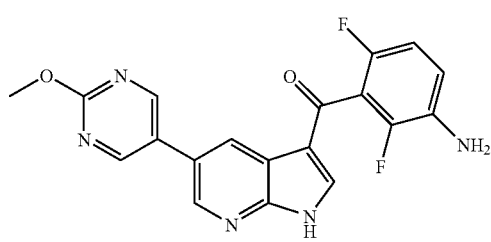 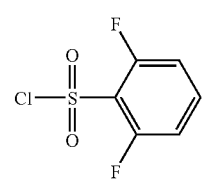

| | | |
|---|---|---|
| P-2045 | 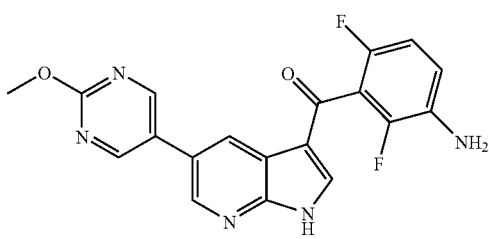 | 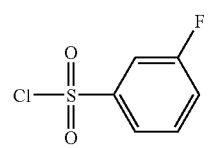 |
| P-2046 | 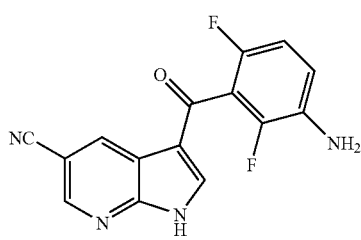 | 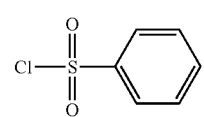 |
| P-2051 | 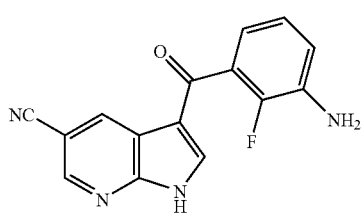 | 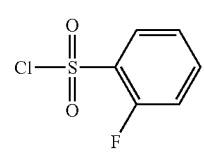 |
| P-2052 | 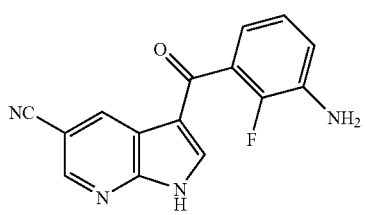 | 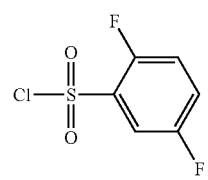 |
| P-2053 | 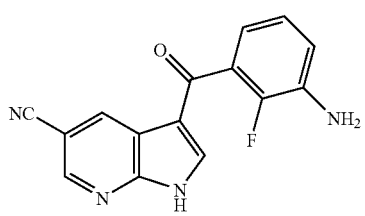 | 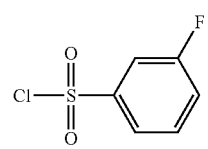 |
| P-2054 | 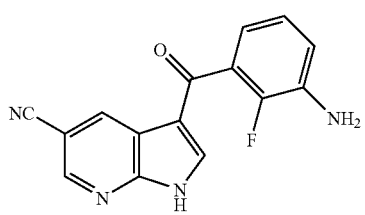 | 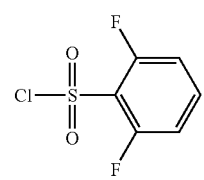 |
| P-2056 | 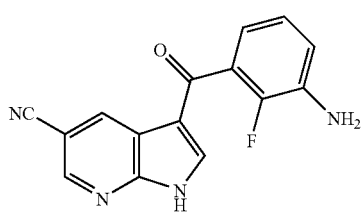 | 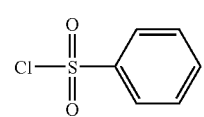 |

| | | |
|---|---|---|
| P-2069 | 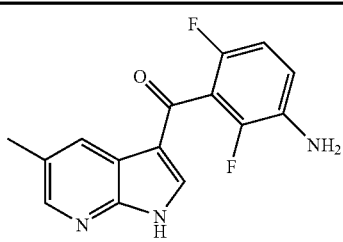 | 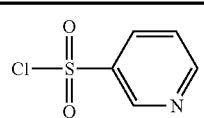 |
| P-2071 | 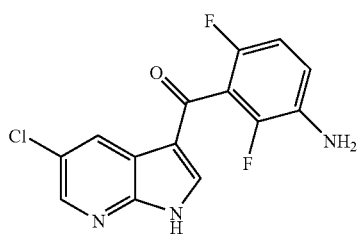 | 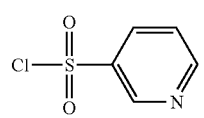 |
| P-2072 | 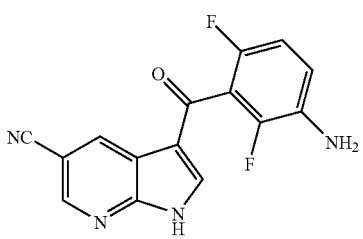 | 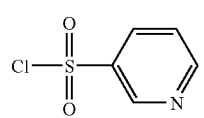 |
| P-2073 | 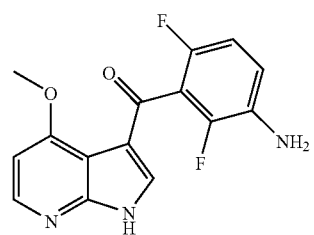 | 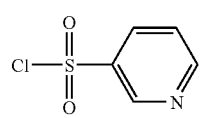 |
| P-2074 | 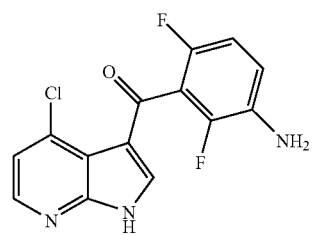 | 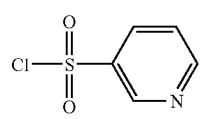 |
| P-2077 | 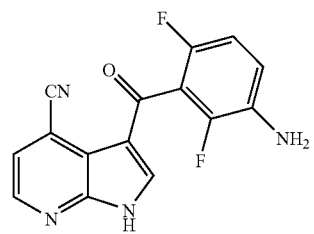 | 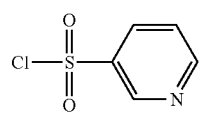 |
| P-2086 | 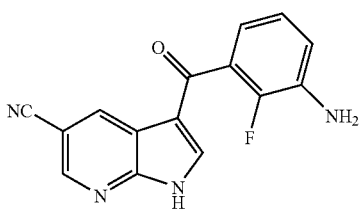 | 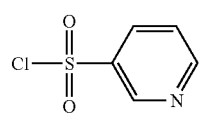 |

-continued
| Compound | MS (ESI) [M + H+]+ observed |
|---|---|
| P-2002 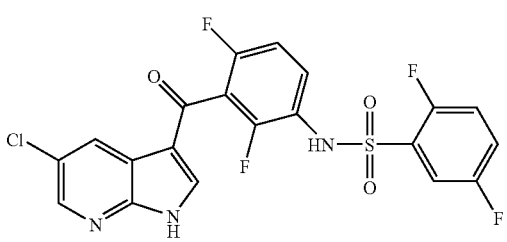 | 483.9 |
| P-2003 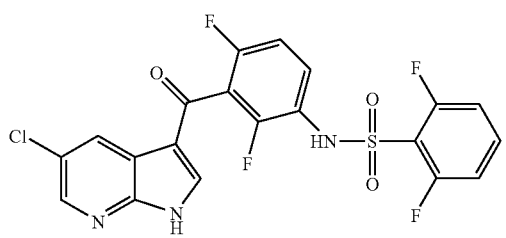 | 483.9 |
| P-2009 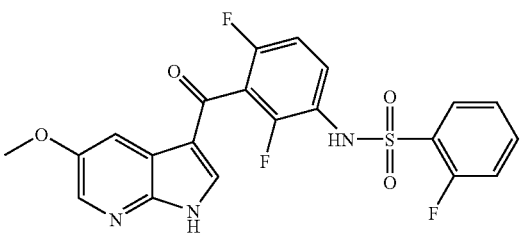 | 461.9 |
| P-2010 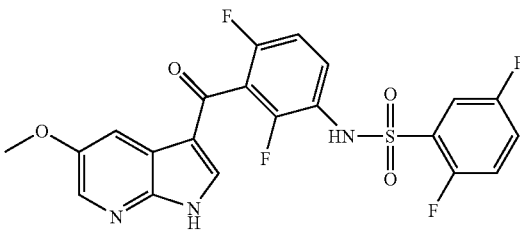 | 479.9 |
| P-2011 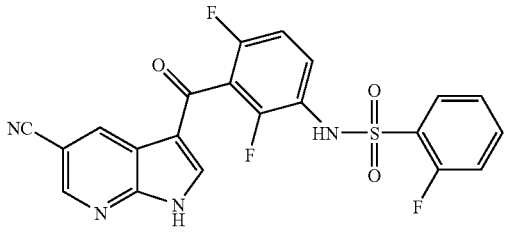 | 457.1 |
| P-2014 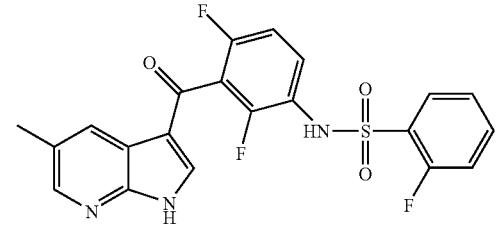 | 445.9 |

| | | |
|---|---|---|
| P-2015 | 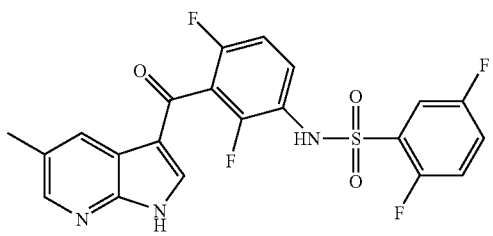 | 463.9 |
| P-2017 | 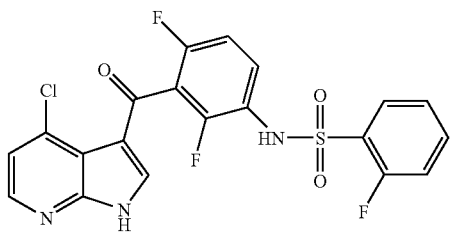 | 465.9 |
| P-2018 | 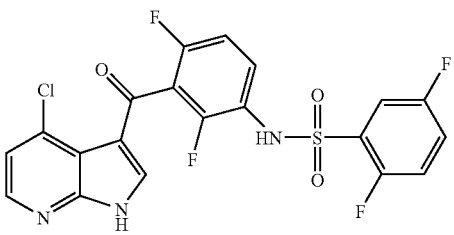 | 483.9 |
| P-2019 | 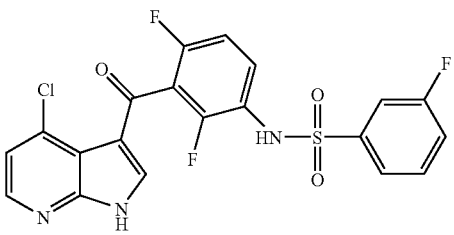 | 465.9 |
| P-2020 | 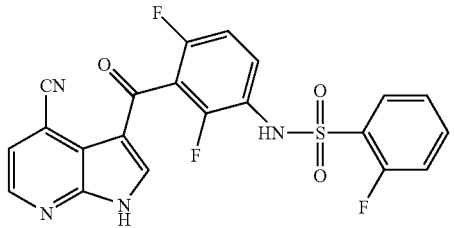 | 457.1 |
| P-2021 | 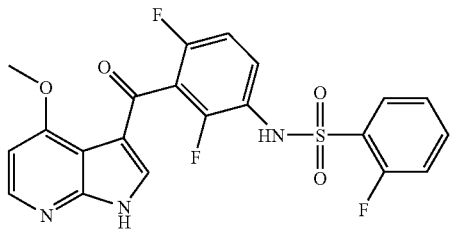 | 461.9 |

-continued
| | | |
|---|---|---|
| P-2022 | 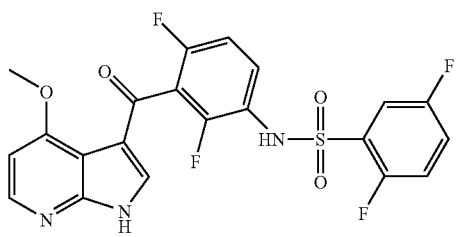 | 479.9 |
| P-2023 | 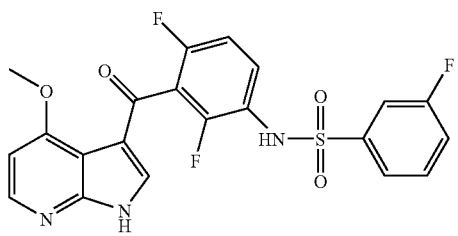 | 461.9 |
| P-2024 | 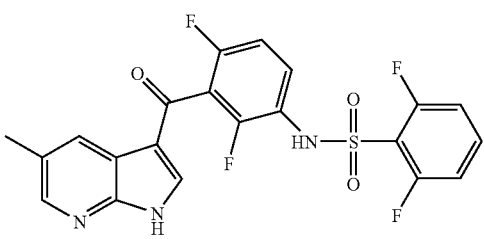 | 463.9 |
| P-2029 | 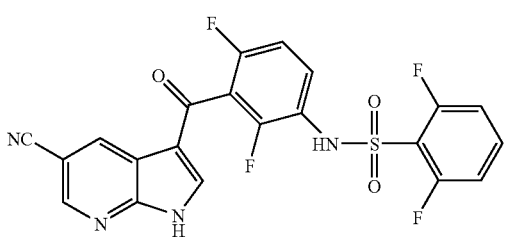 | 474.7 |
| P-2031 | 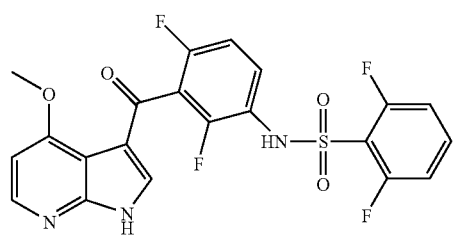 | 479.9 |
| P-2033 | 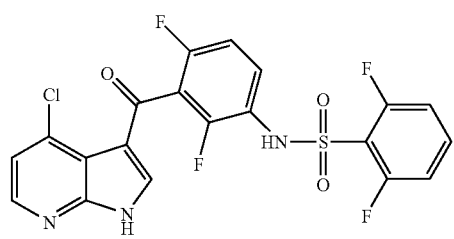 | 483.9 |

| | | |
|---|---|---|
| P-2036 | 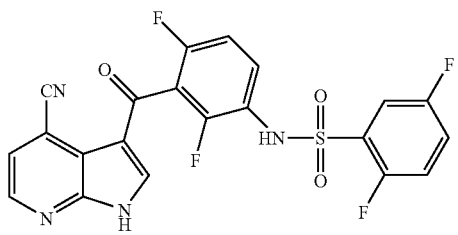 | 475.1 |
| P-2037 | 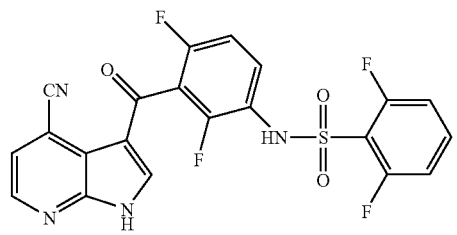 | 474.7 |
| P-2039 | 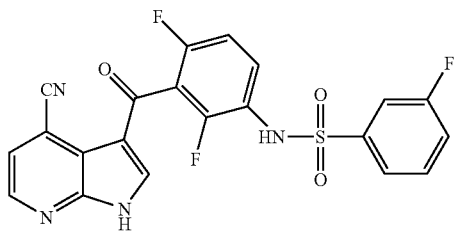 | 457.1 |
| P-2041 | 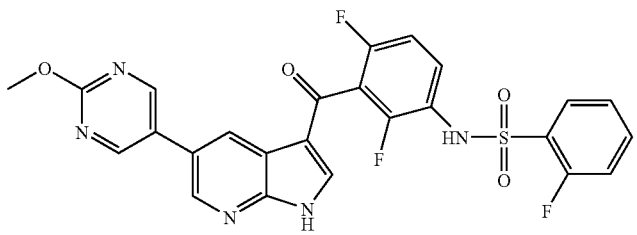 | 539.9 |
| P-2042 | 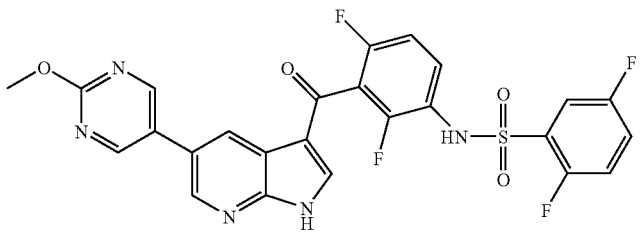 | 558.0 |
| P-2043 | 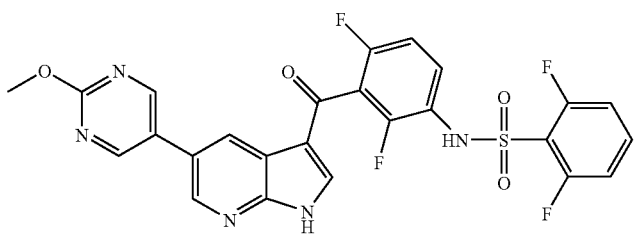 | 558.0 |

| | | |
|---|---|---|
| P-2045 | 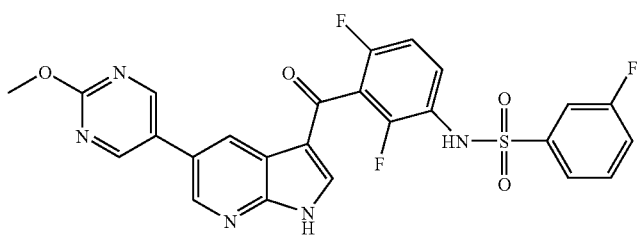 | 539.9 |
| P-2046 | 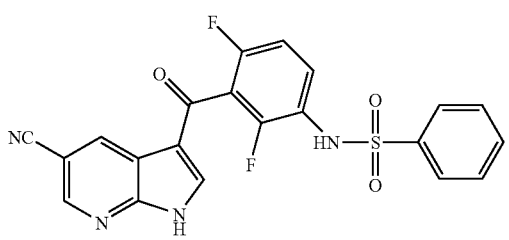 | 437.5 |
| P-2051 | 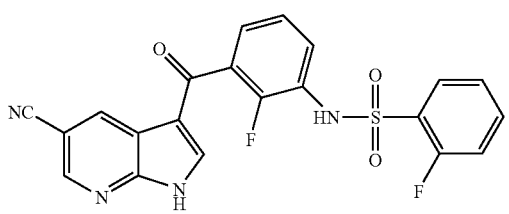 | 439.1 |
| P-2052 | 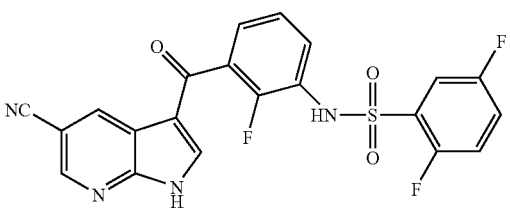 | 457.1 |
| P-2053 | 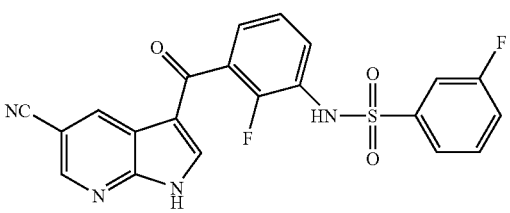 | 438.7 |
| P-2054 | 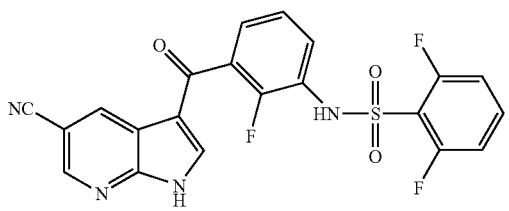 | 457.7 |
| P-2056 | 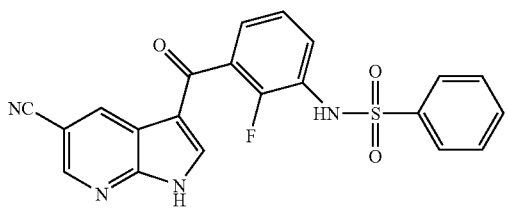 | 420.9 |

| | | |
|---|---|---|
| P-2069 | 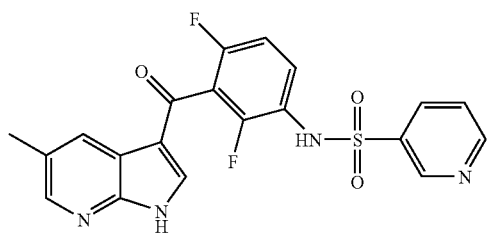 | 429.1 |
| P-2071 | 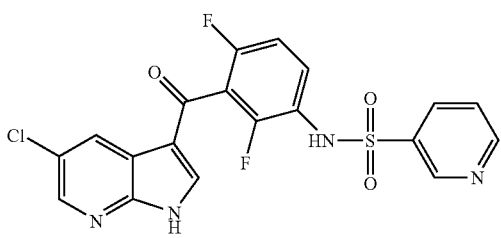 | 448.8 |
| P-2072 | 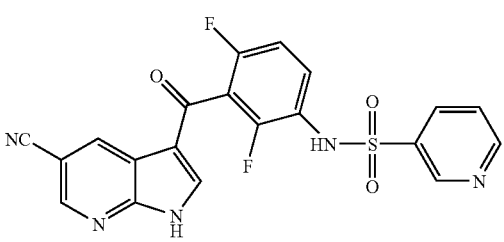 | 439.9 |
| P-2073 | 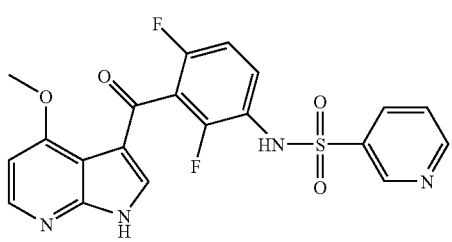 | 445.1 |
| P-2074 | 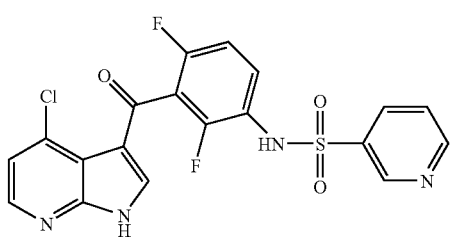 | 448.7 |
| P-2077 | 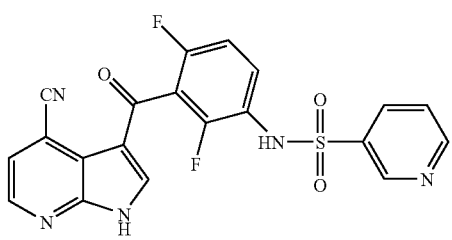 | 439.9 |

| P-2086 | 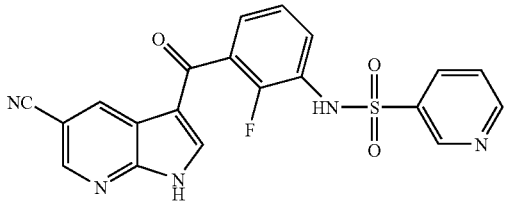 | 421.9 |

Example 12

Synthesis of propane-1-sulfonic acid {3-[5-(6-chloro-pyridin-3-yl)-1H-pyrrolo[2,3-b]pyridine-3-carbonyl]-2,4-difluoro-phenyl}-amide P-2154

Propane-1-sulfonic acid {3-[5-(6-chloro-pyridin-3-yl)-1H-pyrrolo[2,3-b]pyridine-3-carbonyl]-2,4-difluoro-phenyl}-amide P-2154 was synthesized in one step from propane-1-sulfonic acid [3-(5-bromo-1H-pyrrolo[2,3-b]pyridine-3-carbonyl)-2,4-difluoro-phenyl]-amide 56 as shown in Scheme 12.

Scheme 12

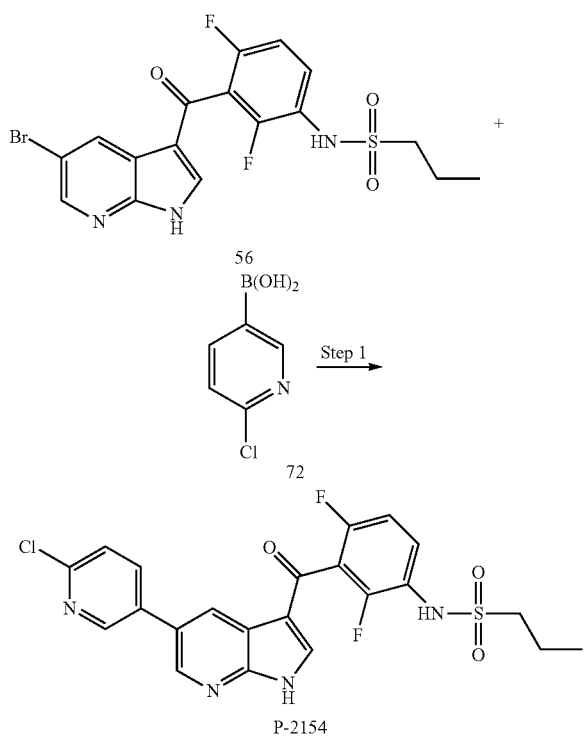

Step 1—Preparation of propane-1-sulfonic acid {3-[5-(6-chloro-pyridin-3-yl)-1H-pyrrolo[2,3-b]pyridine-3-carbonyl]-2,4-difluoro-phenyl}-amide (P-2154)

Propane-1-sulfonic acid [3-(5-bromo-1H-pyrrolo[2,3-b]pyridine-3-carbonyl)-2,4-difluoro-phenyl]-amide (56, 10 mg, 0.022 mmol) was weighed into a 5 mL microwave vial and combined with 6-chloro-pyridine-3-boronic acid (72, 4.4 mg, 0.028 mmol), followed by the addition of 600 µL of acetonitrile and 500 µL of 1M potassium carbonate and a spatula tip (~1 mg) of [1,1''-bis(diphenylphosphino)-ferrocene]dichloropalladium(II). The reaction mixture was irradiated in a microwave at 160° C. for 5 minutes. The solution was neutralized with 100 µL of acetic acid and all material was transferred to a 4 mL vial and the solvents were removed under vacuum. The crude material was dissolved in 400 µL of dimtheylsulfoxide and purified by reverse phase HPLC, eluting with 0.1% trifluoroacetic acid in water and 0.1% trifluoroacetic acid in acetonitrile, 20-100% acetonitrile over 16 minutes at 6 mL per minute. Appropriate fractions were combined and the solvent removed under reduced pressure to provide the desired compound. MS (ESI) [M+H$^+$]$^+$=491.1.

Additional compounds were prepared similarly to the protocol of Scheme 12, where optimal reaction conditions may have varied in terms of time and temperature of the reaction, or alternatively, tetrakis(triphenylphosphine)palladium(0) was used as a catalyst, and in chromatography conditions for purification of the desired compounds. The reactions were performed optionally substituting 6-chloro-pyridine-3-boronic acid 72 with an appropriate boronic acid and/or propane-1-sulfonic acid [3-(5-bromo-1H-pyrrolo[2,3-b]pyridine-3-carbonyl)-2,4-difluoro-phenyl]-amide 56 with an appropriate 5-bromo-1H-pyrrolo[2,3-b]pyridine derivative. The following compounds were prepared by this procedure:

Propane-1-sulfonic acid {2,4-difluoro-3-[5-(6-fluoro-pyridin-3-yl)-1H-pyrrolo[2,3-b]pyridine-3-carbonyl]-phenyl}-amide (P-2155), N-(4-{3-[2,6-Difluoro-3-(propane-1-sulfonylamino)-benzoyl]-1H-pyrrolo[2,3-b]pyridin-5-yl}-phenyl)-acetamide (P-2161), Propane-1-sulfonic acid [2,4-difluoro-3-(5-pyrimidin-5-yl-1H-pyrrolo[2,3-b]pyridine-3-carbonyl)-phenyl]-amide (P-2162), Propane-1-sulfonic acid {2,4-difluoro-3-[5-(2-fluoro-pyridin-3-yl)-1H-pyrrolo[2,3-b]pyridine-3-carbonyl]-phenyl}-amide (P-2164), Propane-1-sulfonic acid {2,4-difluoro-3-[5-(4-methanesulfonylamino-phenyl)-1H-pyrrolo[2,3-b]pyridine-3-carbonyl]-phenyl}-amide (P-2165), Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide (P-2166), 4-{3-[2,6-Difluoro-3-(propane-1-sulfonylamino)-benzoyl]-1H-pyrrolo[2,3-b]pyridin-5-yl}-N-methyl-benzenesulfonamide (P-2167), N-Cyclopropyl-4-{3-[2,6-difluoro-3-(propane-1-sulfonylamino)-benzoyl]-1H-pyrrolo[2,3-b]pyridin-5-yl}-benzenesulfonamide (P-2168), Propane-1-sulfonic acid {2,4-difluoro-3-[5-(3-methanesulfonylamino-phenyl)-1H-pyrrolo[2,3-b]pyridine-3-carbonyl]-phenyl}-amide (P-2169), Propane-1-sulfonic acid {2,4-difluoro-3-[5-(2-fluoro-6-methyl-pyridin-3-yl)-1H-pyrrolo[2,3-b]pyridine-3-carbonyl]-phenyl}-amide (P-2172), Propane-1-sulfonic acid {2,4-difluoro-3-[5-(1H-pyrazol-4-yl)-1H-pyrrolo[2,3-b]pyridine-3-carbonyl]-phenyl}-amide (P-2174), Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide (P-2177),
Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide (P-2178),
Propane-1-sulfonic acid {2,4-difluoro-3-[5-(4-methanesulfonyl-phenyl)-1H-pyrrolo[2,3-b]pyridine-3-carbonyl]-phenyl}-amide (P-2183),
Propane-1-sulfonic acid {3-[5-(2,6-dimethoxy-pyridin-3-yl)-1H-pyrrolo[2,3-b]pyridine-3-carbonyl]-2,4-difluoro-phenyl}-amide (P-2184),
4-{3-[2,6-Difluoro-3-(propane-1-sulfonylamino)-benzoyl]-1H-pyrrolo[2,3-b]pyridin-5-yl}-N,N-dimethyl-benzenesulfonamide (P-2185),
Propane-1-sulfonic acid {2,4-difluoro-3-[5-(6-methylsulfanyl-pyridin-3-yl)-1H-pyrrolo[2,3-b]pyridine-3-carbonyl]-phenyl}-amide (P-2187),
Propane-1-sulfonic acid {2,4-difluoro-3-[5-(5-methanesulfonyl-pyridin-3-yl)-1H-pyrrolo[2,3-b]pyridine-3-carbonyl]-phenyl}-amide (P-2188),
Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide (P-2189),
Propane-1-sulfonic acid {3-[5-(1-benzyl-1H-pyrazol-4-yl)-1H-pyrrolo[2,3-b]pyridine-3-carbonyl]-2,4-difluoro-phenyl}-amide (P-2190),
Propane-1-sulfonic acid {2,4-difluoro-3-[5-(2-fluoro-pyridin-4-yl)-1H-pyrrolo[2,3-b]pyridine-3-carbonyl]-phenyl}-amide (P-2192),
N-(5-{3-[2,6-Difluoro-3-(propane-1-sulfonylamino)-benzoyl]-1H-pyrrolo[2,3-b]pyridin-5-yl}-pyridin-2-yl)-acetamide (P-2193),
4-{3-[2,6-Difluoro-3-(propane-1-sulfonylamino)-benzoyl]-1H-pyrrolo[2,3-b]pyridin-5-yl}-benzenesulfonamide (P-2194),
Propane-1-sulfonic acid {3-[5-(2-dimethylamino-pyrimidin-5-yl)-1H-pyrrolo[2,3-b]pyridine-3-carbonyl]-2,4-difluoro-phenyl}-amide (P-2196),
Propane-1-sulfonic acid {2,4-difluoro-3-[5-(2-morpholin-4-yl-pyrimidin-5-yl)-1H-pyrrolo[2,3-b]pyridine-3-carbonyl]-phenyl}-amide (P-2197),
Propane-1-sulfonic acid {3-[5-(2,4-dimethoxy-pyrimidin-5-yl)-1H-pyrrolo[2,3-b]pyridine-3-carbonyl]-2,4-difluoro-phenyl}-amide (P-2199),
Propane-1-sulfonic acid {2,4-difluoro-3-[5-(2-methyl-pyrimidin-5-yl)-1H-pyrrolo[2,3-b]pyridine-3-carbonyl]-phenyl}-amide (P-2211),
Propane-1-sulfonic acid {2,4-difluoro-3-[5-(6-methyl-pyridin-3-yl)-1H-pyrrolo[2,3-b]pyridine-3-carbonyl]-phenyl}-amide (P-2213),
Propane-1-sulfonic acid {3-[5-(6-amino-pyridin-3-yl)-1H-pyrrolo[2,3-b]pyridine-3-carbonyl]-2,4-difluoro-phenyl}-amide (P-2214),
Propane-1-sulfonic acid {3-[5-(4-ethanesulfonyl-phenyl)-1H-pyrrolo[2,3-b]pyridine-3-carbonyl]-2,4-difluoro-phenyl}-amide (P-2218),
Propane-1-sulfonic acid {2,4-difluoro-3-[5-(2-pyrrolidin-1-yl-pyrimidin-5-yl)-1H-pyrrolo[2,3-b]pyridine-3-carbonyl]-phenyl}-amide (P-2219),
5-{3-[2,6-Difluoro-3-(propane-1-sulfonylamino)-benzoyl]-1H-pyrrolo[2,3-b]pyridin-5-yl}-pyridine-2-carboxylic acid amide (P-2220),
Propane-1-sulfonic acid (2,4-difluoro-3-{5-[4-(propane-2-sulfonyl)-phenyl]-1H-pyrrolo[2,3-b]pyridine-3-carbonyl}-phenyl)-amide (P-2223),
Propane-1-sulfonic acid {2,4-difluoro-3-[5-(3-methanesulfonyl-phenyl)-1H-pyrrolo[2,3-b]pyridine-3-carbonyl]-phenyl}-amide (P-2228),
Propane-1-sulfonic acid {3-[5-(6-dimethylamino-pyridin-3-yl)-1H-pyrrolo[2,3-b]pyridine-3-carbonyl]-2,4-difluoro-phenyl}-amide (P-2229),
Propane-1-sulfonic acid {2,4-difluoro-3-[5-(6-pyrrolidin-1-yl-pyridin-3-yl)-1H-pyrrolo[2,3-b]pyridine-3-carbonyl]-phenyl}-amide (P-2231),
Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide (P-2232),
Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide (P-2233),
Propane-1-sulfonic acid {2,4-difluoro-3-[5-(6-hydroxy-pyridin-3-yl)-1H-pyrrolo[2,3-b]pyridine-3-carbonyl]-phenyl}-amide (P-2234),
Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide (P-2235),
Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide (P-2236),
2-Methyl-propane-1-sulfonic acid {2,4-difluoro-3-[5-(1-methyl-1H-pyrazol-4-yl)-1H-pyrrolo[2,3-b]pyridine-3-carbonyl]-phenyl}-amide (P-2299),
Propane-1-sulfonic acid {2-fluoro-3-[5-(2-methoxy-pyrimidin-5-yl)-1H-pyrrolo[2,3-b]pyridine-3-carbonyl]-phenyl}-amide (P-2407), and
Propane-1-sulfonic acid {3-[5-(2-dimethylamino-pyrimidin-5-yl)-1H-pyrrolo[2,3-b]pyridine-3-carbonyl]-2-fluoro-phenyl}-amide (P-2408).

The following table indicates the 1H-pyrrolo[2,3-b]pyridine (column 2) and boronic acid (column 3) used to afford the desired compound (column 4). The compound number is provided in column 1, and the observed mass is in column 5.

|  | 1H-pyrrolo[2,3-b]pyridine | Boronic acid |
|---|---|---|
| P-2155 | | |

| | | |
|---|---|---|
| P-2161 | 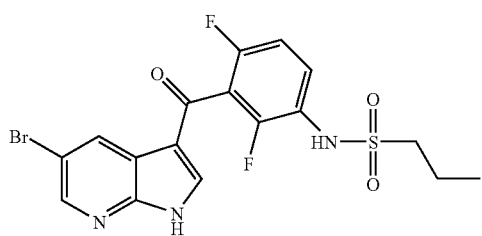 | 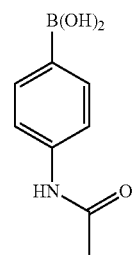 |
| P-2162 | 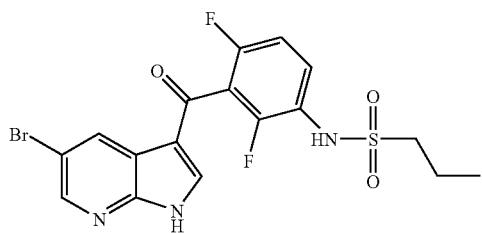 | 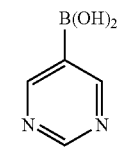 |
| P-2164 | 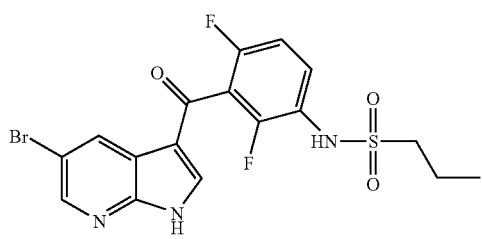 | 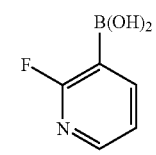 |
| P-2165 | 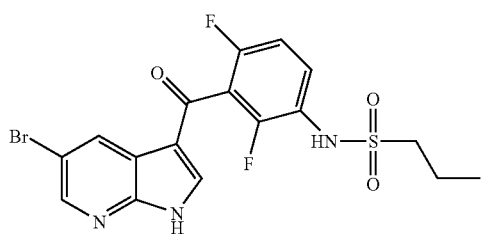 | 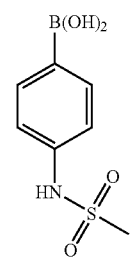 |
| P-2166 | 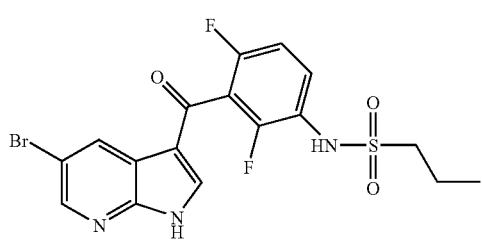 | 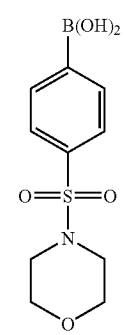 |
| P-2167 | 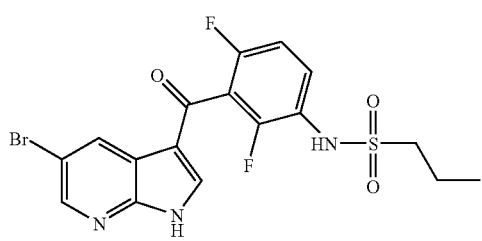 | 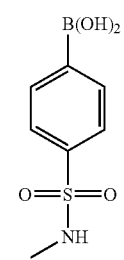 |

| | 117 | 118 |
|---|---|---|
| P-2168 | 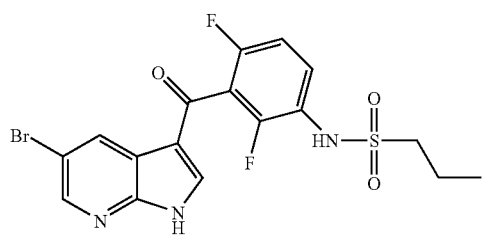 | 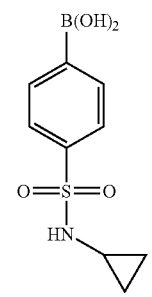 |
| P-2169 | 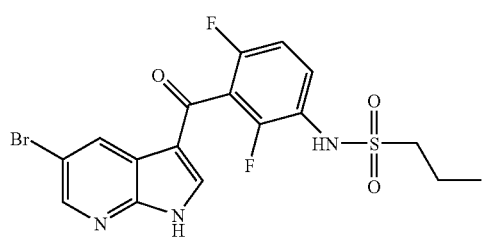 | 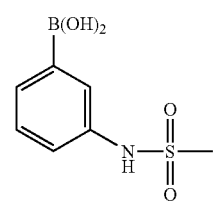 |
| P-2172 | 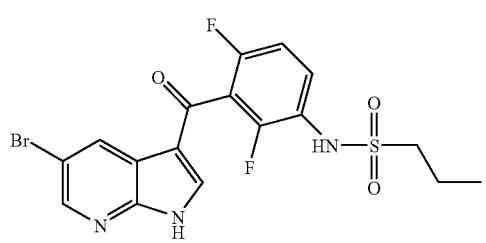 | 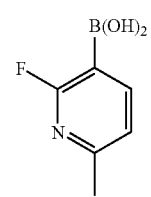 |
| P-2174 | 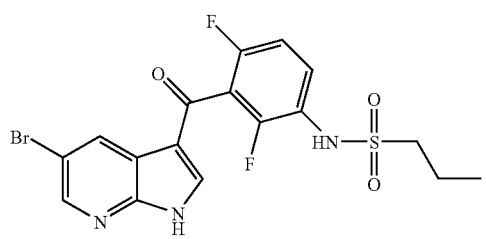 | 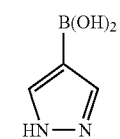 |
| P-2177 | 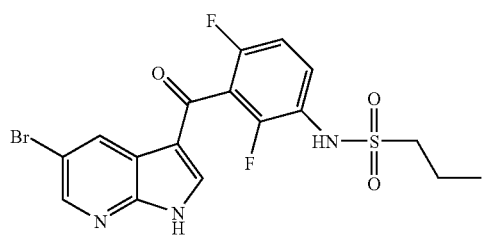 | 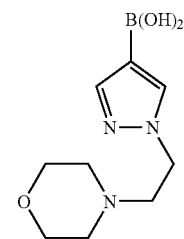 |
| P-2178 | 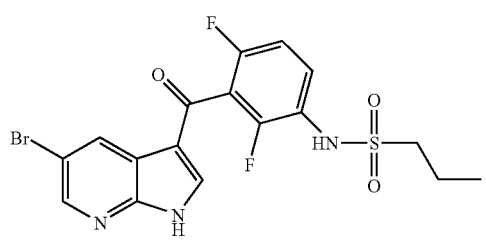 | 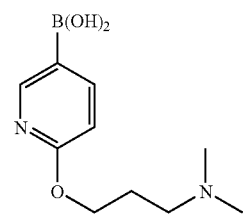 |

| | 119 | | 120 |
|---|---|---|---|
| P-2183 | 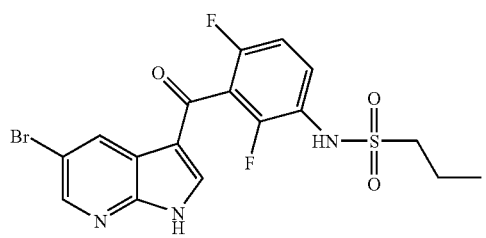 | | 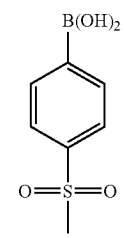 |
| P-2184 | 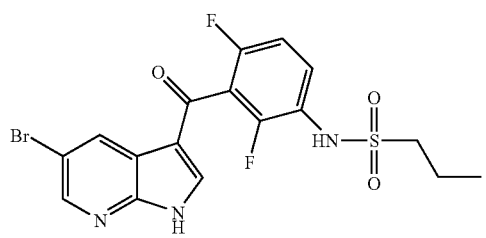 | | 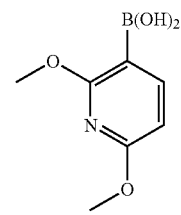 |
| P-2185 | 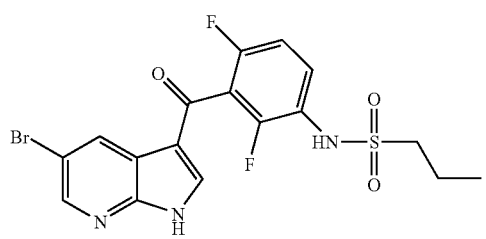 | | 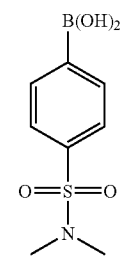 |
| P-2187 | 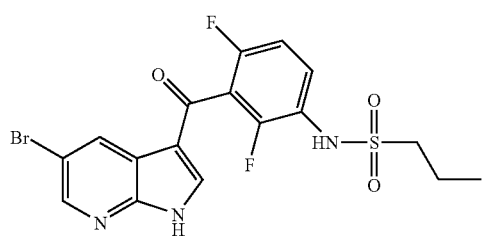 | | 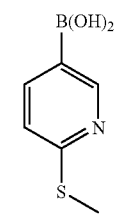 |
| P-2188 | 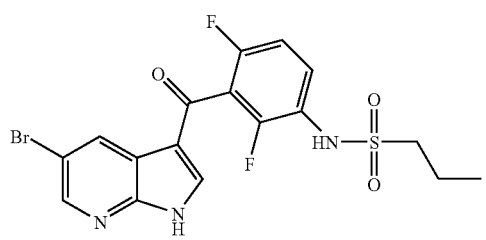 | | 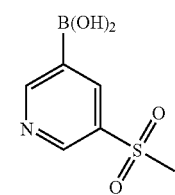 |
| P-2189 | 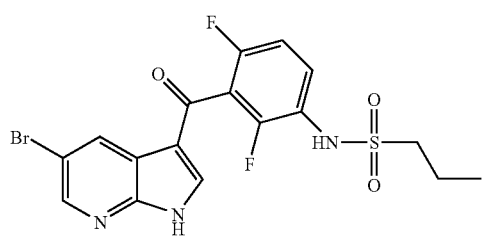 | | 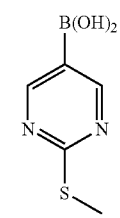 |

US 8,198,273 B2
| | 121 | 122 |
|---|---|---|
| | -continued | |
| P-2190 | 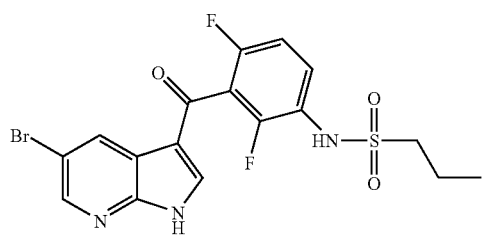 | 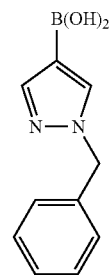 |
| P-2192 | 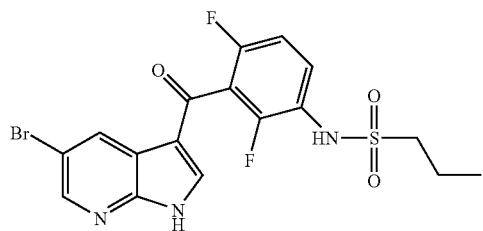 | 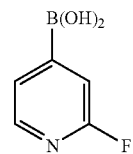 |
| P-2193 | 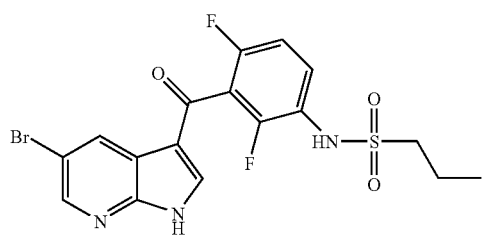 | 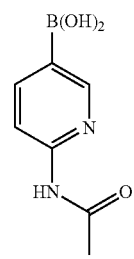 |
| P-2194 | 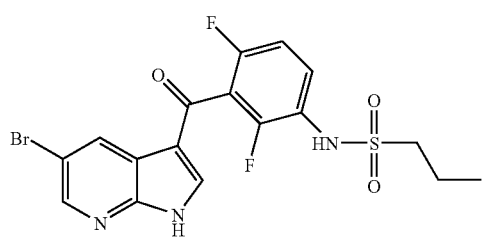 | 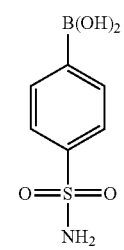 |
| P-2196 | 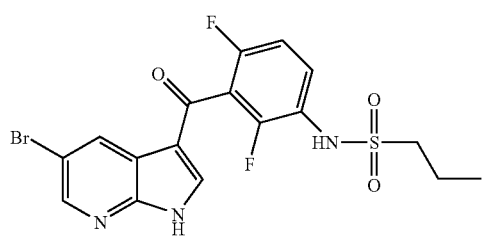 | 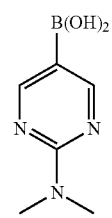 |
| P-2197 | 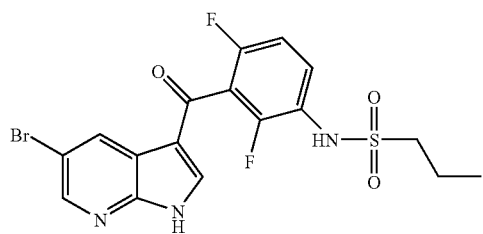 | 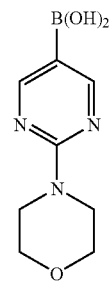 |

| | 123 | 124 |
|---|---|---|
| P-2199 | 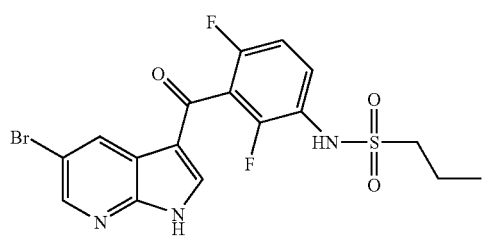 | 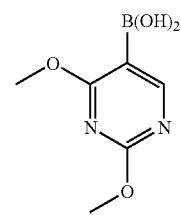 |
| P-2211 | 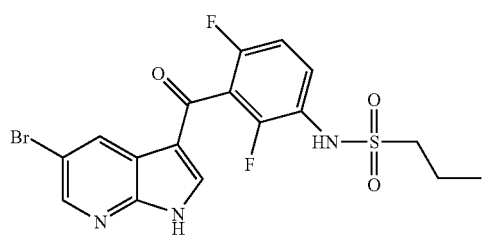 | 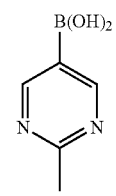 |
| P-2213 | 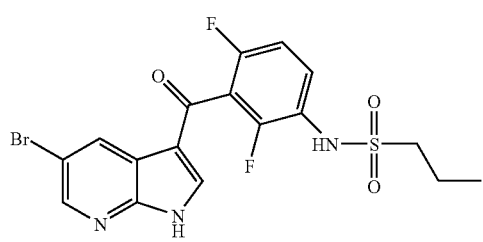 | 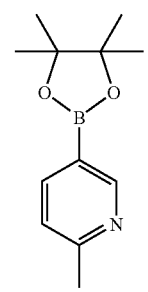 |
| P-2214 | 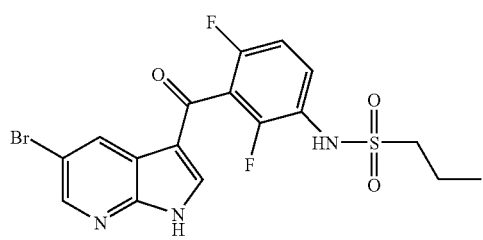 | 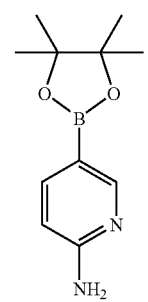 |
| P-2218 | 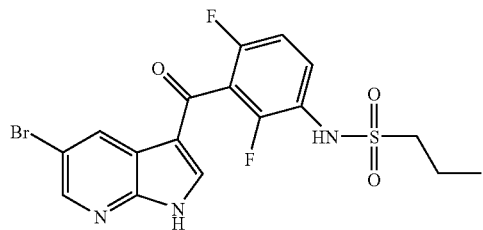 | 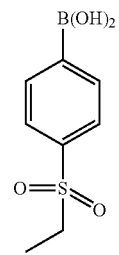 |
| P-2219 | 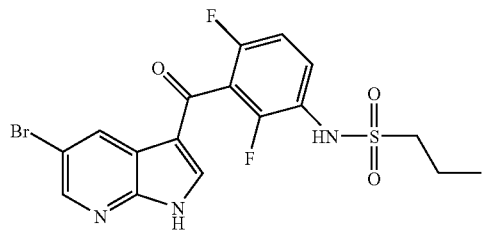 | 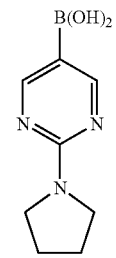 |

| | 125 | 126 |
|---|---|---|
| P-2220 | 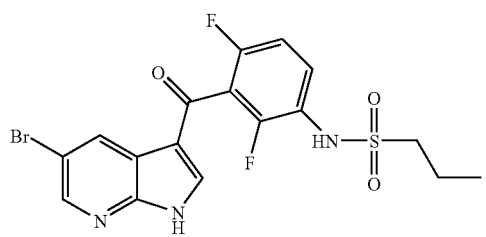 | 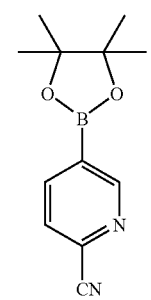 |
| P-2223 | 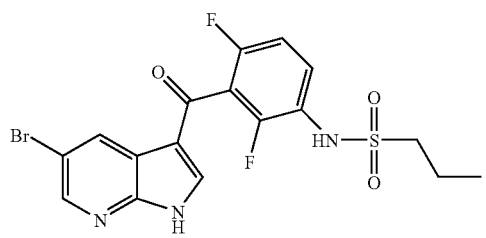 | 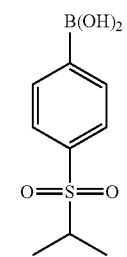 |
| P-2228 | 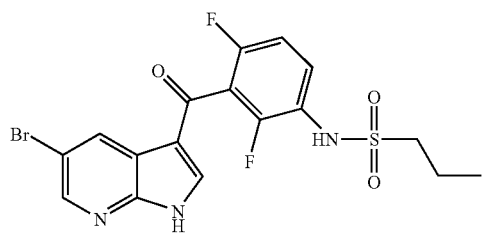 | 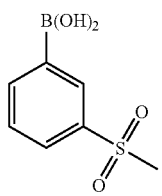 |
| P-2229 | 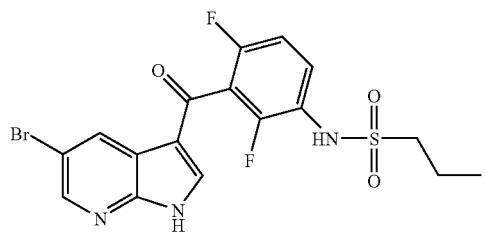 | 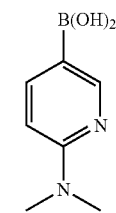 |
| P-2231 | 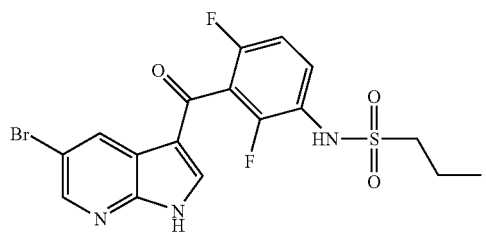 | 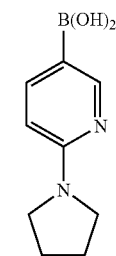 |

| | | | |
|---|---|---|---|
| P-2232 | 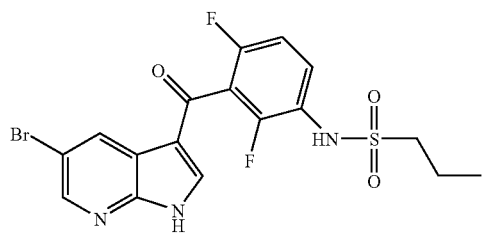 | | 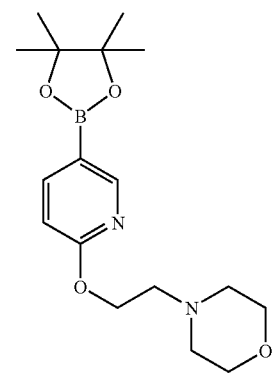 |
| P-2233 | 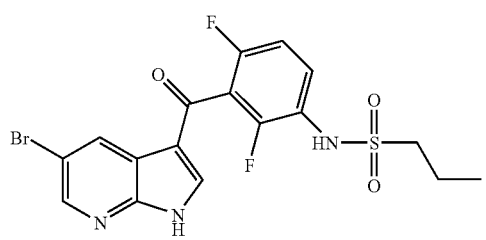 | | 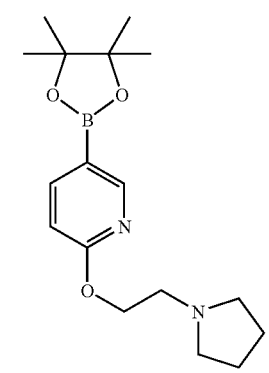 |
| P-2234 | 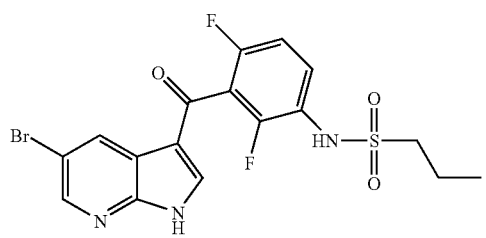 | | 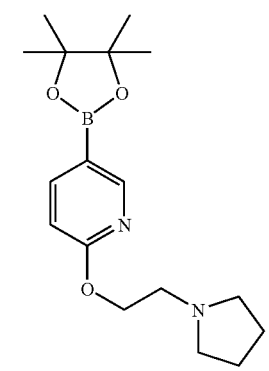 |
| P-2235 | 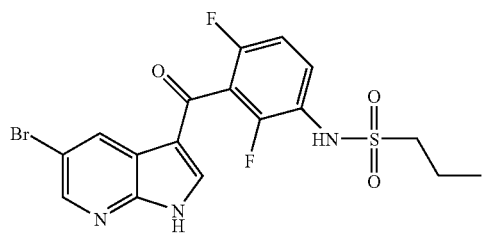 | | 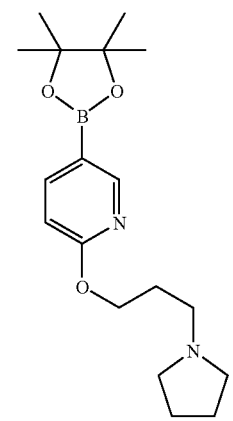 |

-continued
| | | |
|---|---|---|
| P-2236 | 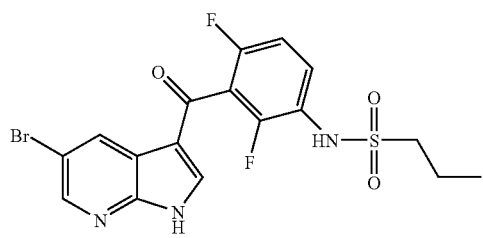 | 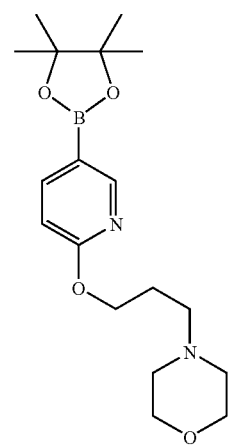 |
| P-2299 | 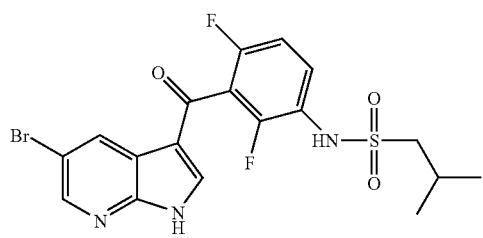 | 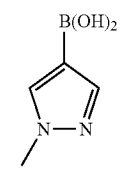 |
| P-2407 | 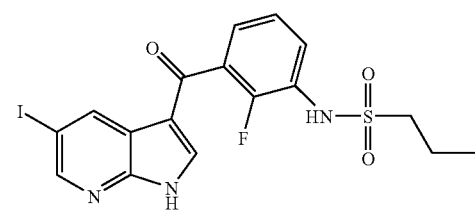 | 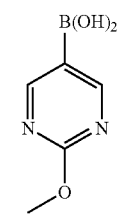 |
| P-2408 | 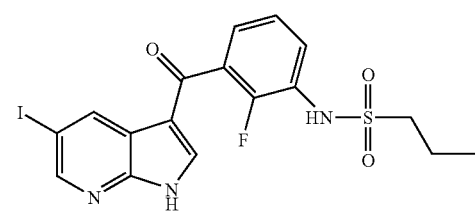 | 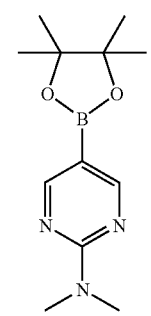 |
| Compound | | MS (ESI) [M + H$^+$]$^+$ observed |
|---|---|---|
| P-2155 | 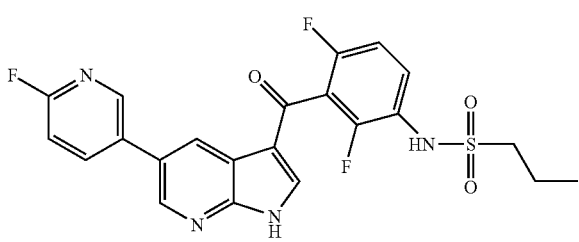 | 475.1 |

| | | |
|---|---|---|
| P-2161 | 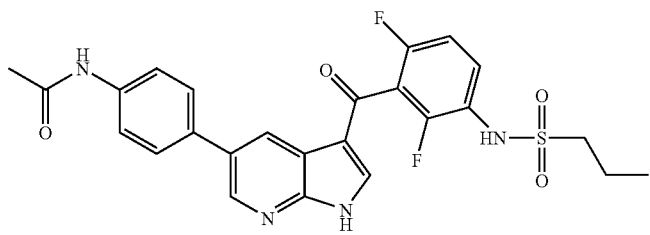 | 513.1 |
| P-2162 | 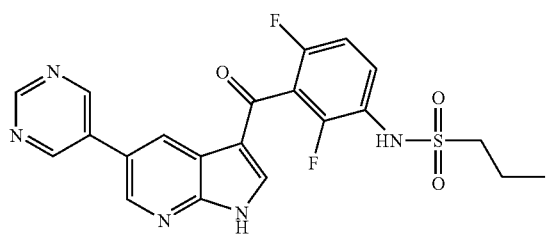 | 458.3 |
| P-2164 | 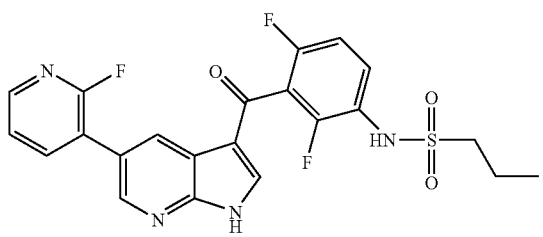 | 475.1 |
| P-2165 | 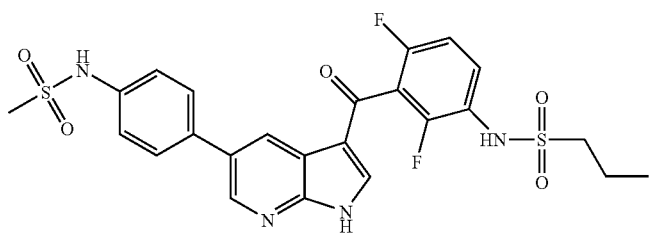 | 549.1 |
| P-2166 | 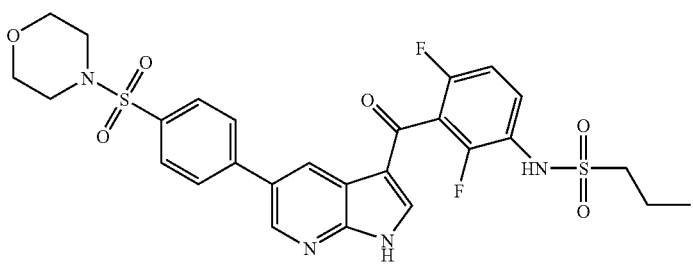 | 605.2 |
| P-2167 | 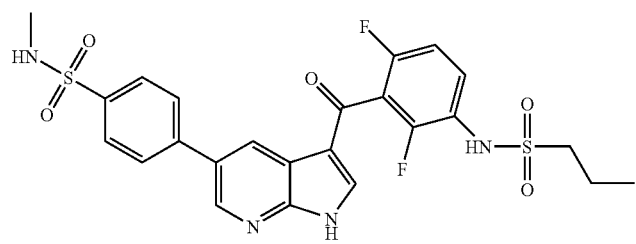 | 549.1 |

-continued
| | | |
|---|---|---|
| P-2168 | 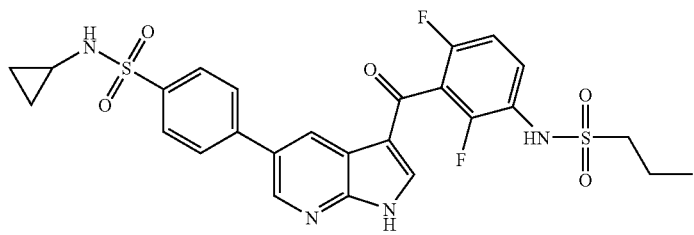 | 575.2 |
| P-2169 | 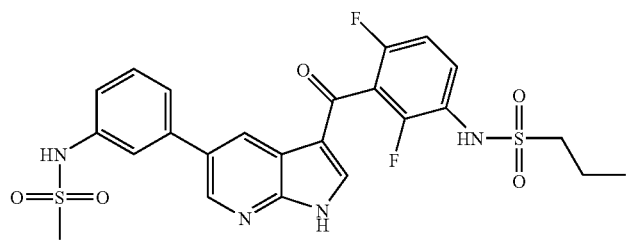 | 549.1 |
| P-2172 | 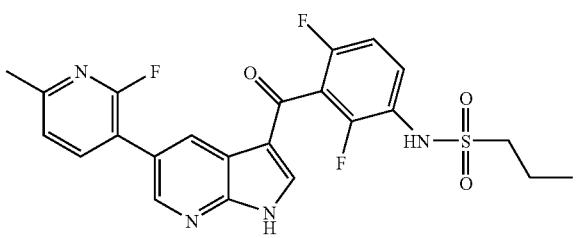 | |
| P-2174 | 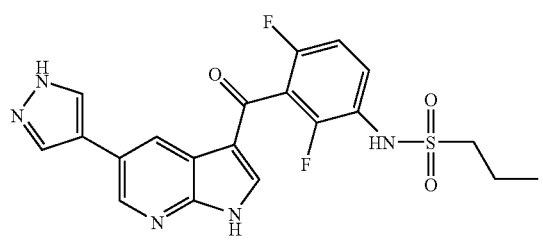 | 446.0 |
| P-2177 | 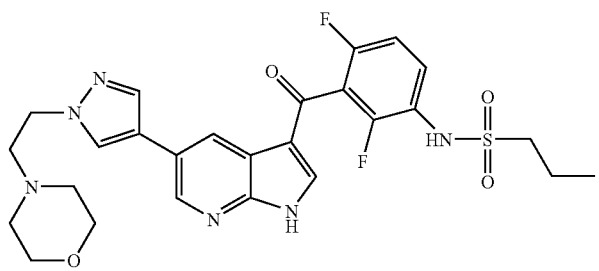 | 459.0 |
| P-2178 | 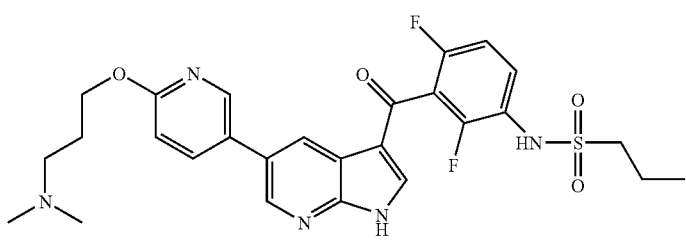 | 458.2 |

| | | |
|---|---|---|
| P-2183 | 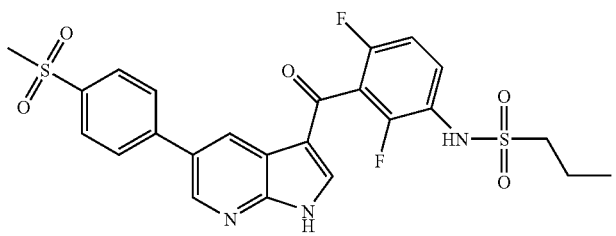 | 533.9 |
| P-2184 | 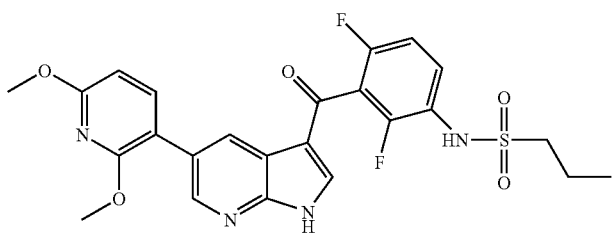 | 517.1 |
| P-2185 | 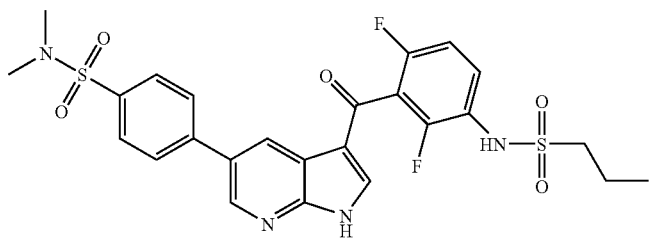 | 563.2 |
| P-2187 | 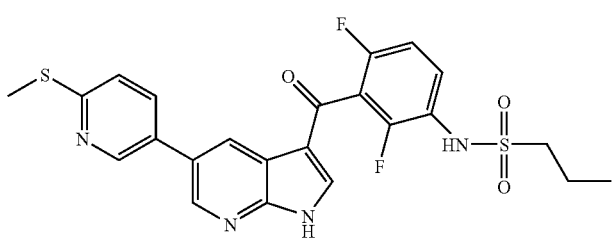 | 503.1 |
| P-2188 | 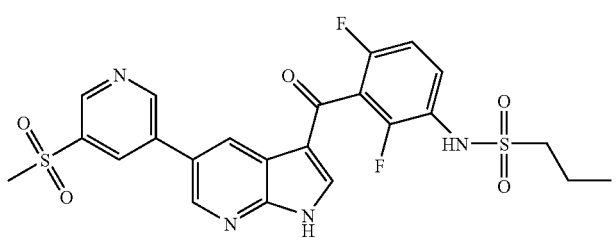 | 535.1 |
| P-2189 | 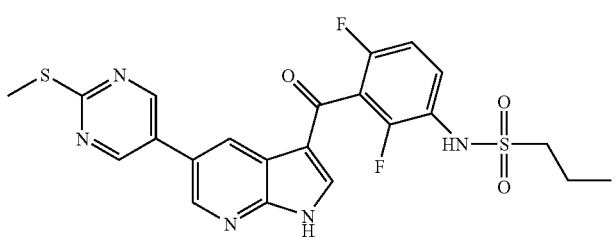 | 503.9 |

| | | |
|---|---|---|
| P-2190 | 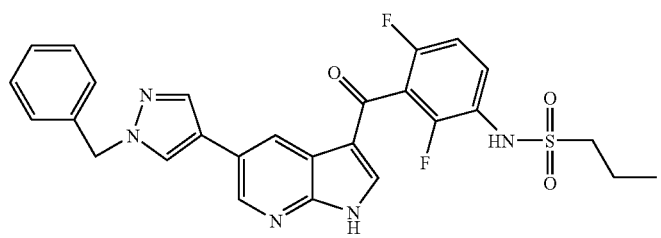 | 536.3 |
| P-2192 | 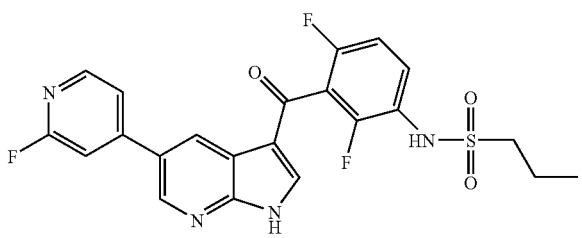 | 475.1 |
| P-2193 | 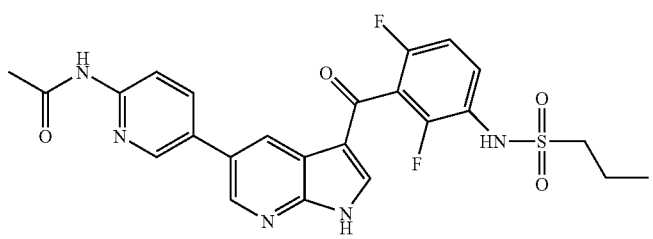 | 514.3 |
| P-2194 | 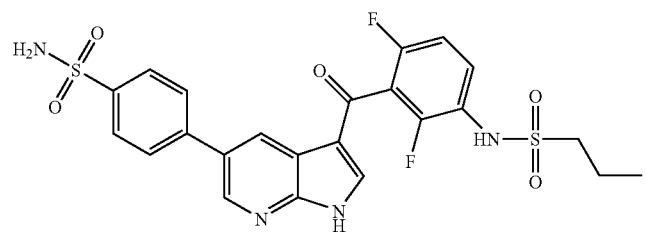 | 535.1 |
| P-2196 | 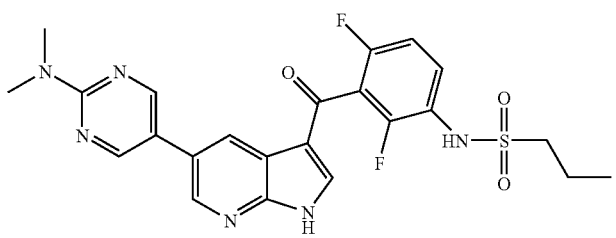 | 501.1 |
| P-2197 | 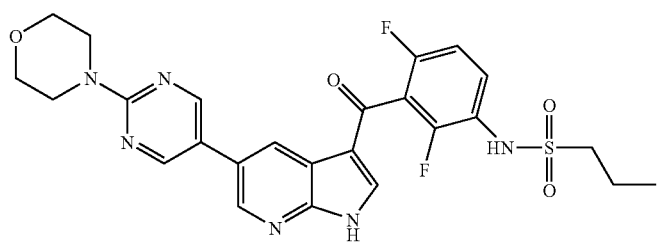 | 543.1 |

| | | |
|---|---|---|
| P-2199 | 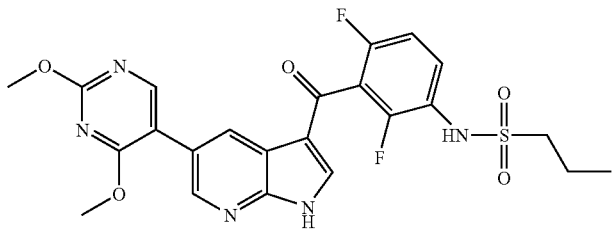 | 517.9 |
| P-2211 | 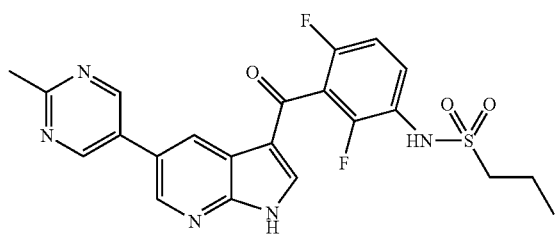 | 472.0 |
| P-2213 | 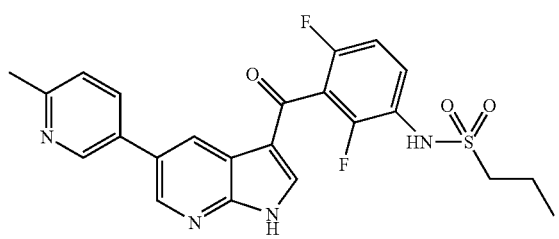 | 471.0 |
| P-2214 | 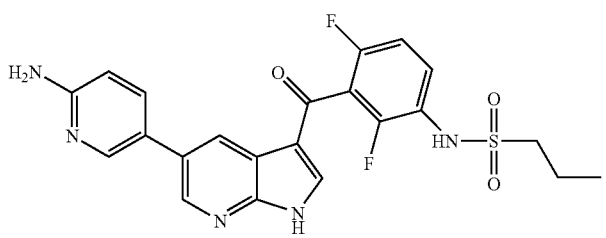 | 472.5 |
| P-2218 | 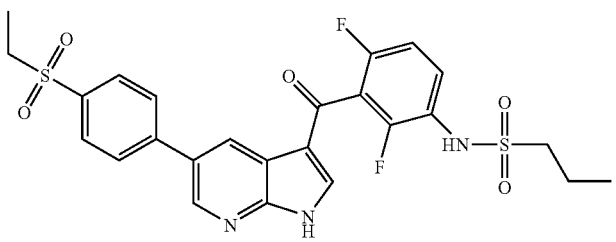 | 546.5 [M − H+]− |
| P-2219 | 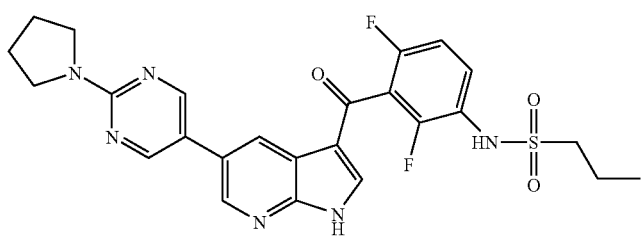 | 527.7 |

| | | |
|---|---|---|
| P-2220 | 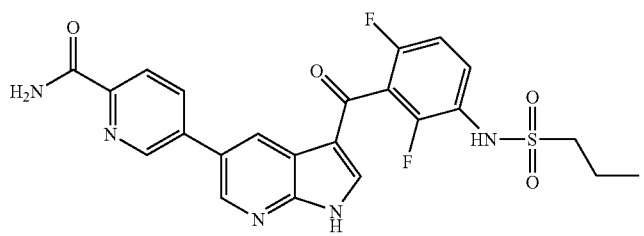 | 500.2 |
| P-2223 | 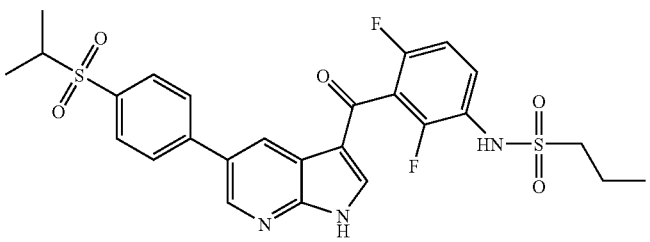 | 562.3 |
| P-2228 | 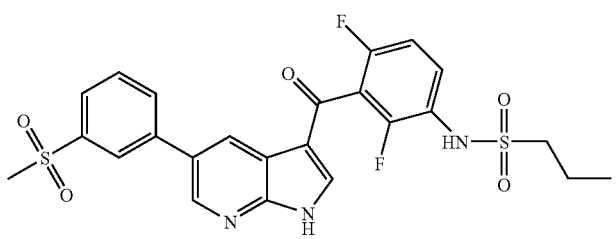 | 532.3 [M − H⁺]⁻ |
| P-2229 | 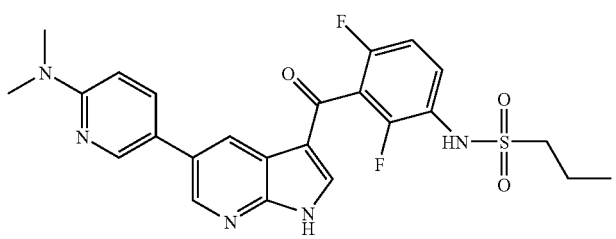 | 500.4 |
| P-2231 | 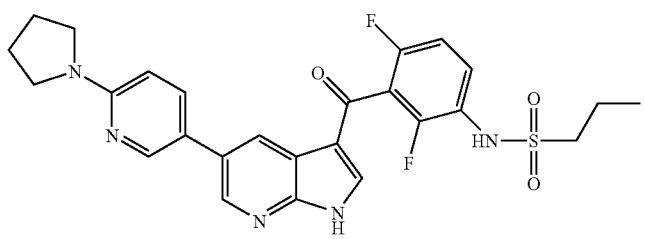 | 526.4 |
| P-2232 | 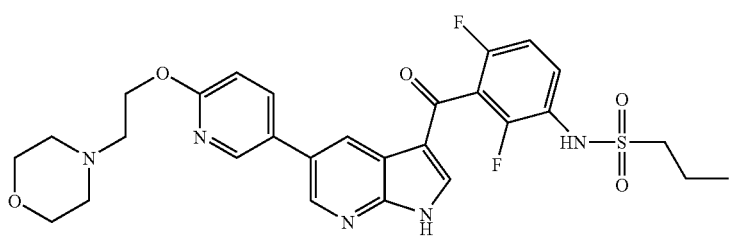 | 586.1 |

| | | |
|---|---|---|
| P-2233 | 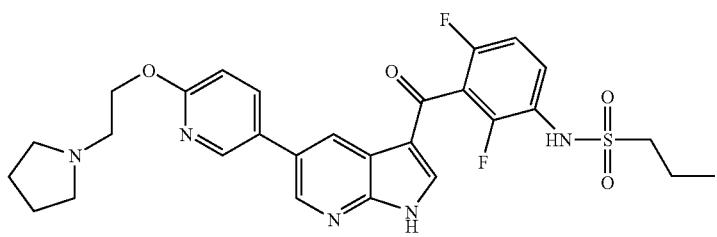 | 570.5 |
| P-2234 | 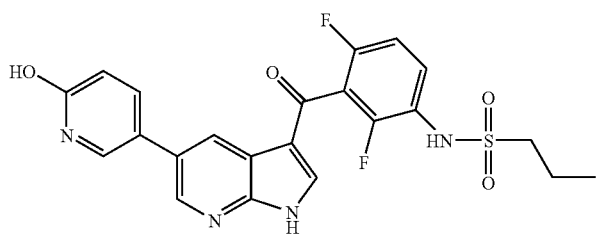 | 473.1 |
| P-2235 | 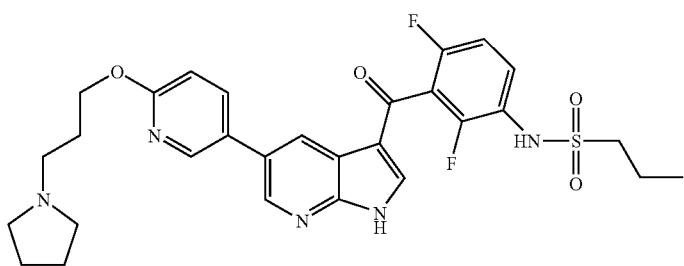 | 584.1 |
| P-2236 | 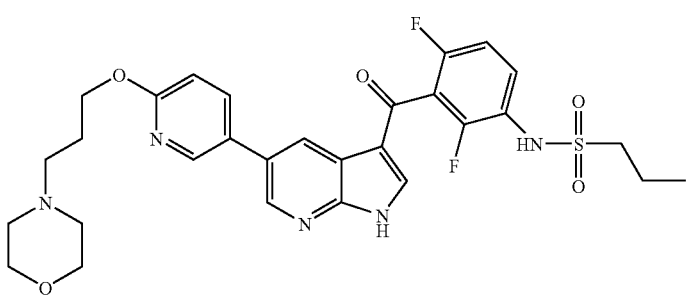 | 600.1 |
| P-2299 | 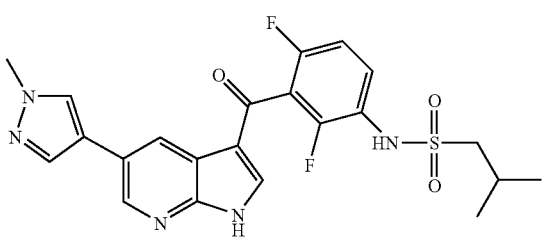 | |
| P-2407 | 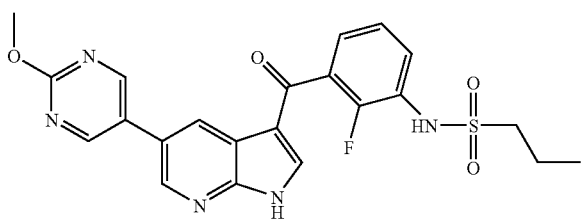 | 470.1 |

P-2408 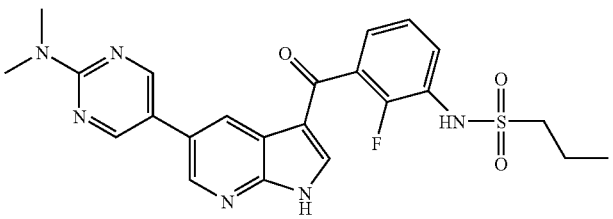 483.6

Example 13

Synthesis of 5-{3-[2,6-difluoro-3-(propane-1-sulfonylamino)-benzoyl]-1H-pyrrolo[2,3-b]pyridin-5-yl}-pyridine-2-carboxylic acid ethylamide P-2151

5-{3-[2,6-Difluoro-3-(propane-1-sulfonylamino)-benzoyl]-1H-pyrrolo[2,3-b]pyridin-5-yl}-pyridine-2-carboxylic acid ethylamide P-2151 was synthesized in two steps from 5-(1H-pyrrolo[2,3-b]pyridin-5-yl)-pyridine-2-carboxylic acid ethylamide 38 as shown in Scheme 13.

Scheme 13

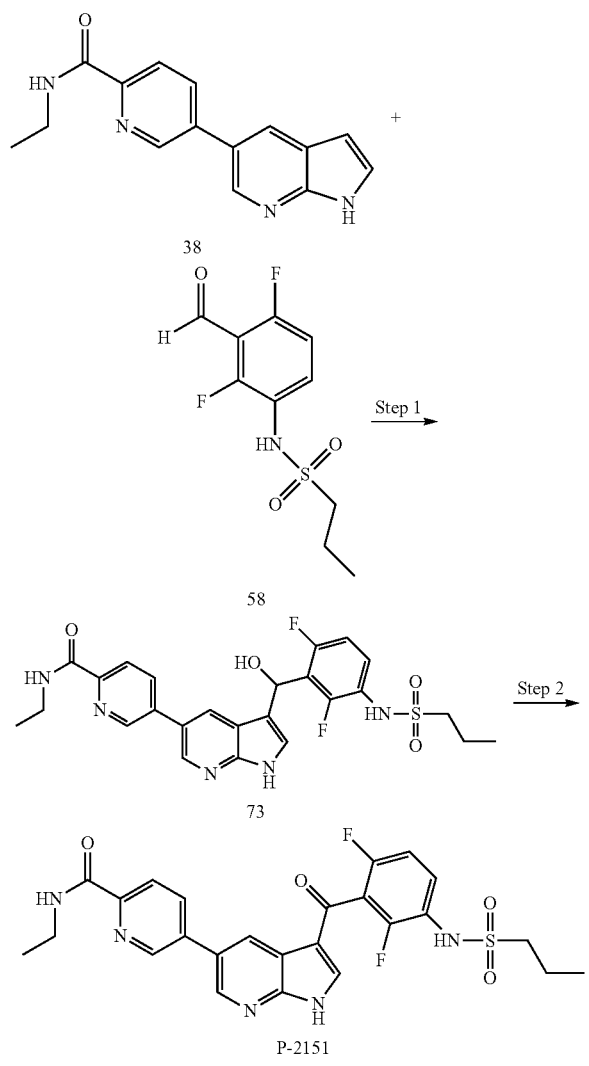

Step 1—Preparation of 5-(3-{[2,6-difluoro-3-(propane-1-sulfonylamino)-phenyl]-hydroxy-methyl}-1H-pyrrolo[2,3-b]pyridin-5-yl)-pyridine-2-carboxylic acid ethylamide (73)

In a round bottom flask, 5-(1H-pyrrolo[2,3-b]pyridin-5-yl)-pyridine-2-carboxylic acid ethylamide (38, 71 mg, 0.27 mmol), propane-1-sulfonic acid (2,4-difluoro-3-formyl-phenyl)-amide (58, 84.2 mg, 0.32 mmol) and potassium hydroxide (44.9 mg, 0.80 mmol) were combined with 1.1 mL of methanol. The reaction was stirred for 2 hours at room temperature. The reaction solution was neutralized with 0.1 N hydrochloric acid, then extracted 3× with ethyl acetate. The organic layer was washed with brine, dried over sodium sulfate, filtered and the filtrate concentrated under vacuum. The resulting residue was purified by silica gel column chromatography to provide the desired compound (73, 55 mg). MS (ESI) [M+H$^+$]$^+$=530.1.

Step 2—Preparation of 5-{3-[2,6-difluoro-3-(propane-1-sulfonylamino)-benzoyl]-1H-pyrrolo[2,3-b]pyridin-5-yl}-pyridine-2-carboxylic acid ethylamide (P-2151)

To 5-(3-{[2,6-difluoro-3-(propane-1-sulfonylamino)-phenyl]-hydroxy-methyl}-1H-pyrrolo[2,3-b]pyridin-5-yl)-pyridine-2-carboxylic acid ethylamide (73, 50 mg, 0.094 mmol) dissolved in 0.76 mL of tetrahydrofuran, Dess-Martin periodinane (48 mg, 0.113 mmol) was added, followed by 1 mL of dimethylformamide. The reaction was allowed to stir at room temperature for 1 hour, then quenched with water and the aqueous layer extracted with ethyl acetate. The organic layer was washed with brine, dried over sodium sulfate, filtered and the filtrate concentrated under vacuum. The resulting residue was purified by silica gel column chromatography to provide the desired compound (P-2151, 30.6 mg). MS (ESI) [M+H$^+$]$^+$=528.2.

Additional compounds were prepared similarly to the protocol of Scheme 13, where optimal reaction conditions may have varied in terms of time and temperature of the reaction, and in chromatography conditions for purification of the desired compounds. The reactions were performed optionally substituting 5-(1H-pyrrolo[2,3-b]pyridin-5-yl)-pyridine-2-carboxylic acid ethylamide 38 with an appropriate 1H-pyrrolo[2,3-b]pyridine and/or propane-1-sulfonic acid (2,4-difluoro-3-formyl-phenyl)-amide 58 with an appropriate aldehyde in step 1. The following compounds were prepared by this procedure:

5-{3-[2,6-Difluoro-3-(propane-1-sulfonylamino)-benzoyl]-1H-pyrrolo[2,3-b]pyridin-5-yl}-pyridine-2-carboxylic acid methylamide (P-2180), 5-{3-[2,6-Difluoro-3-(propane-1-sulfonylamino)-benzoyl]-1H-pyrrolo[2,3-b]pyridin-5-yl}-pyridine-2-carboxylic acid cyclopropylamide (P-2181), Propane-1-sulfonic acid (3-{5-[2-(3-dimethylamino-propoxy)-pyrimidin-5-yl]-1H-pyrrolo[2,3-b]pyridine-3-carbonyl}-2,4-difluoro-phenyl)-amide (P-2203), Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222), Propane-1-sulfonic acid (2,4-difluoro-3-{5-[6-(3-methoxy-propyl)-pyridin-3-yl]-1H-pyrrolo[2,3-b]pyridine-3-carbonyl}-phenyl)-amide (P-2226), Propane-1-sulfonic acid {2,4-difluoro-3-[5-(3-methoxy-prop-1-ynyl)-1H-pyrrolo[2,3-b]pyridine-3-carbonyl]-phenyl}-amide (P-2239), Propane-1-sulfonic acid {3-[5-(3-diethylamino-prop-1-ynyl)-1H-pyrrolo[2,3-b]pyridine-3-carbonyl]-2,4-difluoro-phenyl}-amide (P-2241), and Propane-1-sulfonic acid [3-(5-ethynyl-1H-pyrrolo[2,3-b]pyridine-3-carbonyl)-2,4-difluoro-phenyl]-amide (P-2260).

The following table indicates the 1H-pyrrolo[2,3-b]pyridine (column 2) and aldehyde (column 3) used to afford the desired compound (column 4). The compound number is provided in column 1, and the observed mass is in column 5.

| | 1H-pyrrolo[2,3-b]pyridine | Aldehyde |
|---|---|---|
| P-2151 | | |
| P-2180 | | |
| P-2181 | | |
| P-2203 | | |

| | | |
|---|---|---|
| P-2222 | 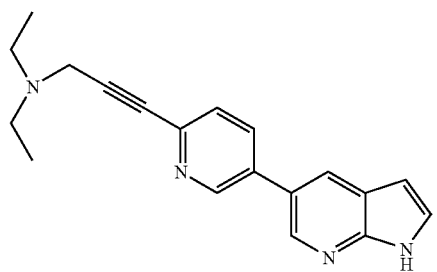 | 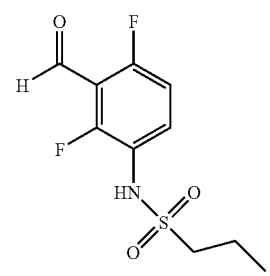 |
| P-2226 | 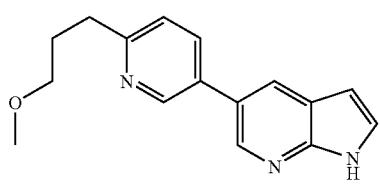 | 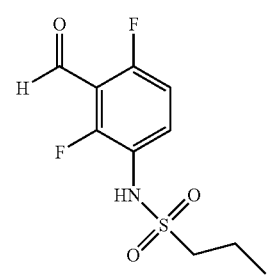 |
| P-2239 | 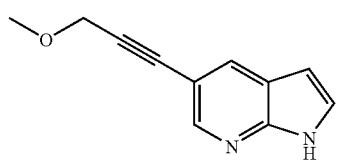 | 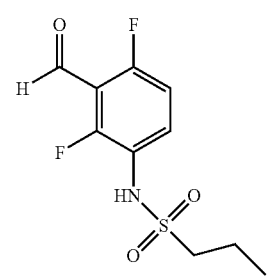 |
| P-2241 | 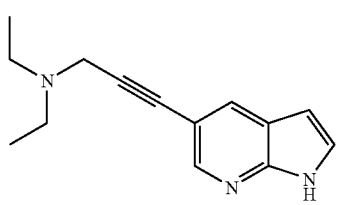 | 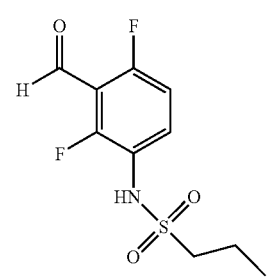 |
| P-2260 | 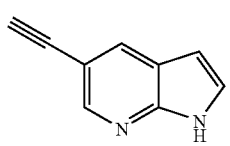 | 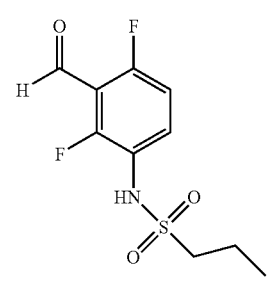 |

-continued
| Compound | MS (ESI) [M + H⁺]⁺ observed |
|---|---|
| P-2151 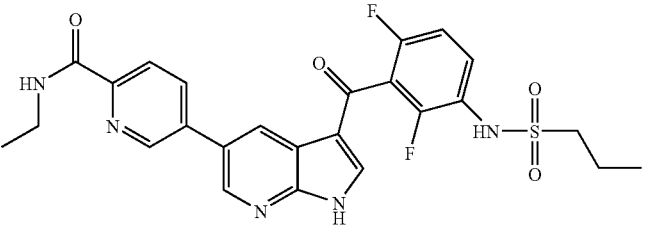 | 528.2 |
| P-2180 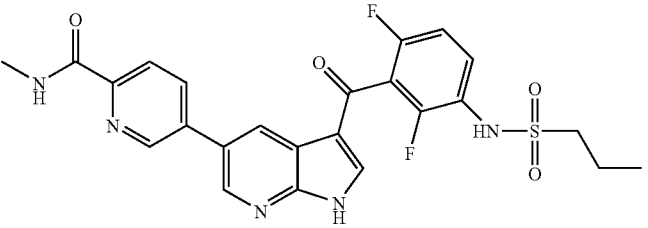 | 512.1 ([M − H⁺]⁻) |
| P-2181 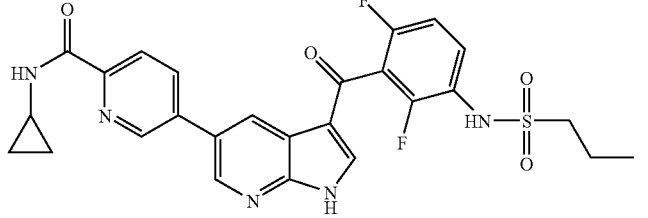 | 538.1 ([M − H⁺]⁻) |
| P-2203 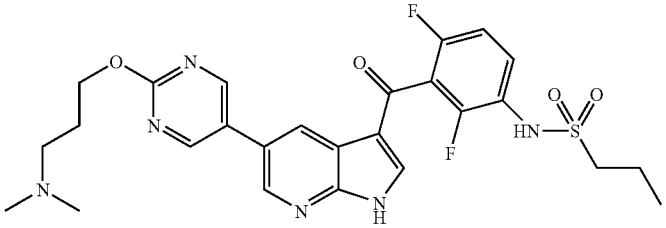 | 559.1 |
| P-2222 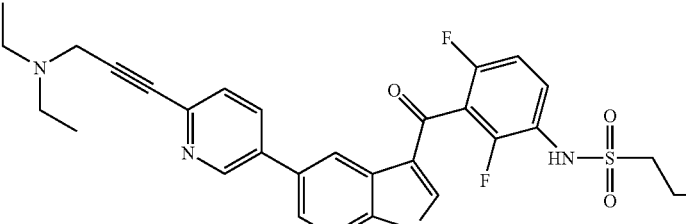 | 566.7 |
| P-2226 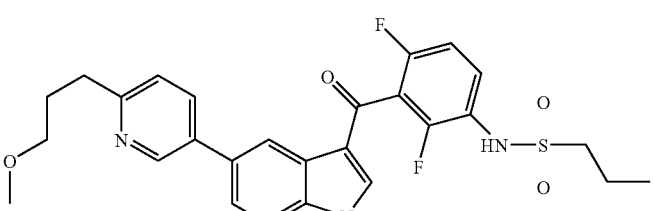 | 529.6 |

-continued

| | | |
|---|---|---|
| P-2239 | 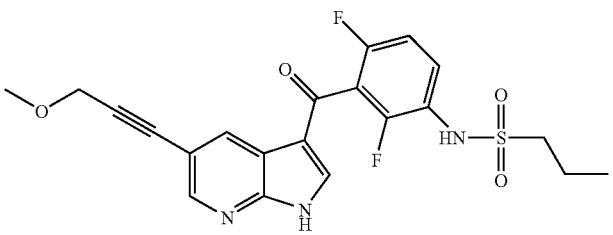 | 448.1 |
| P-2241 | 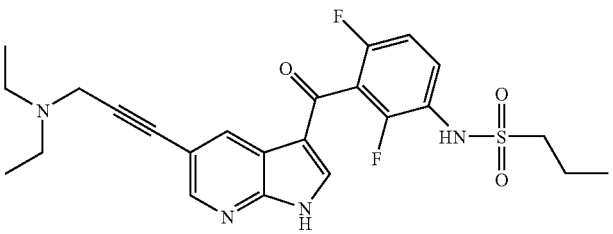 | 489.3 |
| P-2260 | 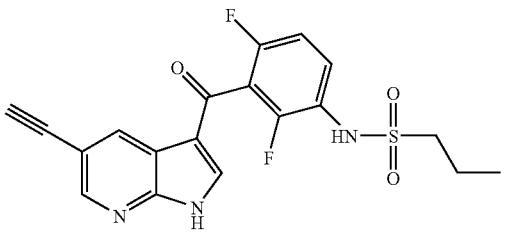 | 404.2 |

Example 14

Synthesis of propane-1-sulfonic acid {2,4-difluoro-3-[5-(6-propyl-pyridin-3-yl)-1H-pyrrolo[2,3-b]pyridine-3-carbonyl]-phenyl}-amide P-2224

Propane-1-sulfonic acid {2,4-difluoro-3-[5-(6-propyl-pyridin-3-yl)-1H-pyrrolo[2,3-b]pyridine-3-carbonyl]-phenyl}-amide P-2224 was synthesized in one step from propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide P-2222 as shown in Scheme 14.

Scheme 14

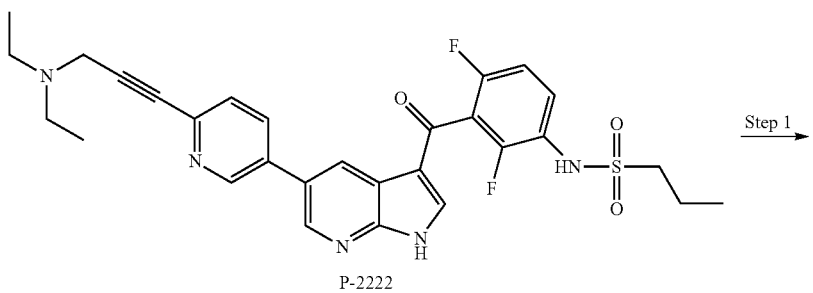
P-2222

Step 1

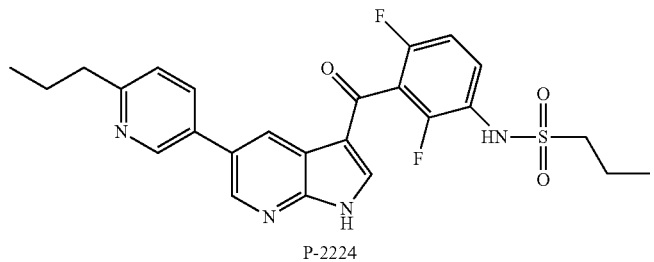
P-2224

Step 1—Preparation of propane-1-sulfonic acid {2,4-difluoro-3-[5-(6-propyl-pyridin-3-yl)-1H-pyrrolo[2,3-b]pyridine-3-carbonyl]-phenyl}-amide (P-2224)

Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide (P-2222, 20.3 mg, 0.0359 mmol) was dissolved in 0.14 mL of methanol. Platinum dioxide (0.81 mg, 0.0036 mmol) was added and the resulting mixture was stirred under an atmosphere of hydrogen for 1 hour. The mixture was filtered through a bed of celite and the filtrate was concentrated. The crude material was purified by flash silica gel chromatography, eluting with a gradient of 15% methanol in dichloromethane to 1% methanol in dichloromethane. The appropriate fractions were combined and concentrated to provide the desired compound as a solid. MS (ESI) $[M+H^+]^+$=499.4.

Example 15

Compound properties

While the inhibitory activity of the compounds on any Raf kinase is important to their activity in treating of disease, the compounds described herein show favorable properties that provide advantages as a pharmaceutical as well. In addition to demonstrating kinase inhibitory activity against each of B-Raf, c-Raf-1 and B-Raf V600E in either biochemical or cell based assays, compounds may show favorable solubility, favorable pharmacokinetic properties, and low Cyp inhibition. The compounds are assessed in the following assays or similar assays available to one skilled in the art.

Assays for biochemical and cell based activity are known in the art, for example, as described in PCT publication WO 2007/002433, the disclosure of which is hereby incorporated by reference as it relates to such assays. For example, the biochemical activity $IC_{50}$ values are determined with respect to inhibition of A-Raf kinase activity, B-Raf kinase activity, c-Raf-1 kinase activity, or B-Raf V600E kinase activity, where inhibition of phosphorylation of a peptide substrate is measured as a function of compound concentration. Compounds to be tested are diluted in dimethyl sulfoxide to a concentration of 0.1 mM. These are serially diluted 15 μL into 30 μL of dimethyl sulfoxide seven times in 96 well plates for a total of 8 dilution points, and for each dilution point 1 μL is added to a well of an assay plate. Plates are prepared such that each well in a 384 well plate contains 1 μL of compound in 10 μL volume with 0.1 ng Raf enzyme (i.e. any of A-Raf, B-Raf, c-Raf-1 or B-Raf V600E, Upstate Biotechnology or prepared by methods known to one of skill in the art), 50 mM HEPES, pH 7.0, 50 mM NaCl, 2 mM $MgCl_2$, 1 mM $MnCl_2$, 0.01% Tween-20, 1 mM DTT, and 100 nM biotin-MEK1 as substrate. The reaction is started with addition of 10 μL of 200 μM ATP (i.e. final 100 μM ATP). After incubation of the kinase reaction for 45 minutes at room temperature, 5 μL/well of Stop Solution is added (25 mM Hepes pH 7.5, 100 mM EDTA, 0.01% BSA with donor beads (Streptavidin coated beads, Perkin Elmer), acceptor beads (Protein A coated, Perkin Elmer), and anti phosphor MEK1/2 antibody (CellSignal), each at final concentration 10 μg/mL). The plates are incubated for 3 hours at room temperature and read on Envision reader (Perkin Elmer). Phosphorylation of Mek1 results in binding of the anti-phosphor-MEK1/2 antibody and association of the donor and acceptor beads such that signal correlates with kinase activity. The signal vs. compound concentration is used to determine the $IC_{50}$.

Compounds are assessed in a variety of cell based assays. For example human cell lines with B-Raf V600E mutation (A375 melanoma, SKMEL3 melanoma, and COLO205 colon adenocarcinoma), as well as tumorigenic cell lines with wild-type B-RAF (SW620 colon adenocarcinoma) or with Ras mutations (SKMEL2 melanoma and IPC298 melanoma). Similar assays may be used to assess additional tumorigenic cell lines with Ras mutations, including, but not limited to, M202, M207, M243, M244, M296, S117, HCT116, HCT15, DLD1, MiaPaCa, A549, NCI-H23, NCI-H460, HOP62, MDA-MB231, Hs-578T, HL60, MOLT-4, and CCRF-CEM.

On day 1, cells are counted, then centrifuged in a conical tube for 5 minutes at 1000 rpm. The supernatant is removed and cells are re-suspended as follows:

SW620 (ATCC catalog #CCL-27): resuspend in Leibovitz's L-15 medium, 2 mM L-glutamine, 10% fetal bovine serum to $6 \times 10^4$ cells/mL.

A375 (ATCC catalog #CRL-1619): resuspend in Dulbecco's modified Eagle's medium, 4 mM L-glutamine, 4.5 g/L D-glucose, 10% fetal bovine serum to $6 \times 10^4$ cells/mL.

COLO205 (ATCC catalog #CCL-222): resuspend in RPMI 1640, 2 mM L-glutamine, 1.5 g/L sodium bicarbonate, 4.5 g/L D-glucose, 10 mM HEPES, 1.0 mM sodium pyruvate, 10% fetal bovine serum to $6 \times 10^4$ cells/mL.

SKMEL2 (ATCC catalog #HTB-68): resuspend in Minimum Eagle essential medium, 2 mM L-glutamine, 1.5 g/L sodium bicarbonate, 0.1 mM non-essential amino acids, 1.0 mM sodium pyruvate, 10% fetal bovine serum to $6 \times 10^4$ cells/mL.

SKMEL3 (ATCC catalog #HTB-69): resuspend in McCoy's 5A medium, 1.5 mM L-glutamine, 15% fetal bovine serum to $6 \times 10^4$ cells/mL.

IPC298 (DSMZ catalog #ACC 251): resuspend in RPMI 1640, 2 mM L-glutamine, 10% fetal bovine serum to $6 \times 10^4$ cells/mL.

The cells are plated, 50 μL in each well of a 96-well dish (Corning 3610) and incubated at 37° C. in 5% $CO_2$ overnight, cells plated to a final concentration of cells as follows:

SW620: 5,000 cells per well.
A375: 2,000 cells per well.
COLO205: 2,000 cells per well.
SKMEL2: 2,000 cells per well.
SKMEL3: 3,000 cells per well.
IPC298: 2,000 cells per well.

On day 2, compound at a maximum concentration of 5 mM is serially diluted 1:3 for a total of 8 point titration with DMSO as a control. A 1 μL aliquot of each dilution point and control is added to 249 μL growth media and 50 μL is added to a well containing cells, providing 10 μM compound at the maximum concentration point. The cells are incubated for 3 days at 37° C. in 5% $CO_2$.

On day 5, ATPlite 1 step Luminescence Assay System (Perkin Elmer #6016739) is brought to room temperature along with the cell cultures. ATPlite is added 25 μL to each well, shake for 2 minutes, and the cells are incubated at room temperature for 10 minutes, then luminescence is read on Safire reader. The measured luminescence correlates directly with cell number, such that the reading as a function of compound concentration is used to determine the $IC_{50}$ value.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. Results for compounds that are tested and show substantially no inhibition below the highest tested concentration are represented as "-" in the tables below. In some instances, the compounds were not tested in all of the assays, or assay results were not valid, as indicated by NA in the tables below.

The following table provides data indicating the A-Raf, B-Raf, B-Raf V600E and c-Raf-1 biochemical inhibitory activity for compounds as described herein:

| Compound number | Biochemical Inhibition IC$_{50}$ (μM) | | | |
|---|---|---|---|---|
| | A-Raf | B-Raf | B-Raf V600E | c-RAf-1 |
| P-2002 | <0.01 | <0.01 | <0.01 | <0.01 |
| P-2003 | NA | <0.1 | <0.1 | <0.01 |
| P-2009 | <0.01 | <0.1 | <0.01 | NA |
| P-2010 | <0.01 | <0.1 | <0.01 | <0.01 |
| P-2011 | <0.01 | <0.1 | <0.01 | NA |
| P-2014 | <0.01 | <0.1 | <0.01 | NA |
| P-2015 | <0.01 | <0.1 | <0.01 | <0.01 |
| P-2016 | <0.01 | <0.1 | <0.01 | NA |
| P-2017 | <0.01 | <0.1 | <0.01 | NA |
| P-2018 | <0.01 | <0.01 | <0.01 | NA |
| P-2019 | <0.01 | <0.01 | <0.01 | NA |
| P-2020 | <0.01 | <0.01 | <0.01 | <0.01 |
| P-2021 | NA | <0.1 | <0.1 | <0.01 |
| P-2022 | <0.1 | <0.1 | <0.01 | <0.01 |
| P-2023 | NA | <0.01 | <0.01 | <0.01 |
| P-2024 | NA | <0.1 | <0.1 | <0.01 |
| P-2029 | NA | <0.1 | <0.01 | <0.01 |
| P-2031 | NA | <1 | <0.1 | <0.1 |
| P-2033 | NA | <0.1 | <0.01 | <0.01 |
| P-2036 | <0.01 | <0.01 | <0.01 | <0.01 |
| P-2037 | <0.01 | <0.1 | <0.01 | <0.01 |
| P-2039 | <0.01 | <0.01 | <0.01 | <0.01 |
| P-2041 | NA | <0.01 | <0.01 | <0.01 |
| P-2042 | NA | <0.01 | <0.01 | <0.01 |
| P-2043 | NA | <0.01 | <0.01 | <0.01 |
| P-2045 | NA | <0.01 | <0.1 | <0.01 |
| P-2046 | <0.01 | <0.01 | <0.01 | <0.01 |
| P-2051 | NA | <0.1 | <0.01 | <0.1 |
| P-2052 | NA | <0.1 | <0.01 | <0.01 |
| P-2053 | NA | <0.01 | <0.01 | <0.01 |
| P-2054 | NA | <0.1 | <0.01 | <0.1 |
| P-2056 | <0.01 | <0.1 | <0.01 | <0.01 |
| P-2069 | <0.1 | <0.01 | <0.01 | <0.01 |
| P-2071 | <0.1 | <0.1 | <0.01 | <0.01 |
| P-2072 | NA | <0.01 | <0.01 | <0.01 |
| P-2073 | NA | <0.1 | <0.1 | <0.01 |
| P-2074 | NA | <0.01 | <0.01 | <0.01 |
| P-2077 | <0.01 | <0.01 | <0.01 | <0.01 |
| P-2086 | NA | <0.01 | <0.01 | <0.01 |
| P-2151 | NA | <0.01 | <0.01 | <0.01 |
| P-2154 | NA | <0.01 | <0.1 | <0.01 |
| P-2155 | NA | <0.01 | <0.01 | <0.01 |
| P-2161 | NA | NA | <0.01 | NA |
| P-2162 | NA | <0.1 | <0.01 | <0.01 |
| P-2165 | <0.01 | <0.01 | <0.01 | <0.01 |
| P-2166 | NA | <0.01 | <0.01 | <0.01 |
| P-2167 | NA | <0.01 | <0.01 | <0.01 |
| P-2168 | NA | <0.01 | <0.01 | <0.01 |
| P-2172 | NA | <0.1 | <0.1 | NA |
| P-2174 | NA | <0.01 | <0.01 | <0.01 |
| P-2177 | NA | <0.01 | <0.01 | NA |
| P-2178 | NA | <0.01 | <0.01 | <0.01 |
| P-2180 | NA | <0.01 | <0.01 | NA |
| P-2181 | NA | <0.01 | <0.01 | NA |
| P-2183 | NA | <0.01 | <0.01 | NA |
| P-2184 | NA | <0.1 | <0.1 | NA |
| P-2185 | NA | <0.01 | <0.01 | <0.01 |
| P-2187 | NA | <0.01 | <0.01 | NA |
| P-2188 | NA | <0.01 | <0.01 | NA |
| P-2189 | NA | <0.01 | <0.01 | <0.01 |
| P-2190 | NA | <0.01 | <0.01 | NA |
| P-2192 | NA | <0.01 | <0.01 | NA |
| P-2193 | NA | <0.01 | <0.01 | <0.01 |
| P-2194 | NA | <0.01 | <0.01 | <0.01 |
| P-2196 | <0.01 | <0.01 | <0.01 | <0.01 |
| P-2197 | NA | <0.01 | <0.01 | NA |
| P-2199 | NA | <0.1 | <0.01 | <0.01 |
| P-2203 | NA | <0.01 | <0.01 | NA |
| P-2211 | NA | <0.01 | <0.01 | <0.01 |
| P-2213 | NA | <0.01 | <0.01 | <0.01 |
| P-2214 | NA | <0.01 | <0.01 | <0.01 |
| P-2218 | NA | <0.1 | <0.1 | <0.1 |
| P-2219 | NA | <0.1 | <0.1 | <0.1 |
| P-2220 | <0.01 | <0.1 | <0.1 | <0.1 |
| P-2222 | NA | <0.01 | <0.01 | <0.01 |
| P-2223 | NA | <0.01 | <0.01 | <0.01 |
| P-2224 | <0.01 | <0.01 | <0.01 | <0.01 |
| P-2226 | NA | <0.01 | <0.01 | <0.1 |
| P-2228 | NA | <0.01 | <0.01 | <0.01 |
| P-2229 | NA | <0.1 | <0.1 | <0.1 |
| P-2231 | <0.01 | <0.01 | <0.01 | <0.1 |
| P-2232 | <0.01 | <0.01 | <0.01 | <0.01 |
| P-2233 | <0.01 | <0.01 | <0.01 | <0.01 |
| P-2234 | <0.01 | <0.01 | <0.01 | <0.01 |
| P-2235 | <0.01 | <0.01 | <0.01 | <0.01 |
| P-2236 | <0.01 | <0.01 | <0.01 | <0.01 |
| P-2239 | <0.01 | <0.1 | <0.01 | <0.01 |
| P-2260 | <0.01 | <0.01 | <0.01 | <0.01 |
| P-2299 | NA | <0.01 | <0.01 | NA |
| P-2407 | <0.01 | <0.1 | <0.01 | <0.01 |
| P-2408 | <0.01 | <0.01 | <0.01 | <0.1 |

The following table provides data indicating the SW620, A375, COLO205, SK-MEL-2, SK-MEL-3, and IPC298 cell growth inhibitory activity for compounds as described herein:

| Compound number | Cell Inhibition IC$_{50}$ (μM) | | | | | |
|---|---|---|---|---|---|---|
| | SW620 | A375 | COLO205 | SKMEL2 | SKMEL3 | IPC298 |
| P-2002 | <20 | <1 | <1 | — | NA | NA |
| P-2003 | NA | <1 | <5 | NA | NA | NA |
| P-2009 | — | <1 | <5 | — | NA | NA |
| P-2010 | — | <1 | <1 | — | NA | NA |
| P-2011 | — | <1 | <1 | — | NA | NA |
| P-2014 | — | <1 | <5 | — | NA | NA |
| P-2015 | — | <1 | <1 | — | NA | NA |
| P-2016 | — | <1 | <5 | — | NA | NA |
| P-2017 | — | <1 | <5 | — | NA | NA |
| P-2018 | — | <1 | <5 | — | NA | NA |
| P-2019 | — | <5 | <5 | — | NA | NA |
| P-2020 | — | <5 | NA | — | NA | NA |
| P-2021 | — | <1 | <5 | NA | NA | NA |
| P-2022 | — | <5 | <5 | — | NA | NA |
| P-2023 | NA | <1 | <5 | NA | NA | NA |
| P-2024 | NA | <5 | <5 | NA | NA | NA |
| P-2029 | — | <5 | <5 | — | NA | NA |
| P-2031 | — | <5 | <5 | — | NA | NA |
| P-2033 | — | <5 | <10 | — | NA | NA |
| P-2036 | — | <5 | <1 | — | NA | NA |
| P-2037 | — | <5 | NA | — | NA | NA |
| P-2039 | — | <5 | <5 | — | NA | NA |
| P-2041 | — | <1 | <1 | NA | <1 | <1 |
| P-2042 | — | <1 | <0.1 | NA | <1 | <1 |
| P-2043 | — | <5 | <1 | NA | NA | NA |

-continued

| Compound number | Cell Inhibition IC$_{50}$ (μM) | | | | | |
|---|---|---|---|---|---|---|
| | SW620 | A375 | COLO205 | SKMEL2 | SKMEL3 | IPC298 |
| P-2045 | — | <5 | <1 | NA | <5 | NA |
| P-2046 | <5 | <1 | <1 | — | NA | NA |
| P-2051 | — | <1 | NA | — | NA | NA |
| P-2052 | — | <1 | <1 | — | NA | NA |
| P-2053 | — | <5 | <1 | — | NA | NA |
| P-2054 | — | <5 | NA | NA | NA | NA |
| P-2056 | <5 | <5 | <5 | — | NA | NA |
| P-2069 | NA | <5 | <1 | NA | NA | NA |
| P-2071 | — | <1 | <1 | — | NA | NA |
| P-2072 | — | <5 | <5 | — | NA | NA |
| P-2073 | — | <10 | <10 | — | NA | NA |
| P-2074 | — | <5 | <10 | — | NA | NA |
| P-2077 | — | <10 | NA | — | NA | NA |
| P-2086 | — | <10 | NA | — | NA | NA |
| P-2151 | NA | <1 | <1 | NA | NA | NA |
| P-2154 | — | <1 | <1 | — | NA | NA |
| P-2155 | — | <1 | <1 | <20 | NA | NA |
| P-2161 | — | <1 | <1 | <10 | NA | NA |
| P-2162 | — | <1 | <1 | <10 | NA | NA |
| P-2165 | <10 | <1 | <1 | <10 | NA | NA |
| P-2166 | <10 | <1 | <0.1 | <5 | NA | NA |
| P-2167 | <10 | <1 | <0.1 | <5 | NA | NA |
| P-2168 | <5 | <1 | <0.1 | <5 | NA | NA |
| P-2172 | <10 | <1 | <1 | <5 | NA | NA |
| P-2174 | — | <1 | <1 | <10 | NA | NA |
| P-2177 | <20 | <1 | <0.1 | <10 | NA | NA |
| P-2178 | — | <0.1 | <0.1 | <5 | NA | NA |
| P-2180 | NA | <1 | NA | NA | NA | NA |
| P-2181 | NA | <1 | NA | NA | NA | NA |
| P-2183 | <20 | <0.1 | <0.1 | — | NA | NA |
| P-2184 | NA | <1 | NA | NA | NA | NA |
| P-2185 | — | <0.1 | <0.1 | — | NA | NA |
| P-2187 | — | <1 | <1 | NA | NA | NA |
| P-2188 | NA | <10 | NA | NA | NA | NA |
| P-2189 | — | <1 | <1 | <10 | NA | <10 |
| P-2190 | <10 | <1 | <1 | NA | NA | NA |
| P-2192 | — | <1 | NA | NA | NA | NA |
| P-2193 | — | <1 | <1 | — | NA | NA |
| P-2194 | NA | <5 | NA | NA | NA | NA |
| P-2196 | — | <1 | <1 | — | <1 | <10 |
| P-2197 | NA | <1 | NA | NA | NA | NA |
| P-2199 | NA | <5 | NA | NA | NA | NA |
| P-2203 | — | <1 | NA | NA | NA | NA |
| P-2211 | — | <1 | <1 | — | NA | NA |
| P-2213 | <20 | <1 | <1 | — | NA | NA |
| P-2214 | <20 | <1 | <1 | — | NA | NA |
| P-2218 | <20 | <0.1 | <0.1 | — | NA | NA |
| P-2219 | — | <0.1 | <0.1 | — | <5 | NA |
| P-2220 | — | <1 | <1 | NA | NA | NA |
| P-2222 | — | <0.1 | <0.1 | NA | NA | NA |
| P-2224 | — | <1 | <1 | NA | NA | NA |
| P-2226 | — | <0.1 | <0.1 | NA | NA | NA |
| P-2228 | — | <1 | NA | NA | NA | NA |
| P-2229 | — | <0.1 | <0.1 | NA | NA | NA |
| P-2231 | <5 | <0.1 | <1 | NA | NA | NA |
| P-2232 | — | <0.1 | <0.1 | NA | NA | NA |
| P-2233 | — | <0.1 | <0.1 | NA | NA | NA |
| P-2234 | — | <5 | <5 | — | NA | NA |
| P-2235 | — | <0.1 | <0.1 | NA | NA | NA |
| P-2236 | — | <0.1 | <0.1 | NA | NA | NA |
| P-2239 | — | <1 | <1 | <20 | NA | NA |
| P-2260 | — | <1 | <1 | NA | NA | NA |
| P-2299 | — | <1 | <1 | — | NA | NA |
| P-2407 | — | <1 | <1 | <20 | NA | NA |
| P-2408 | NA | <0.1 | <1 | NA | NA | NA |

Compounds also demonstrate in vivo activity in a xenograft mouse model for Colo205. Female nu/nu mice are implanted with Colo-205 trocar fragments from donor mice, sub-cutaneous and high in the axilla. Tumor growth is monitored to approximately 100 mg size, and mice are distributed to treatment groups such that the mean tumor burden within a group is within 10% of the overall mean tumor burden. Mice are treated with vehicle control, positive control or compound (8 mice per group) in 5% DMSO and 95% CMC (1%), with compound dosed at 10 mg/kg daily for fourteen days. Mice are observed daily, with tumor burden and body weights measured twice a week. Animals with tumor burden above 1500-2000 mg and any animals in moribund condition are euthanized. The average tumor growth of vehicle control group mice is compared to the average tumor growth of the test compound mice. Percent tumor growth inhibition is calculated as 100×[(tumor growth control-tumor growth test compound)/tumor growth control].

The following table provides data indicating the percent tumor growth inhibition for compounds as described herein in the Colo205 xenograft mouse model:

| Compound number | % Tumor growth inhibition |
|---|---|
| P-2011 | 72 |
| P-2015 | 67 |
| P-2021 | 35 |
| P-2046 | 70 |
| P-2056 | 66 |
| P-2069 | 29 |
| P-2071 | 59 |
| P-2162 | 17 |
| P-2178 | 0 |
| P-2196 | 71 |
| P-2211 | 0 |
| P-2219 | 39 |
| P-2232 | 54 |
| P-2239 | 4 |
| P-2260 | 79 |

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 μL of appropriate buffer is added to each well, and 1 μL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M NaH$_2$PO$_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535 and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3

04, moderate solubility if the threshold concentration is 31.3 µM to 250 µM, and high solubility if the threshold concentration is >250 µM.

The following table provides data indicating the relative solubility (L=low, M=moderate, H=high) based on turbidity threshold concentration at each pH for compounds as described herein:

| Compound number | turbidity threshold (L, M, H) | | | |
|---|---|---|---|---|
| | 1.4 | 4.5 | 6.8 | 7.4 |
| P-2002 | L | L | M | M |
| P-2003 | M | M | M | H |
| P-2009 | L | L | L | M |
| P-2010 | L | L | M | M |
| P-2011 | M | M | M | M |
| P-2014 | L | M | M | M |
| P-2015 | M | L | M | M |
| P-2016 | H | L | M | M |
| P-2017 | M | M | M | M |
| P-2018 | L | M | M | M |
| P-2019 | L | M | M | M |
| P-2020 | M | M | M | M |
| P-2021 | H | M | M | M |
| P-2022 | H | M | M | H |
| P-2023 | H | M | M | M |
| P-2024 | M | L | M | M |
| P-2041 | L | L | L | L |
| P-2042 | L | L | L | L |
| P-2043 | L | L | L | M |
| P-2045 | L | L | L | M |
| P-2046 | L | L | M | M |
| P-2051 | M | M | M | M |
| P-2052 | L | L | M | M |
| P-2053 | L | L | M | M |
| P-2056 | L | L | M | M |
| P-2069 | H | M | M | H |
| P-2071 | M | M | M | M |
| P-2086 | M | M | M | H |
| P-2151 | L | L | L | L |
| P-2155 | L | L | L | L |
| P-2162 | M | M | M | M |
| P-2165 | L | L | L | L |
| P-2166 | L | L | L | L |
| P-2168 | L | L | L | L |
| P-2174 | L | L | L | L |
| P-2177 | H | M | L | L |
| P-2178 | H | M | L | M |
| P-2180 | L | L | L | L |
| P-2181 | L | L | L | L |
| P-2183 | L | L | L | L |
| P-2184 | L | L | L | L |
| P-2185 | L | L | L | L |
| P-2188 | M | L | L | M |
| P-2189 | L | L | L | L |
| P-2190 | L | L | L | L |
| P-2192 | L | L | L | L |
| P-2193 | M | L | L | L |
| P-2194 | L | L | L | L |
| P-2196 | M | L | L | L |
| P-2197 | M | L | L | L |
| P-2211 | M | M | M | M |
| P-2213 | H | M | L | L |
| P-2219 | M | L | L | L |
| P-2222 | L | L | L | L |
| P-2226 | H | L | L | L |
| P-2229 | M | L | M | M |
| P-2231 | L | L | L | L |
| P-2232 | M | M | L | L |
| P-2233 | L | M | L | M |
| P-2235 | L | M | L | M |
| P-2236 | M | M | L | L |
| P-2239 | L | M | L | M |

-continued

| Compound number | turbidity threshold (L, M, H) | | | |
|---|---|---|---|---|
| | 1.4 | 4.5 | 6.8 | 7.4 |
| P-2260 | L | L | L | L |
| P-2407 | L | L | L | L |
| P-2408 | L | L | L | L |

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for compounds, where inhibition of metabolism of a known substrate leads to a decrease in the fluorescence of the metabolized product. The fluorescence of the product is monitored as a function of compound concentration.

Compounds are dissolved in dimethyl sulfoxide to a concentration of 100 mM. These are diluted 1 µL into 82 µL of acetonitrile. An 11 µL aliquot of this solution is then added to 204 µL of cofactor mix (1.3% NADPH Regeneration system Solution A, 1.04% NADPH Regeneration system Solution B from BD Biosciences, 5% acetonitrile and 0.05% dimethyl sulfoxide). These are then serially diluted 1:1 (160 µL to 160 µL co-factor mix) for a total of 10 points. A 10 µL aliquot of this final mixture is dispensed into 384 well assay plates and incubated for 10 minutes at 37° C. Enzyme and substrate mix (10 µL; 0.5 pmol CYP1A2/5 µM CEC; 1.0 pmol CYP2C9/75 µM MFC; 0.5 pmol CYP2C19/25 µM CEC; 1.5 pmol CYP2D6/1.5 µM AMMC; 1.0 pmol CYP3A4/50 µM BFC; or 1.0 pmol CYP3A4/40 M BQ) is added to these assay plates. Assay plates are incubated at 37° C. (CYP1A2-15 min; $CYP2C_{9\text{-}45}$ min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 µM, more preferably $IC_{50}$ values of >10 µM.

The following table provides data indicating the Cyp inhibitory activity for compounds as described herein:

| Compound number | Cyp $IC_{50}$ (µM) | | | | | |
|---|---|---|---|---|---|---|
| | 1A2 | 2C19 | 2C9 | 2D6 | 3A4(BFC) | 3A4(BQ) |
| P-2002 | >10 | 5-10 | 5-10 | >10 | >10 | >10 |
| P-2003 | >10 | >10 | >10 | >10 | >10 | >10 |
| P-2009 | >10 | >10 | >10 | >10 | >10 | >10 |
| P-2010 | >10 | >10 | >10 | >10 | >10 | >10 |
| P-2011 | >10 | >10 | >10 | >10 | >10 | >10 |
| P-2014 | >10 | >10 | >10 | >10 | >10 | >10 |
| P-2015 | >10 | 5-10 | >10 | >10 | >10 | >10 |
| P-2016 | >10 | >10 | <5 | >10 | >10 | 5-10 |
| P-2017 | >10 | >10 | >10 | >10 | >10 | >10 |
| P-2018 | >10 | >10 | >10 | >10 | 5-10 | >10 |
| P-2019 | >10 | >10 | >10 | >10 | 5-10 | >10 |
| P-2020 | >10 | >10 | >10 | >10 | >10 | >10 |
| P-2021 | >10 | >10 | >10 | >10 | >10 | >10 |
| P-2022 | >10 | >10 | 5-10 | >10 | 5-10 | 5-10 |
| P-2023 | >10 | >10 | 5-10 | >10 | 5-10 | <5 |
| P-2024 | >10 | >10 | >10 | >10 | >10 | >10 |
| P-2029 | >10 | >10 | >10 | >10 | >10 | >10 |
| P-2031 | >10 | >10 | >10 | >10 | >10 | >10 |
| P-2033 | >10 | >10 | >10 | >10 | >10 | >10 |
| P-2036 | >10 | >10 | >10 | >10 | >10 | >10 |

-continued

| Compound number | Cyp IC$_{50}$ (μM) | | | | | |
|---|---|---|---|---|---|---|
| | 1A2 | 2C19 | 2C9 | 2D6 | 3A4(BFC) | 3A4(BQ) |
| P-2037 | >10 | >10 | >10 | >10 | >10 | >10 |
| P-2039 | >10 | >10 | >10 | >10 | >10 | >10 |
| P-2041 | >10 | >10 | >10 | >10 | >10 | >10 |
| P-2042 | >10 | >10 | 5-10 | >10 | >10 | >10 |
| P-2043 | >10 | >10 | >10 | 5-10 | >10 | >10 |
| P-2045 | >10 | >10 | >10 | >10 | >10 | >10 |
| P-2046 | >10 | <5 | <5 | >10 | >10 | >10 |
| P-2051 | >10 | >10 | 5-10 | >10 | >10 | >10 |
| P-2052 | >10 | >10 | <5 | >10 | 5-10 | >10 |
| P-2053 | >10 | >10 | 5-10 | >10 | >10 | >10 |
| P-2054 | >10 | >10 | >10 | >10 | >10 | >10 |
| P-2056 | >10 | >10 | 5-10 | >10 | >10 | >10 |
| P-2069 | >10 | >10 | <5 | >10 | <5 | <5 |
| P-2071 | >10 | >10 | >10 | >10 | <5 | <5 |
| P-2072 | >10 | >10 | >10 | >10 | 5-10 | <5 |
| P-2073 | >10 | >10 | >10 | >10 | 5-10 | <5 |
| P-2074 | >10 | >10 | >10 | >10 | >10 | >10 |
| P-2077 | >10 | >10 | 5-10 | >10 | 5-10 | 5-10 |
| P-2086 | >10 | >10 | >10 | >10 | >10 | >10 |
| P-2151 | >10 | >10 | 5-10 | >10 | >10 | >10 |
| P-2154 | >10 | 5-10 | 5-10 | >10 | >10 | >10 |
| P-2155 | >10 | 5-10 | >10 | >10 | >10 | >10 |
| P-2162 | <5 | >10 | 5-10 | >10 | 5-10 | <5 |
| P-2165 | >10 | 5-10 | 5-10 | >10 | >10 | >10 |
| P-2166 | >10 | >10 | >10 | >10 | >10 | >10 |
| P-2167 | >10 | 5-10 | 5-10 | >10 | >10 | 5-10 |
| P-2168 | >10 | 5-10 | <5 | >10 | >10 | 5-10 |
| P-2174 | >10 | 5-10 | <5 | 5-10 | >10 | <5 |
| P-2177 | >10 | 5-10 | <5 | >10 | <5 | >10 |
| P-2178 | >10 | 5-10 | 5-10 | >10 | >10 | <5 |
| P-2180 | >10 | 5-10 | <5 | >10 | >10 | >10 |
| P-2181 | >10 | >10 | <5 | >10 | >10 | >10 |
| P-2183 | >10 | 5-10 | 5-10 | >10 | >10 | >10 |
| P-2184 | >10 | >10 | 5-10 | >10 | >10 | >10 |
| P-2185 | >10 | >10 | <5 | >10 | >10 | >10 |
| P-2187 | >10 | >10 | >10 | >10 | >10 | >10 |
| P-2188 | >10 | >10 | 5-10 | >10 | >10 | >10 |
| P-2189 | >10 | 5-10 | <5 | >10 | >10 | <5 |
| P-2190 | >10 | 5-10 | <5 | >10 | >10 | >10 |
| P-2192 | >10 | >10 | 5-10 | >10 | >10 | >10 |
| P-2193 | >10 | 5-10 | >10 | >10 | 5-10 | >10 |
| P-2194 | >10 | >10 | >10 | >10 | >10 | >10 |
| P-2196 | >10 | >10 | 5-10 | >10 | <5 | >10 |
| P-2197 | >10 | >10 | >10 | >10 | >10 | >10 |
| P-2199 | >10 | >10 | >10 | >10 | >10 | >10 |
| P-2211 | >10 | 5-10 | >10 | >10 | >10 | >10 |
| P-2213 | >10 | >10 | <5 | >10 | >10 | >10 |
| P-2214 | >10 | 5-10 | >10 | >10 | >10 | >10 |
| P-2218 | >10 | NA | >10 | >10 | >10 | >10 |
| P-2219 | >10 | <5 | >10 | >10 | 5-10 | >10 |
| P-2222 | >10 | <5 | 5-10 | 5-10 | >10 | 5-10 |
| P-2223 | >10 | >10 | >10 | >10 | >10 | >10 |
| P-2224 | >10 | 5-10 | 5-10 | >10 | >10 | >10 |
| P-2226 | >10 | >10 | <5 | >10 | >10 | >10 |
| P-2228 | >10 | >10 | >10 | >10 | >10 | >10 |
| P-2229 | >10 | >10 | 5-10 | >10 | >10 | >10 |
| P-2231 | <5 | 5-10 | 5-10 | >10 | >10 | >10 |
| P-2232 | >10 | >10 | 5-10 | >10 | >10 | >10 |
| P-2233 | >10 | 5-10 | >10 | >10 | >10 | >10 |
| P-2235 | >10 | <5 | >10 | >10 | >10 | >10 |
| P-2236 | >10 | <5 | <5 | >10 | <5 | 5-10 |
| P-2239 | >10 | 5-10 | 5-10 | >10 | 5-10 | 5-10 |
| P-2260 | >10 | 5-10 | 5-10 | >10 | <5 | 5-10 |
| P-2407 | >10 | <5 | >10 | >10 | >10 | >10 |
| P-2408 | >10 | >10 | 5-10 | >10 | >10 | >10 |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, $C_{max}$ and half-life relative to previously described compounds.

Example 16

Efficacy of Compounds in Combination with Standard-of-Care Chemotherapeutic Agents in Four Human Cancer Cell Lines Compounds as described herein, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Human tumor cell lines, such as A-375 (malignant melanoma), SK-MEL-2 (malignant melanoma, skin metastasis), COLO 205 (colorectal adenocarcinoma, ascites metastasis) or SW-620 (colorectal adenocarcinoma, lymph node metastasis) can be treated with compounds as described herein alone, or in combination with one of the above-mentioned chemotherapeutic agents.

Tumor cells are grown as a monolayer at 37° C. in a humidified atmosphere (5% $CO_2$, 95% air). Cells are grown in a suitable culture medium, e.g. RPMI 1640 (Ref BE12-702F, Cambrex, Verviers, Belgium) containing 2 mM L-glutamine and supplemented with 10% fetal bovine serum (Ref DE14-801E, Cambrex). For experimental use, the tumor cells are detached from the culture flask by a 5-minute treatment with trypsin-versene (Ref 02-007E, Cambrex), diluted in Hanks' medium without calcium or magnesium (Ref BE10-543F, Cambrex). Trypsin treatment is neutralized by culture medium addition. The cells are counted in a hemocytometer and their viability assessed by 0.25% trypan blue exclusion. The cell lines are checked for mycoplasma contamination with the Mycotect assay kit (Ref 15672-017, Invitrogen, Cergy-Pontoise, France) in accordance with the manufacturer's instructions. The mycoplasma test is assayed from the culture supernatants of the cell lines and compared to negative and positive controls.

The tumor cells (10,000 per well) are plated in 96-well flat-bottom microtitration plates (Ref 055260, Nunc, Dutscher, Brumath, France) and incubated at 37° C. for 24 hours before treatment in 100 μl of drug-free culture medium supplemented with 10% FBS. In order to assess the IC$_{50}$ of each compound to be used for each cell line, the tumor cells are incubated in a 200 µl final volume of RPMI 1640 supplemented with 10% FBS and containing either compounds as described herein, or one of 5-fluorouracil, carboplatin, dacarbazine, gefitinib, oxaliplatin, paclitaxel, SN-38, temozolomide, or vinblastine. The compounds are tested in a suitable concentration range, such as $10^{-8}$ to $10^{-3}$ M for compounds as described herein, 5-fluorouracil, dacarbazine or gefitinib, $10^{-9}$ to $10^{-4}$ M for carboplatin, oxaliplatin, or temozolomide, $10^{-11}$ to $10^{-6}$ M for paclitaxel or SN-38, and $10^{-15}$ to $10^{-10}$ M for vinblastine. Compounds as described herein are dissolved in DMSO and diluted with culture medium to the desired concentrations. 5-fluorouracil (50 mg/ml, Dakota Pharm, LePlessis Robinson, France), carboplatin (10 mg/ml, Aguettant, Lyon, France), and paclitaxel (6 mg/ml, Bristol-Myers Squibb SpA, Rueil Malmaison, France), are diluted with culture medium to the desired concentrations. Dacarbazine (Sigma, Saint Quentin Fallavier, France) and vinblastine (Lilly France S. A., Saint Cloud, France) are dissolved in NaCl 0.9% and diluted with culture medium to the desired concentrations. Gefitinib is dissolved in a mixed solution of RPMI 1640 and DMSO and diluted with culture medium to the desired concentrations (maximum final DMSO of 0.1% v/v). SN-38 (LKT Laboratories, Inc., St. Paul, Minn.) is dissolved in DMSO and diluted with culture medium to the desired concentrations (maximum final DMSO of 0.1% v/v). Temozolomide (LKT Laboratories, Inc., St. Paul, Minn.) is dissolved in water for injection and diluted with culture medium to the desired concentrations. Cells are incubated for 96 hours in the presence of test substances at 37° C. under 5% $CO_2$. At the end of treatments, the cytotoxic activity is evaluated by an MTT assay.

For the MTT assay, at the end of the cells treatment, 20 µl of a 5 mg/ml solution 0.22 µm filtered tetrazolium reagent (MTT, Ref M2128, Sigma) in Phosphate Buffered Saline (PBS, Ref BE17-517Q, Cambrex), is added in each well. Culture plates are incubated for 2 h at 37° C. The resulting supernatant is removed and formazan crystals dissolved with 200 µl of DMSO per well. Absorbency (OD) is measured at 570 nm in each well using VICTOR³™ 1420 multilabeled counter (Wallac, PerkinElmer, Courtaboeuf, France).

The $IC_{50}$ for each compound on each cell line is determined from the OD measurements of each sample. The dose response inhibition of cell proliferation is expressed as:

$$IC = (OD\ of\ drug\ exposed\ cells/OD\ of\ drug\ free\ wells) \times 100.$$

The mean of multiple measurements for each concentration is plotted vs. the drug concentration. The dose-response curves are plotted using XLFit 3 (IDBS, United Kingdom). The $IC_{50}$ (drug concentration to obtain 50% inhibition of cell proliferation) determination values are calculated using the XLFit 3 from semi-log curves. The $IC_{50}$ value determined for each compound in each cell line is used to determine the concentration of compounds as described herein, and of the standard chemotherapeutic to be used in combination.

The cells are treated with a combination of five concentrations of compounds as described herein and five concentrations of one of 5-fluorouracil, carboplatin, dacarbazine, gefitinib, oxaliplatin, paclitaxel, SN-38, temozolomide, or vinblastine, based on the $IC_{50}$ results. The compounds and cells are treated per the IC50 determination described above and assayed by the MTT assay.

The results are assessed to determine whether the combination is synergistic or antagonistic. The compound interactions are calculated by multiple drug effect analysis and are performed by the median equation principle according to the methodology described by Chou and Talalay (Adv. Enzyme Regul. 1984, 22: 27-55).

The combination index (CI) will be calculated by the Chou et al. equation (Adv. Enzyme Regul. 1984, 22: 27-55; Encyclopaedia of human biology, Academic Press, 1991, 2: 371-9; Synergism and Antagonism in Chemotherapy, Academic Press, 1991, 61-102) which takes into account both the potency ($D_m$ or $IC_{50}$) and the shape of the dose-effect curve (the m value). The general equation for the CI of the two compounds is given by:

$$CI = \frac{(D)_1}{(D_x)_1} + \frac{(D)_2}{(D_x)_2} + \frac{(D)_1(D)_2}{(D_x)_1(D_x)_2}$$

where:
$(D_x)_1$ and $(D_x)_2$ in the denominators are the doses (or concentrations) for compound 1 and compound 2 alone which demonstrate x % of inhibition, whereas $(D)_1$ and $(D)_2$ in the numerators are doses of both compounds (1 and 2) in combination that also inhibit x % (iso-effective). CI<1, =1, and >1 indicate synergism, additive effect and antagonism, respectively.

The $(D_x)_1$ and $(D_x)_2$ can be calculated from the median-effect equation of Chou et al. (J. Natl. Cancer Inst. 1994, 86: 1517-24):

$$D_x = D_m \left( \frac{f_a}{(1-f_a)} \right)^{1/m}$$

where:
$D_m$ is the median-effect dose that is obtained from the anti-log of x-intercept of the median-effect plot, x=log(D) versus y=log $\{f_a/(1-f_a)\}$, or $D_m = 10^{-(y\text{-}intercept)/m}$; and m is the slope of the median-effect plot and $f_a$ is the fraction of cells affected by the treatment.

Each CI will be calculated with CalcuSyn software (Biosoft, UK) from the mean affected fraction at each drug ratio concentration.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein.

Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:
1. A compound having the chemical structure of Formula I,
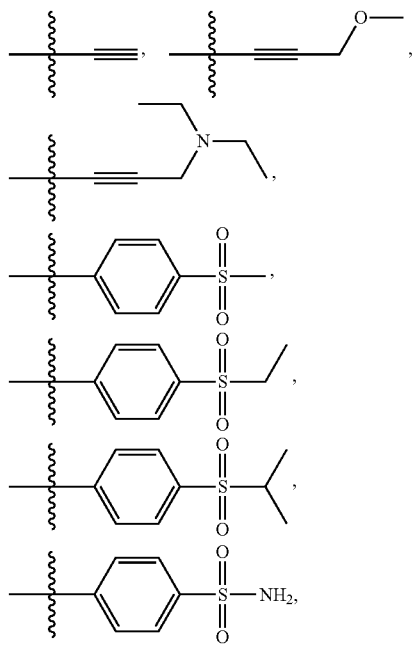
or a salt, a prodrug, or a tautomer thereof,
wherein:
R¹ is
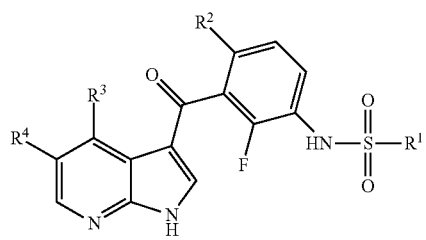
wherein 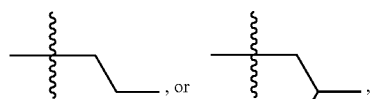
indicates the point of attachment of R¹ to the S(O)₂ shown in Formula 1;
wherein,
when R¹ is
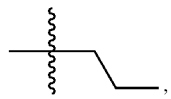
and
R² and R³ are each hydrogen,
R⁴ is
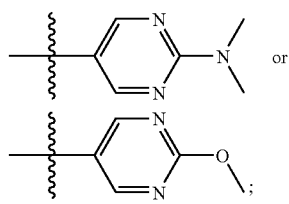
or
when R¹ is
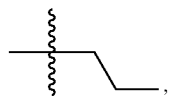
and
R² is fluoro; and
R³ is hydrogen;
R⁴ is selected from the group consisting of

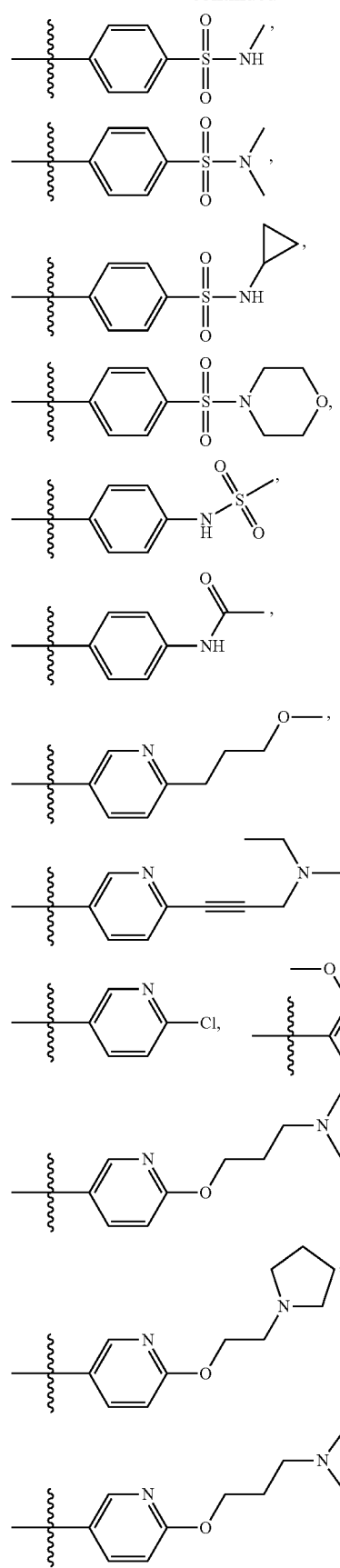
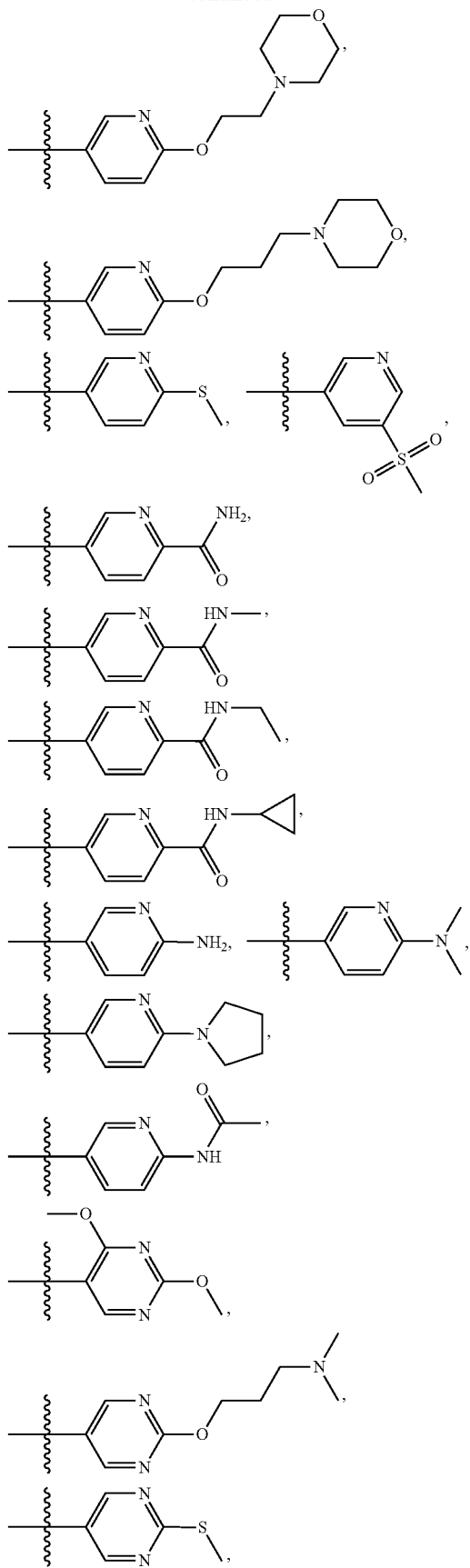

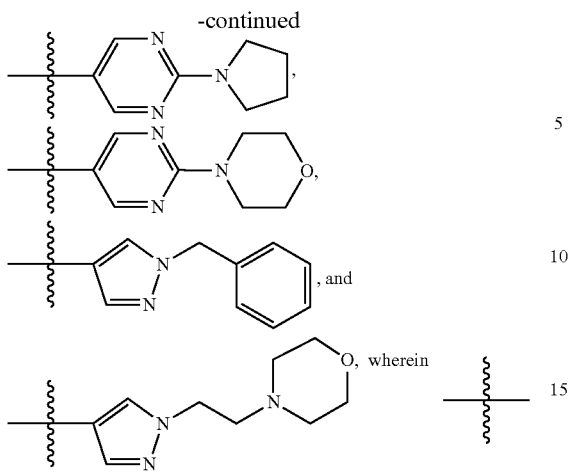

indicates the point of attachment of R[4] to the 5-position of the pyrrolo[2,3-b]pyridine ring shown in Formula I.

2. A composition comprising a pharmaceutically acceptable carrier; and a compound according to claim 1.

3. A kit comprising a compound according to claim 1.

4. A kit comprising a composition according to claim 2.

5. A method for treating a subject suffering from or at risk of a disease or condition, comprising administering to the subject in need thereof an effective amount of a compound according to claim 1, wherein the disease or condition is selected from the group consisting of melanoma, glioma, glioblastoma multiforme, colorectal cancer, thyroid cancer, lung cancer, ovarian cancer, prostate cancer, liver cancer, gastrointestinal stromal tumors, and biliary tract cancer.

6. A method for treating a subject suffering from or at risk of a disease or condition, comprising administering to the subject in need thereof an effective amount of a compound according to claim 1, wherein the disease or condition is selected from the group consisting of melanoma, liver cancer, biliary tract cancer, colorectal cancer, lung cancer, thyroid cancer, kidney cancer, ovarian cancer, and acute myeloid leukemia.

7. A method for treating a subject suffering from or at risk of a disease or condition, comprising administering to the subject in need thereof an effective amount of a compound according to claim 1, wherein the disease or condition is selected from the group consisting of melanoma, colorectal cancer, thyroid cancer, ovarian cancer and biliary tract cancer.

8. A method for treating a subject suffering from or at risk of a disease or condition, comprising administering to the subject in need thereof an effective amount of a composition according to claim 2, wherein the disease or condition is selected from the group consisting of melanoma, glioma, glioblastoma multiforme, colorectal cancer, thyroid cancer, lung cancer, ovarian cancer, prostate cancer, liver cancer, gastrointestinal stromal tumors, and biliary tract cancer.

9. A method for treating a subject suffering from or at risk of a disease or condition, comprising administering to the subject in need thereof an effective amount of a composition according to claim 2, wherein the disease or condition is selected from the group consisting of melanoma, liver cancer, biliary tract cancer, colorectal cancer, lung cancer, thyroid cancer, kidney cancer, ovarian cancer, and acute myeloid leukemia.

10. A method for treating a subject suffering from or at risk of a disease or condition, comprising administering to the subject in need thereof an effective amount of a composition according to claim 2, wherein the disease or condition is selected from the group consisting of melanoma, colorectal cancer, thyroid cancer, ovarian cancer and biliary tract cancer.

11. The compound according to claim 1, wherein the compound is selected from the group consisting of:
- 5-{3-[2,6-Difluoro-3-(propane-1-sulfonylamino)-benzoyl]-1H-pyrrolo[2,3-b]pyridine-5-yl}-pyridine-2-carboxylic acid ethylamide,
- Propane-1-sulfonic acid {3-[5-(6-chloro-pyridin-3-yl)-1H-pyrrolo[2,3-b]pyridine-3-carbonyl]-2,4-difluoro-phenyl}-amide,
- N-(4-{3-[2,6-Difluoro-3-(propane-1-sulfonylamino)-benzoyl]-1H-pyrrolo[2,3-b]pyridine-5-yl}-phenyl)-acetamide,
- Propane-1-sulfonic acid {2,4-difluoro-3-[5-(4-methanesulfonylamino-phenyl)-1H-pyrrolo[2,3-b]pyridine-3-carbonyl]-phenyl}-amide,
- Propane-1-sulfonic acid (2,4-difluoro-3-{5-[4-(morpholine-4-sulfonyl)-phenyl]-1H-pyrrolo[2,3-b]pyridine-3-carbonyl}-phenyl)-amide,
- 4-{3-[2,6-Difluoro-3-(propane-1-sulfonylamino)-benzoyl]-1H-pyrrolo[2,3-b]pyridine-5-y}-N-methyl-benzenesulfonamide,
- N-Cyclopropyl-4-{3-[2,6-difluoro-3-(propane-1-sulfonylamino)-benzoyl]-1H-pyrrolo[2,3-b]pyridine-5-yl}-benzenesulfonamide,
- Propane-1-sulfonic acid (2,4-difluoro-3-{5-[1-(2-morpholin-4-yl-ethyl)-1H-pyrazol-4-yl]-1H-pyrrolo[2,3-b]pyridine-3-carbonyl}-phenyl)-amide,
- Propane-1-sulfonic acid (3-{5-[6-(3-dimethylamino-propoxy)-pyridin-3-yl]-1H-pyrrolo[2,3-b]pyridine-3-carbonyl}-2,4-difluoro-phenyl)-amide,
- 5-{3-[2,6-Difluoro-3-(propane-1-sulfonylamino)-benzoyl]-1H-pyrrolo[2,3-b]pyridine-5-yl}-pyridine-2-carboxylic acid methylamide,
- 5-{3-[2,6-Difluoro-3-(propane-1-sulfonylamino)-benzoyl]-1H-pyrrolo[2,3-b]pyridine-5-yl}-pyridine-2-carboxylic acid cyclopropylamide,
- Propane-1-sulfonic acid {2,4-difluoro-3-[5-(4-methanesulfonyl-phenyl)-1H-pyrrolo[2,3-b]pyridine-3-carbonyl]-phenyl}-amide,
- Propane-1-sulfonic acid {3-[5-(2,6-dimethoxy-pyridin-3-yl)-1H-pyrrolo[2,3-b]pyridine-3-carbonyl]-2,4-difluoro-phenyl}-amide,
- 4-{3-[2,6-Difluoro-3-(propane-1-sulfonylamino)-benzoyl]-1H-pyrrolo[2,3-b]pyridine-5-yl}-N,N-dimethyl-benzenesulfonamide,
- Propane-1-sulfonic acid {2,4-difluoro-3-[5-(6-methylsulfanyl-pyridin-3-yl)-1H-pyrrolo[2,3-b]pyridine-3-carbonyl]-phenyl}-amide,
- Propane-1-sulfonic acid {2,4-difluoro-3-[5-(5-methanesulfonyl-pyridin-3-yl)-1H-pyrrolo[2,3-b]pyridine-3-carbonyl]-phenyl}-amide,
- Propane-1-sulfonic acid {2,4-difluoro-3-[5-(2-methylsulfanyl-pyrimidin-5-yl)-1H-pyrrolo[2,3-b]pyridine-3-carbonyl]-phenyl}-amide,
- Propane-1-sulfonic acid {3-[5-(1-benzyl-1H-pyrazol-4-yl)-1H-pyrrolo[2,3-b]pyridine-3-carbonyl]-2,4-difluoro-phenyl}-amide,
- N-(5-{3-[2,6-Difluoro-3-(propane-1-sulfonylamino)-benzoyl]-1H-pyrrolo[2,3-b]pyridine-5-yl}-pyridin-2-yl)-acetamide,
- 4-{3-[2,6-Difluoro-3-(propane-1-sulfonylamino)-benzoyl]-1H-pyrrolo[2,3-b]pyridine-5-yl}-benzenesulfonamide, Propane-1-sulfonic acid {2,4-difluoro-3-[5-(2-morpholin-4-yl-pyrimidin-5-yl)-1H-pyrrolo[2,3-b]pyridine-3-carbonyl]-phenyl}-amide,
Propane-1-sulfonic acid {3-[5-(2,4-dimethoxy-pyrimidin-5-yl)-1H-pyrrolo[2,3-b]pyridine-3-carbonyl]-2,4-difluoro-phenyl}-amide,
Propane-1-sulfonic acid (3-{5-[2-(3-dimethylamino-propoxy)-pyrimidin-5-yl]-1H-pyrrolo[2,3-b]pyridine-3-carbonyl}-2,4-difluoro-phenyl)-amide,
Propane-1-sulfonic acid {3-[5-(6-amino-pyridin-3-yl)-1H-pyrrolo[2,3-b]pyridine-3-carbonyl]-2,4-difluoro-phenyl}-amide,
Propane-1-sulfonic acid {3-[5-(4-ethanesulfonyl-phenyl)-1H-pyrrolo[2,3-b]pyridine-3-carbonyl]-2,4-difluoro-phenyl}-amide,
Propane-1-sulfonic acid {2,4-difluoro-3-[5-(2-pyrrolidin-1-yl-pyrimidin-5-yl)-1H-pyrrolo[2,3-b]pyridine-3-carbonyl]-phenyl}-amide,
5-{3-[2,6-Difluoro-3-(propane-1-sulfonylamino)-benzoyl]-1H-pyrrolo[2,3-b]pyridin-5-yl}-pyridine-2-carboxylic acid amide,
Propane-1-sulfonic acid (3-{5-[6-(3-diethylamino-prop-1-ynyl)-pyridin-3-yl]-1H-pyrrolo[2,3-b]pyridine-3-carbonyl}-2,4-difluoro-phenyl)-amide,
Propane-1-sulfonic acid (2,4-difluoro-3-{5-[4-(propane-2-sulfonyl)-phenyl]-1H-pyrrolo[2,3-b]pyridine-3-carbonyl}-phenyl)-amide,
Propane-1-sulfonic acid (2,4-difluoro-3-{5-[6-(3-methoxy-propyl)-pyridin-3-yl]-1H-pyrrolo[2,3-b]pyridine-3-carbonyl}-phenyl)-amide,
Propane-1-sulfonic acid {2,4-difluoro-3-[5-(3-methanesulfonyl-phenyl)-1H-pyrrolo[2,3-b]pyridine-3-carbonyl]-phenyl}-amide,
Propane-1-sulfonic acid {3-[5-(6-dimethylamino-pyridin-3-yl)-1H-pyrrolo[2,3-b]pyridine-3-carbonyl]-2,4-difluoro-phenyl}-amide,
Propane-1-sulfonic acid {2,4-difluoro-3-[5-(6-pyrrolidin-1-yl-pyridin-3-yl)-1H-pyrrolo[2,3-b]pyridine-3-carbonyl]-phenyl}-amide,
Propane-1-sulfonic acid (2,4-difluoro-3-{5-[6-(2-morpholin-4-yl-ethoxy)-pyridin-3-yl]-1H-pyrrolo[2,3-b]pyridine-3-carbonyl}-phenyl)-amide,
Propane-1-sulfonic acid (2,4-difluoro-3-{5-[6-(2-pyrrolidin-1-yl-ethoxy)-pyridin-3-yl]-1H-pyrrolo[2,3-b]pyridine-3-carbonyl}-phenyl)-amide,
Propane-1-sulfonic acid (2,4-difluoro-3-{5-[6-(3-pyrrolidin-1-yl-propoxy)-pyridin-3-yl]-1H-pyrrolo[2,3-b]pyridine-3-carbonyl}-phenyl)-amide,
Propane-1-sulfonic acid (2,4-difluoro-3-{5-[6-(3-morpholin-4-yl-propoxy)-pyridin-3-yl]-1H-pyrrolo[2,3-b]pyridine-3-carbonyl}-phenyl)-amide,
Propane-1-sulfonic acid {2,4-difluoro-3-[5-(3-methoxy-prop-1-ynyl)-1H-pyrrolo[2,3-b]pyridine-3-carbonyl]-phenyl}-amide,
Propane-1-sulfonic acid {3-[5-(3-diethylamino-prop-1-ynyl)-1H-pyrrolo[2,3-b]pyridine-3-carbonyl]-2,4-difluoro-phenyl}-amide,
Propane-1-sulfonic acid [3-(5-ethynyl-1H-pyrrolo[2,3-b]pyridine-3-carbonyl)-2,4-difluoro-phenyl]-amide,
2-Methyl-propane-1-sulfonic acid {2,4-difluoro-3-[5-(1-methyl-1H-pyrazol-4-yl)-1H-pyrrolo[2,3-b]pyridine-3-carbonyl]-phenyl}-amide,
and
any salt, prodrug, or tautomer thereof.

* * * * *